United States Patent [19]

Brooks et al.

[11] Patent Number: 5,120,752
[45] Date of Patent: Jun. 9, 1992

[54] CYCLOPROPYL DERIVATIVE LIPOXYGENASE INHIBITORS

[75] Inventors: Dee W. Brooks, Libertyville; Karen E. Rodriques, Grayslake; Bruce W. Horrom, Waukegan; Hormoz Mazdiyasni, Grayslake, all of Ill.

[73] Assignee: Abbott Laboratories, Abbott Park, Ill.

[21] Appl. No.: 621,104

[22] Filed: Dec. 6, 1990

Related U.S. Application Data

[63] Continuation-in-part of Ser. No. 458,067, Dec. 28, 1989, Pat. No. 5,037,853.

[51] Int. Cl.$^5$ ............... C07D 213/643; C07D 213/75; A61K 31/44

[52] U.S. Cl. .................... 514/346; 546/291; 546/332

[58] Field of Search ............. 546/300, 291, 332; 514/346

[56] References Cited

U.S. PATENT DOCUMENTS 4,724,235 2/1988 Shanklin et al. .................. 514/212

*Primary Examiner*—Alan L. Rotman
*Attorney, Agent, or Firm*—Jerry F. Janssen

[57] ABSTRACT

Certain carbocyclic aryl- and heterocyclic aryl- substituted cyclopropyl N-hydroxyureas, N-hydroxy-carboxamides, and N-acyl-N-hydroxyamines inhibit 5- and/or 12-lipoxygenase and are useful in the treatment of inflammatory disease states.

4 Claims, No Drawings

CYCLOPROPYL DERIVATIVE LIPOXYGENASE INHIBITORS

This application is a continuation-in-part of application Ser. No. 458,067 filed Dec. 28, 1989, now U.S. Pat. No. 5,037,853.

TECHNICAL FIELD

This invention relates to novel cyclopropyl compounds possessing lipoxygenase inhibitory activity. It also relates to methods and compositions for inhibiting lipoxygenase enzymes in humans and animal hosts in need of such treatment.

BACKGROUND OF THE INVENTION

5-Lipoxygenase is the first dedicated enzyme in the pathway leading to the biosynthesis of leukotrienes (Samuelsson, B., Science, 120:568 (1983); Hammarstrom, S., Annual Review of Biochemistry, 52:355 (1983)). This important enzyme has a rather restricted distribution, being found predominantly in leukocytes and mast cells of most mammals. Normally 5-lipoxygenase is present in the cell in an inactive form; however, when leukocytes respond to external stimuli, intracellular 5-lipoxygenase can be rapidly activated. This enzyme catalyzes the addition of molecular oxygen to fatty acids with cis,cis-1,4-pentadiene structures, converting them to 1-hydroperoxy-trans,cis-2,4-pentadienes. Arachidonic acid, the 5-lipoxygenase substrate which leads to leukotriene products, is found in very low concentrations in mammalian cells and must first be hydrolyzed from membrane phospholipids through the actions of phospholipases in response to extracellular stimuli. The initial product of 5-lipoxygenase action on arachidonate is 5-HPETE which can be reduced to 5-HETE or converted to leukotriene A4 (LTA4). This reactive leukotriene intermediate is enzymatically hydrated to LTB4 or conjugated to the tripeptide glutathione to produce LTC4. LTA4 can also be hydrolyzed nonenzymatically to form two isomers of LTB4. Successive proteolytic cleavage steps convert LTC4 to LTD4 and LTE4.

Other products resulting from further oxygenation steps have also been described (Serhan, C. N., Hamberg, M., and Samuelsson, B., Proceedings of the National Academy of Sciences, USA, 81:5335 (1985); Hansson, G., Lindgren, J. A., Dahlen, S. E., Hedqvist, P., and Samuelsson, B. FEBS Letters, 130: 107 (1984)).

Products of the 5-lipoxygenase cascade are extremely potent substances which produce a wide variety of biological effects, often in the nanomolar to picomolar concentration range. (Sirois, P., Advances in Lipid Research, R. Paoletti, D. Kritchevesky, editors, Academic Press, 21: 79 (1985).

The remarkable potencies and diversity of actions of products of the 5-lipoxygenase pathway have led to the suggestion that they play important roles in a variety of diseases. Alterations in leukotriene metabolism have been demonstrated in a number of disease states including asthma, allergic rhinitis, rheumatoid arthritis and gout, psoriasis, adult respiratory distress syndrome, inflammatory bowel (Crohn's) disease, endotoxin shock, and ischemia-induced myocardial injury.

SUMMARY OF THE INVENTION

In its principal embodiment, the present invention provides compounds having lipoxygenase inhibiting activity represented by the following structural formula:

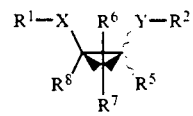

wherein X and Y are absent or are independently divalent alkylene of from one to four carbon atoms, with the proviso that when $R^1$ is carbocyclic aryloxy or heterocyclic aryloxy, X is a divalent alkylene of from two to four carbon atoms.

The group $R^1$ is selected from hydrogen, and unsubstituted or substituted carbocyclic aryl, (carbocyclic aryl)oxy, heterocyclic aryl or (heterocyclic aryl)oxy.

The group $R^2$ is selected from

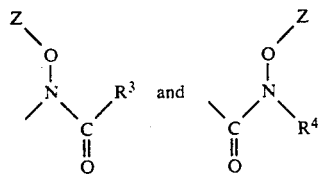

where Z is hydrogen; a metabolically cleavable group; or a pharmaceutically acceptable cation.

$R^3$ is selected from hydrogen; alkyl of from one to six carbon atoms; cycloalkyl of from three to eight carbon atoms; amino; alkylamino of from one to six carbon atoms in which the alkyl group may be optionally substituted by hydroxyl, halogen, or carboxyl; dialkylamino in which the alkyl groups are independently selected from alkyl of from one to six carbon atoms; (cycloalkyl)amino of from three to six carbon atoms; 2-hydroxyethylamino; N-morpholino; N-thiomorpholino;

where n is an integer of from three to eight, and

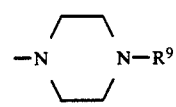

wherein $R^9$ is hydrogen or alkyl of from one to six carbon atoms.

$R^4$ is selected from hydrogen; alkyl of from one to six carbon atoms; and cycloalkyl of from three to eight carbon atoms.

$R^5$ and $R^8$ are independently hydrogen or alkyl of from one to four carbon atoms, and $R^6$ and $R^7$ are independently selected from hydrogen; alkyl of from one to four carbon atoms; and halogen.

In a second embodiment, the present invention provides pharmaceutical compositions comprising a compound as defined above in combination with a pharmaceutically acceptable carrier.

In yet another embodiment, the present invention provides a method of inhibiting 5-and 12-lipoxygenase activity by administering to a mammal in need of such treatment an effective amount of a compound of the present invention.

DETAILED DESCRIPTION

The compounds of the present invention are effective in inhibiting the activity of the 5-ipoxygenase and, as a result, are effective in preventing the formation of the products of lipoxygenase action on arachidonic acid. As discussed above, various products of the so-called "arachidonic acid cascade" of reactions are implicated in a number of allergic and inflammatory disease states. The compounds of this invention, by inhibiting the action of the lipoxygenase enzymes, are effective in treating or ameliorating the effects of these disease states.

The compounds of this invention comprise substituted cyclopropyl compounds, as defined above, falling into one of two main structural subclasses represented by the following structural formulae:

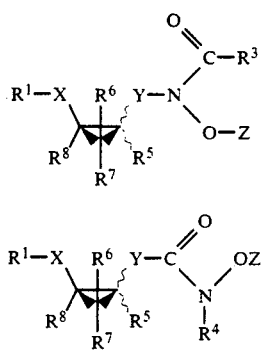

In structures A and B shown above, the values of $R^1$, $R^3$, $R^4$, $R^5$, $R^6$, $R^7$, $R^8$, X, Y, and Z are as previously defined.

In the compounds of this invention, Z may be hydrogen (N-hydroxy compounds), or Z may be a metabolically cleavable group or a pharmaceutically acceptable cation. As used throughout this specification and the appended claims, the term "metabolically cleavable group" denotes a moiety which is readily cleaved in vivo from the compound bearing it, which compound after cleavage remains or becomes pharmacologically active. Metabolically cleavable groups form a class of groups well known to practitioners of the art. They include, but are not limited to such groups as alkanoyl (such as acetyl), unsubstituted and substituted carbocyclic aroyl (such as benzoyl and 1- and 2-naphthoyl), alkoxycarbonyl (such as ethoxycarbonyl), trialkylsilyl (such as trimethyl- and triethylsilyl), monoesters formed with dicarboxylic acids (such as succinyl), and the like. Because of the ease with which the metabolically cleavable groups of the compounds of this invention are cleaved in vivo, the compounds bearing such groups act as pro-drugs of other lipoxygenase inhibitors. The compounds bearing the metabolically cleavable groups have the advantage that they may exhibit improved bioavailability as a result of enhanced solubility and/or rate of absorption conferred upon the parent compound by virtue of the presence of the metabolically cleavable group.

The term "pharmaceutically acceptable cation" denotes non-toxic cations including, but not limited to, cations derived from the alkaline and alkaline earth metals such as lithium, sodium, potassium, calcium, magnesium and the like as well as the ammonium ion and non-toxic cations derived from protonation of primary, secondary, and tertiary amines as well as quaternary ammonium ions. Examples include methylammonium, ethylammonium, dimethylammonium, trimethylammonium, triethylammonium, tetramethylammonium, tetraethylammonium, and the like.

The term "carbocyclic aryl" as used throughout this specification and the appended claims means a group having a single or multiple concatenated or fused aromatic carbocyclic rings, exemplified by phenyl; biphenylyl, 1- or 2-naphthyl and the like.

The term "heterocyclic aryl" means a group having an aromatic single or fused ring system containing one oxygen atom, one sulfur atom, one, two, or three nitrogen atoms, one oxygen atom and one nitrogen atom, or one sulfur atom and one nitrogen atom. Heterocyclic aryl groups are exemplified by 2-, 3-, or 4-pyridyl; 2-, 4-, or 5-pyrimidyl; 2- or 3-furanyl; 2- or 3-pyrrolyl; 2- or 3-thienyl; 2- or 3-benzo[b]thienyl; 2- or 3-benzofuranyl; 2-, 3-, or 4-quinolyl; 2- or 3-indolyl; 2- or 4-thiazolyl; 2- or 3-benzothiazolyl, and imidazolyl.

The term "(carbocyclic aryl)oxy" denotes a carbocyclic aryl group as defined above, connected to the parent molecular moiety through an oxygen atom. Similarly, the term "(heterocycluic aryl)oxy means a heterocyclic group as defined above, attached to the parent molecular moiety through an oxygen atom.

The term "substituted (carbocyclic aryl)" or "substituted (heterocyclic aryl)" as used herein mean, respectively, a carbocyclic aryl group or heterocyclic aryl group, as those terms are defined above, substituted by one or more substituent groups selected from alkyl of from one to six carbon atoms; haloalkyl of from one to six carbon atoms; cycloalkyl of from four to twelve carbon atoms; alkoxy of from one to six carbon atoms; alkylthio of from one to six carbon atoms; carbocyclic aryl, heterocyclic aryl, (carbocyclic aryl)oxy, (heterocyclic aryl)oxy, (carbocyclic aryl)thio, alkoxy(carbocyclic aryl), alkoxy(heterocyclic aryl), wherein the alkoxy portion contains from one to six carbon atoms; alkyl(carbocyclic aryl) or alkyl(heterocyclic aryl) wherein the alkyl portion contains from one to six carbon atoms; alkylthio(carbocyclic aryl) or alkylthio(heterocyclic aryl) wherein the alkylthio portion contains from one to six carbon atoms; (carbocyclic aryl)alkylene and (heterocyclic aryl)alkylene wherein the alkylene portion contains from one to six carbon atoms; (carbocyclic aryl)alkoxy and (heterocyclic aryl)alkoxy wherein the alkoxy portion contains from one to six carbon atoms; (Carbocyclic aryl)alkylthio and (heterocyclic aryl)alkylthio wherein the alkylthio portion contains from one to six carbon atoms; alkanoyl of from one to eight carbon atoms; alkoxycarbonyl of from two to eight carbon atoms; amino; alkylamino of from one to six carbon atoms; dialkylamino in which the alkyl groups are independently selected from alkyl of from one to six carbon atoms; aminocarbonyl; alkylamino-carbonyl of from two to eight carbon atoms; dialkylamino-carbonyl in which the alkyl groups are independently selected from alkyl of from one to six carbon atoms; (N-alkyl-N-alkanoyl)amino of from three to twelve carbon atoms; (N-alkyl-N-alkoxycarbonyl)amino of from three to twelve carbon atoms; (N-alkyl-N-aminocarbonyl)amino of from two to twelve carbon atoms; (N-alkyl-N'-alkylaminocarbonyl)amino of from three to twelve carbon atoms; (N-alkyl-N', N'-dialkylaminocarbonyl- )amino of from three to twelve carbon atoms; hydroxy; halogen; and cyano.

The term "alkyl" denotes a univalent radical derived by the removal of a single hydrogen atom from a straight or branched saturated hydrocarbon. Examples include, methyl, ethyl, propyl, iso-propyl, butyl, sec-butyl, iso-butyl, tert-butyl, pentyl, iso-pentyl and the like. "Haloalkyl" means an alkyl group as just defined, substituted by one or more halogen atoms (fluorine, chlorine, bromine or iodine, fluorine and chlorine being preferred). "Cycloalkyl" means a univalent radical derived by the removal of a single hydrogen atom from a saturated hydrocarbon containing at least one carbocyclic ring. Examples include, cyclobutyl, cyclopentyl, cycolhexyl, methylcyclopentyl, ethylcyclohexyl, norbornanyl, and the like.

The term "alkoxy" means an alkyl group, as previously defined, attached to the parent molecular moiety through an oxygen atom. Likewise, "alkylthio denotes an alkyl group attached through a sulfur atom to the parent molecular moiety.

The terms "(carbocyclic aryl)alkylene" and "(heterocyclic aryl)alkylene" denote a carbocyclic opr heterocyclic aryl group as defined above, attached to the parent molecular moiety through a divalent straight or branched saturated hydrocarbon group to the parent molecular moiety. Examples include 1- and naphth-1-ylmethyl, naphth-2-ylmethyl, 2-phenylethyl, 3-pyridylpropyl, benzo[b]thienylmethyl and the like.

The term "alkanoyl" denotes a hydrogen atom (in the case of formyl) or an alkyl group, as defined above, attached to the parent molecular moiety through a carbonyl group. Examples include formyl, acetyl, propionyl, butyryl, and the like. "Alkoxycarbonyl" denotes and ester group, as that term is commonly understood, attached through its carbonyl group, to the parent molecular moiety. Examples include —COOC$_2$H$_5$, —COO(phenyl) and the like.

The term "aminocarbonyl" denotes the group H$_2$NC(O)—. "Alkylaminocarbonyl" means the group (alkyl)NHC(O)— where alkyl is as previously defined. Similarly, "dialkylaminocarbonyl" denotes (alkyl)$_2$N-C(O)— where the alkyl groups may be the same or different. "(N-Alkyl-N-alkanoyl)amino" denotes the group

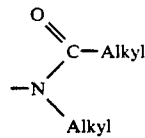

where the alkyl groups may be the same or different and are as defined above.

The term "(N-alkyl-N-alkoxycarbonyl)amino" denotes the group

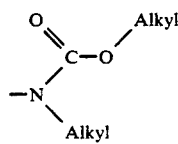

where the alkyl groups may be the same or different and are as defined above.

The term "(N-alkyl-N-aminocarbonyl)amino" means an alkyl-substituted urea group of the formula

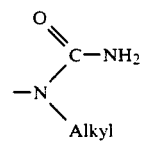

where alkyl is as defined above.

Similarly, the term "(N-alkyl-N'alkylaminocarbonyl)-amino" denotes a group having the structure

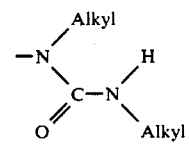

where the alkyl groups may be the same or different and are as defined above.

The term "(N-alkyl-N',N'-dialkylaminocarbonyl)amino denotes a group of the structure

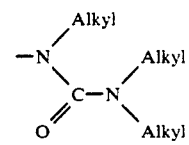

where the alkyl groups may be the same or different and are as defined above.

"Halogen" means fluoro, chloro, bromo- or iodo, with fluoro- and chloro- being preferred.

In all of the above structures, the "wiggle" bonds attaching the groups Y and $R^5$ to the cyclopropyl ring are meant to indicate that the attachment of $R^5$ may be cis- or trans- to that of the group $R^8$.

The compounds of structure A form a class of aryl substituted cyclopropyl compounds (when X is absent) or arylalkyl substituted cyclopropyl compounds (when X is present) which compounds may have the —N-(OZ)COR$^3$ group attached directly to the cyclopropyl ring (when Y is absent), or may have the —N(OZ)-COR$^3$ group attached to the cycopropyl group through an intervening straight or branched alkylene group (when Y is present).

When $R^3$ is hydrogen, alkyl or cycloalkyl, the compounds of structure A comprise N-hydroxy-N-alkanoylamino compounds including, but are not restricted to the following representative examples:

N-(1-trans-(2-phenylcyclopropyl)methyl)-N-hydroxyacetamide;

N-(1-trans-(2-(4-methylphenyl)cyclopropyl)methyl)-N-hydroxyacetamide;

N-(1-trans-(2-(4-methylphenyl)cyclopropyl)ethyl)-N-hydroxyacetamide;

N-(1-trans-(2-(4-bromophenyl)cyclopropyl)methyl)-N-hydroxyacetamide;

N-(1-trans-(2-(4-bromophenyl)cyclopropyl)ethyl)-N-hydroxyacetamide;

N-(1-trans-(2-(4-methoxyphenyl)cyclopropyl)ethyl)-N-hydroxyacetamide;

N-(1-trans-(2-napthyl)cyclopropyl)ethyl)-N-hydroxyacetamide;

N-(1-trans-(2-(2-furanyl)cyclopropyl)ethyl)-N-hydroxyacetamide;

N-(1-trans-(2-(benzo[b]thien-2-yl)cyclopropyl)ethyl)-
N-hydroxyacetamide;
N-(1-trans-(2-(2-thienyl)cyclopropyl)methyl)-N-
hydroxyacetamide;
N-(1-trans-(2-(2-furyl)cyclopropyl)methyl)-N-hydroxyacetamide; and
N-(1-trans-(2-(2-thienyl)cyclopropyl)ethyl)-N-hydroxyacetamide.

Compounds of formula A above when $R^3$ is amino, alkylamino, or dialkylamino, comprise N-hydroxy urea compounds which are exemplified, but not limited to the following:

A. Compounds in which $R^1$ is unsubstituted or substituted carbocyclic aryl or carbocyclic aryloxy as exemplied by:

N-(1-cis-(2-phenylcyclopropyl)methyl-N-hydroxyurea;
N-(trans-(2-phenylcyclopropyl)methyl)-N-hydroxyurea;
N-(1-trans-(2-(4-methylphenyl)cyclopropyl)methyl)-N-hydroxyurea;
N-(1-trans-(4-isopropylphenyl)cyclopropyl)methyl)-N-hydroxyurea;
N-(1-trans-(2-(4-(2-methyl-1-propyl)phenyl)cyclopropyl)-methyl)-N-hydroxyurea;
N-(1-trans-(2-(4-biphenylyl)cyclopropyl)methyl)-N-hydroxyurea;
N-(1-trans-(2-(2-trifluoromethylphenyl)cyclopropyl)-methyl)-N-hydroxyurea;
N-(1-trans-(2-(3-trifluoromethylphenyl)cyclopropyl)-methyl)-N-hydroxyurea;
N-(1-trans-(2-(4-trifluoromethylphenyl)cyclopropyl)-methyl)-N-hydroxyurea;
N-(1-trans-(2-(3,5-bis(trifluoromethyl)phenyl)cyclopropyl)-methyl)-N-hydroxyurea;
N-(1-trans(2-(4-fluorophenyl)cyclopropyl)methyl)-N-hydroxyurea;
N-(1-trans-(2-(2,4-difluorophenyl)cyclopropyl)methyl)-N-hydroxyurea;
N-(1-trans-(2-(3,4-difluorophenyl)cyclopropyl)methyl)-N-hydroxyurea;
N-(1-trans-(2-(2-bromophenyl)cyclopropyl)methyl)-N-hydroxyurea;
N-(1-trans-(2-(3-bromophenyl)cyclopropyl)methyl)-N-hydroxyurea;
N-(1-trans-(2-(4-bromophenyl)cyclopropyl)methyl)-N-hydroxyurea;
N-(1-trans-(2-(4-chlorophenyl)cyclopropyl)methyl)-N-hydroxyurea;
N-(1-trans-(2-(3,4-dichlorophenyl)cyclopropyl)methyl)-N-hydroxyurea;
N-(1-trans-(2-(3,5-dichlorophenyl)cyclopropyl)methyl)-N-hydroxyurea;
N-(1-trans-(2-(3-chloro-4-fluorophenyl)cyclopropyl)-methyl)-N-hydroxyurea;
N-(1-trans-(2-(4-methoxyphenyl)cyclopropyl)methyl)-N-hydroxyurea;
N-(1-trans-(2-(4-methylthiophenyl)cyclopropyl)methyl)-N-hydroxyurea;
N-(1-trans-(2-(4-(dimethylamino)phenyl)cyclopropyl)-methyl)-N-hydroxyurea;
N-(1-trans-(2-(3,4-dimethoxyphenyl)cyclopropyl)methyl)-N-hydroxyurea;
N-(1-trans-(2-(3,5-dimethoxyphenyl)cyclopropyl)methyl)-N-hydroxyurea;
N-(1-trans-(2-(3,4,5-trimethoxyphenyl)cyclopropyl)methyl)-N-hydroxyurea;
N-(1-trans-(2-(3,4-diethoxyphenyl)cyclopropyl)methyl)-N-hydroxyurea;
N-(1-trans-(2-(3-ethoxy-4-methoxyphenyl)cyclopropyl)methyl)-N-hydroxyurea;
N-(1-trans-(3-benzyloxy-4-methoxyphenyl)cyclopropyl)methyl)-N-hydroxyurea;
N-(1-trans-(4-benzyloxy-3-methoxyphenyl)cyclopropyl)methyl)-N-hydroxyurea;
N-(1-trans-(3,4-dibenzyloxyphenyl)cyclopropyl)methyl)-N-hydroxyurea;
N-(1-trans-(2-(3,4-methylenedioxyphenyl)cyclopropyl)methyl)-N-hydroxyurea;
N-(1-trans-(2-(3,4-ethylenedioxyphenyl)cyclopropyl)-methyl)-N-hydroxyurea;
N-(1-trans-(2-(4-methoxy-3-methylphenyl)cyclopropyl)methyl)-N-hydroxyurea;
N-(1-trans-(2-(3-methoxy-4-methylphenyl)cyclopropyl)methyl)-N-hydroxyurea;
N-(1-trans-(2-(2,3-dimethyl-4-methoxyphenyl)cyclopropyl)-methyl)-N-hydroxyurea;
N-(1-trans-(2-(2-bromo-4,5-dimethoxyphenyl)cyclopropyl)-methyl)-N-hydroxyurea;
N-(1-trans-(2-(3-bromo-4,5-dimethoxyphenyl)cyclopropyl)-methyl)-N-hydroxyurea;
N-(1-trans-(2-(3-fluoro-4-methoxyphenyl)cyclopropyl)-methyl)-N-hydroxyurea;
N-(1-trans-(2-(3-bromo-4-methoxyphenyl)cyclopropyl)methyl)-N-hydroxyurea;
N-(1-trans-(2-(4-ethoxyphenyl)cyclopropyl)methyl-N-hydroxyurea;
N-(1-trans-(3-isopropoxyphenyl)cyclopropyl)methyl)-N-hydroxyurea;
N-(1-trans-(2-(4-isopropoxyphenyl)cyclopropyl)methyl)-N-hydroxyurea;
N-(1-trans-(2-(3-bromo-4-isopropoxyphenyl)cyclopropyl)-methyl)-N-hydroxyurea;
N-(1-trans-(2-(4-allyloxyphenyl)cyclopropyl)methyl)-N-hydroxyurea;
N-(1-trans-(2-(4-butoxyphenyl)cyclopropyl)methyl-N-hydroxyurea;
N-(1-trans-(2-(4-(2-methylpropoxy)phenyl)cyclopropyl)methyl)-N-hydroxyurea;
N-(1-trans-(2-(2-phenylethyl)cyclopropyl)methyl)-N-hydroxyurea;
N-(1-trans-(2-(2-phenoxyphenyl)cyclopropyl)methyl)-N-hydroxyurea;
N-(1-trans-(2-(3-phenoxyphenyl)cyclopropyl)methyl)-N-hydroxyurea;
N-(1-trans-(2-(4-phenoxyphenyl)cyclopropyl)methyl)-N-hydroxyurea;
N-(1-trans-(2-(3-(4-methylphenoxy)phenyl)cyclopropyl)methyl)-N-hydroxyurea;
N-(1-trans-(2-(3-methyl-4-phenoxy)phenylcyclopropyl)methyl)-N-hydroxyurea;
N-(1-trans-(2-(4-methyl-3-phenoxyphenyl)cyclopropyl)methyl)-N-hydroxyurea;
N-(1-trans-(2-3-(4-tert-butylphenoxy)phenyl)cyclopropyl-methyl)hydroxyurea;
N-(1-trans-(2-(3-(4-fluorophenoxy)phenyl)cyclopropyl)methyl)-N-hydroxyurea;
N-(1-trans-(2-(3-(3-trifluoromethylphenoxy)phenyl)-cyclopropyl)methyl-N-hydroxyurea;
N-(1-trans-(2-(3-(4-chlorophenoxy)phenyl)cyclopropyl)methyl)-N-hydroxyurea;
N-(1-trans-(2-(3-(3,4-dichlorophenoxy)phenyl)cyclopropyl)-methyl)-N-hydroxyurea;
N-(1-trans-(2-(3-(3,5-dichlorophenoxy)phenyl)cyclopropyl)-methyl)-N-hydroxyurea;
N-(1-trans-(2-(4-methoxy-3-phenoxyphenyl)cyclopropyl)methyl)-N-hydroxyurea;

N-(1-trans-(2-(3-(4-methoxyphenoxy)phenyl)cyclopropyl)-methyl)-N-hydroxyurea;
N-(1-trans-(2-(3-(4-benzyloxyphenoxy)phenyl)cyclopropyl)-methyl)-N-hydroxyurea;
N-(1-trans-(2-(4-(phenylmethoxy)phenyl)cyclopropyl)-methyl)-N-hydroxyurea;
N-(1-trans-(2-(4-(1-(4-(methoxyphenyl)ethoxy)phenyl)-cyclopropyl)methyl)-N-hydroxyurea;
N-(1-trans-(2-(4-(1-phenylethoxy)phenyl)cyclopropyl)-methyl)-N-hydroxyurea;
N-(1-trans-(2-(6-methoxy-2-naphthyl)cyclopropyl)methyl)-N-hydroxyurea;
N-(1-trans-(3,3-difluoro-2-phenylcyclopropyl)methyl)-N-hydroxyurea;
N-(1-trans-((3,3-dimethyl)-2-(3-phenoxyphenyl)cyclopropyl)-methyl)-N-hydroxyurea;
N-(1-cis-(2-phenylcyclopropyl)ethyl)-N-hydroxyurea;
N-(1-trans-(2-phenylcyclopropyl)ethyl)-N-hydroxyurea;
N-(2-trans-(2-phenylcyclopropyl)ethyl)-N-hydroxyurea;
N-(1-trans-(2-(4-methylphenyl)cyclopropyl)ethyl)-N-hydroxyurea;
N-(1-trans-(2-(4-(2-methyl-1-propyl)phenyl)cyclopropyl)-ethyl)-N-hydroxyurea;
N-(1-trans-(2-(4-bromophenyl)cyclopropyl)ethyl)-N-hydroxyurea;
N-(1-trans-(2-(4-methoxyphenyl)cyclopropyl)ethyl)-N-hydroxyurea;
N-(1-trans-(2-(3-phenoxyphenyl)cyclopropyl)ethyl)-N-hydroxyurea;
N-(1-(2-trans-(4-phenoxyphenyl)cyclopropyl)ethyl)-N-hydroxyurea;
N-(1-trans-(2-(4-phenylmethoxy)phenyl)cyclopropyl)ethyl)-N-hydroxyurea;
N-(1-trans-(2-(4-(1-phenylethoxy)phenyl)cyclopropyl)ethyl)-N-hydroxyurea;
N-(1-trans-((3,3-dimethyl-2-phenylcyclopropyl)ethyl)-N-hydroxyurea;
N-(1-trans-(2-(2-phenethyl)cyclopropyl)ethyl)-N-hydroxyurea;
N-(1-trans-((2-napthyl)cyclopropyl)ethyl)-N-hydroxyurea;
N-(1-trans-(2-(6-methoxy-2-naphthyl)cyclopropyl)ethyl)-N-hydroxyurea;
N-(1-trans-(1-methyl-2-phenylcyclopropyl)ethyl-N-hydroxyurea;
N-(1-trans-((3,3-dimethyl)-2-(4-(1-phenylethoxy)-phenyl)-cyclopropyl)ethyl)-N-hydroxyurea;
N-(1-trans-(2-(3-(4-hydroxyphenoxy)phenyl)cyclopropyl)methyl)-N-hydroxyurea;
N-(1-trans-(2-(3-(4-(2-hydroxyethoxy)phenoxy)-phenyl)cyclopropyl)methyl)-N-hydroxyurea;
N-(2-trans-(2-(3-(4-methylphenoxy)phenyl)cyclopropyl)propyl)-N-hydroxyurea;
N-(1-trans-(2-(3-(4-ethoxyphenoxy)phenyl)cyclopropyl)methyl-N-hydroxy-N'-cyclopropylurea;
N-(1-trans-(2-(3-(4-ethoxyphenoxy)phenyl)cyclopropyl)methyl)-N-hydroxyurea;
N-(1-trans-(2-(3-(4-propylphenoxy)phenyl)cyclopropyl)methyl)-N-hydroxyurea.
N-(1-trans-(2-(3-(2-methylphenoxy)phenyl)cyclopropyl)methyl)-N-hydroxyurea;
N-(1-trans-(2-(3-(3-methylphenoxy)phenyl)cyclopropyl)methyl)-N-hydroxy-N'-methylurea;
N-(1-trans-(2-(3-(3-methylphenoxy)phenyl)cyclopropyl)methyl)-N-hydroxyurea;
N-(1-trans-(2-(3-(4-ethylphenoxy)phenyl)cyclopropyl)-methyl)-N-hydroxy-N'-methylhydroxyurea;
N-(1-trans-(2-(3-(4-ethylphenoxy)phenyl)cyclopropyl)-methyl)-N-hydroxyurea;
N-(1-trans-(2-(3-(4-fluorophenoxy)phenyl)cyclopropyl)methyl)-N-hydroxy-N'-methylurea;
N-(1-trans-(2-(3-(4-methylphenoxy)phenyl)cyclopropyl)methyl)-N-hydroxy-N'-methylurea; and
N-(1-trans-(2-(3-(4-methylphenoxy)phenyl)cyclopropyl)ethyl)-N-hydroxyurea.

B. Compounds in which $R^1$ is carbocyclic aryl which is substituted by a substituted or unsubstituted heterocyclic aryl group, exemplified by:
N-(1-trans-(2-(3-(2-pyridyloxy)phenyl)cyclopropyl)methyl)-N-hydroxyurea;
N-(1-trans-(2-(3-(4-pyridyloxy)phenyl)cyclopropyl)methyl)-N-hydroxyurea;
N-(1-trans-(2-(4-(1-(4-pyridyl)ethoxy)phenyl)cyclopropyl)-methyl)-N-hydroxyurea;
N-(1-trans-(2-(4-(1-(2-thienyl)ethoxy)phenyl)cyclopropyl)-methyl-N-hydroxyurea;
N-(1-trans-(2-(3-(2-thienyloxy)phenyl)cyclopropyl)methyl)-N-hydroxyurea;
N-(1-trans-(2-(3-(3-pyridyloxy)phenyl)cyclopropyl)methyl)-N-hydroxyurea.
N-(1-trans-(2-(3-(2-pyridyloxy)phenyl)cyclopropyl)methyl)-N-hydroxy-N'-methylurea;
N-(1-trans-(2-(3-(2-pyridyloxy)phenyl)cyclopropyl)ethyl)-N-hydroxyurea.
N-(1-trans-(2-(3-(2-thienyloxy)phenyl)cyclopropyl)methyl)-N-hydroxyurea;

C. Compounds in which $R^1$ is unsubstituted or substituted heterocyclic aryl or heterocyclic aryloxy, exemplified by:
N-(1-trans-(2-(2-pyridyl)cyclopropyl)methyl)-N-hydroxyurea;
N-(1-trans-(2-(3-pyridyl)cyclopropyl)methyl)-N-hydroxyurea;
N-(1-trans-(2-(4-pyridyl)cyclopropyl)methyl)-N-hydroxyurea;
N-(1-trans-(2-(6-methyl-2-pyridyl)cyclopropyl)methyl)-N-hydroxyurea;
N-(1-(trans-(2-(5-butyl-2-pyridyl)cyclopropyl)methyl)-N-hydroxyurea;
N-(1-trans-(2-(5-bromo-3-pyridyl)cyclopropyl)methyl)-N-hydroxyurea;
N-(1-trans-(2-(2,6-dichloro-4-pyridyl)cyclopropyl)methyl)-N-hydroxyurea;
N-(1-trans-(2-(N'-methyl-2-pyrrolyl)cyclopropyl)methyl)-N-hydroxyurea;
N-(1-trans-(2-(N'-methyl-5-phenyl-2-pyrrolyl)cyclopropyl)-methyl)-N-hydroxyurea;
N-(1-trans-(2-N'-methyl-2-indolyl)cyclopropyl)methyl)-N-hydroxyurea;
N-(1-trans-(2-(4-quinolinyl)cyclopropyl)methyl)-N-hydroxyurea;
N-(1-trans-(2-(3-furanyl)cyclopropyl)methyl)-N-hydroxyurea;
N-(1-trans-(2-(5-ethyl-2-furanyl)cyclopropyl)methyl)-N-hydroxyurea;
N-(1-trans-(2-(5-ethoxymethyl-2-furanyl)cyclopropyl)-methyl)-N-hydroxyurea;
N-(1-trans-(2-(5-(2-phenylethenyl)-2-furanyl)cyclopropyl)-methyl)-N-hydroxyurea;
N-(1-trans-(2-(5-benzyloxymethyl-2-furanyl)cyclopropyl)-methyl)-N-hydroxyurea;
N-(1-trans-(2-(5-phenyl-2-furanyl)cyclopropyl)methyl)-N-hydroxyurea;

N-(1-trans-(2-(5-(2,4-difluorophenyl)phenyl-2-furanyl)-cyclopropyl)methyl)-N-hydroxyurea;
N-(1-trans-(2-(5-bromo-2-furanyl)cyclopropyl)methyl)-N-hydroxyurea;
N-(1-trans-(2-benzofuranyl)cyclopropyl)methyl)-N-hydroxyurea;
N-(1-trans-(2-(3-benzofuranyl)cyclopropyl)methyl)-N-hydroxyurea;
N-(1-trans-(2-(benzo[b]thien-2-yl)cyclopropyl)methyl)-N-hydroxyurea;
N-(1-trans-(2-(2-furanyl)cyclopropyl)ethyl)-N-hydroxyurea;
N-(1-trans-(2-(5-methylfuran-2-yl)cyclopropyl)ethyl)-N-hydroxyurea;
N-(1-trans-(2-(5-(3-pyridyl-2-furanyl)cyclopropyl)methyl)-N-hydroxyurea;
N-(1-trans-(2-(5-(3-pyridyl-2-thienyl)cyclopropyl)methyl)-N-hydroxyurea;
N-(1-trans-(2-(benzo[b]thien-2-yl)cyclopropyl)ethyl)-N-hydroxyurea;
N-(1-trans-(2-(2-thienyl)cyclopropyl)methyl)-N-hydroxyurea;
N-(1-trans-(2-(3-thienyl)cyclopropyl)methyl)-N-hydroxyurea;
N-(1-trans-(2-(3-methyl-2-thienyl)cyclopropyl)methyl)-N-hydroxyurea;
N-(1-trans-(2-(5-methyl-2-thienyl)cyclopropyl)methyl)-N-hydroxyurea;
N-(1-trans-(2-(4-bromo-2-thienyl)cyclopropyl)methyl)-N-hydroxyurea;
N-(1-trans-(2-(5-bromo-2-thienyl)cyclopropyl)methyl)-N-hydroxyurea;
N-(1-trans-(2-(5-chloro-2-thienyl)cyclopropyl)methyl)-N-hydroxyurea;
N-(1-trans-(2-(5-ethoxymethyl-2-thienyl)cyclopropyl)-methyl)-N-hydroxyurea;
N-(1-trans-(2-(5-phenyl-2-thienyl)cyclopropyl)methyl)-N-hydroxyurea;
N-(1-trans-(2-benzo[b]thien-3-yl)cyclopropyl)methyl)-N-hydroxyurea;
N-(1-trans-(2-(4-(benzo[b]thien-3-yl)oxy)cyclopropyl)-methyl)-N-hydroxyurea;
N-(1-trans-(2-(5-(5-methyl-2-thienyl)-2-thienyl)cyclopropyl)-methyl-N-hydroxyurea;
N-(1-trans-(2-(2-thiazolyl)cyclopropyl)methyl-N-hydroxyurea;
N-(1-trans-(2-(2-benzothiazolyl)cyclopropyl)methyl)-N-hydroxyurea;
N-(1-trans-(2-(2-thienyl)cyclopropyl)methyl)-N-hydroxyacetamide;
N-(1-trans-(2-(2-furanyl)cyclopropyl)methyl)-N-hydroxyacetamide;
N-(1-trans-(2-(2-thienyl)cyclopropyl)ethyl)-N-hydroxyacetamide;
N-(1-trans-(2-(3-(6-methyl-2-pyridyloxy)phenyl)phenyl) cyclopropyl)methyl)-N-hydroxyurea;
N-(1-trans-(2-(3-(3-quinonyloxy)phenyl)cyclopropyl) methyl)-N-hydroxyurea.
N-(1-trans-(2-(3-(2-thiazolyloxy)phenyl)cyclopropyl) methyl)-N-hydroxyurea;
N-(1-trans-(2-(5-methyl-2-thienyl)cyclopropyl)ethyl)-N-hydroxy-N'-methylurea;
N-(1-trans-(2-(5-methyl-2-thienyl)cyclopropyl)ethyl)-N-hydroxyurea.
N-(1-trans-(2-(2-furanyl)cyclopropyl)ethyl)-N-hydroxy-N'-methylurea;
N-(1-trans-(2-(5-methyl-2-furanyl)cyclopropyl)ethyl)-N-hydroxy-N'-methylurea;
N-(1-trans-(2-(3-furanyl)cyclopropyl)methyl)-N-hydroxy-N'-methylurea.
N-(1-trans-(2-(3-thienyl)cyclopropyl)ethyl)-N-hydroxy-N'-methylurea;
N-(1-trans-(2-(3-thienyl)cyclopropyl)methyl)-N-hydroxy-N'-methylure;
N-(1-trans-(2-(3-thienyl)cyclopropyl)methyl)-N-hydroxyurea
N-(1-trans-(2-(3-thienyl)cyclopropyl)ethyl)-N-hydroxyurea;
N-(1-trans-(2-(3-furanyl)cyclopropyl)ethyl)-N-hydroxy-N'-methylurea;
N-(1-trans-(2-(3-furanyl)cyclopropyl)ethyl)-N-hydroxyurea;
N-(1-trans-(2-(3-furanyl)cyclopropyl)methyl)-N-hydroxyurea;
N-(1-trans-(2-(2-thienyl)cyclopropyl)methyl)-N-hydroxyurea;
N-(1-trans-(2-(2-thienyl)cyclopropyl)ethyl)-N-hydroxyurea;
N-(1-trans-(2-(2-furanyl)cyclopropyl)methyl)-N-hydroxyurea;
N-(1-trans-(2-(2-(4-chlorophenoxy)-5-thiazolyl)cyclopropyl) methyl)-N-hydroxyurea; and
N-(1-trans-(2-(2-(5-(4-fluorophenoxy)furanyl)cyclopropyl) methyl)-N-hydroxyurea.

The compounds of structure B comprise aryl cyclopropyl compounds (when X is absent) or arylalkyl cyclopropyl compounds (when X is present). The compounds may have the —C(O)N(OZ)— group attached directly to the cyclopropyl ring (when Y is absent), or may have the —C(O)N(OZ)— group attached to the cyclopropyl group through an intervening straight or branched alkylene group (when Y is present).

$R^4$ is hydrogen, alkyl or cycloalkyl, hence the compounds of structure B comprise N-hydroxy carboxamide compounds including, but not restricted to the following representative examples:

N-methyl-N-hydroxy-trans-2-phenylcyclopropyl carboxamide; and
N-methyl-N-hydroxy-trans-2-(3-phenoxyphenyl)cyclopropyl) carboxamide.

SYNTHESIS OF THE COMPOUNDS OF THE PRESENT INVENTION

Compounds of this invention are prepared by the following processes. In certain cases where the starting aldehyde contains functional groups which might interfere with the desired transformation outlined in the following methods, it is recognized that common methods of protection of these groups followed by deprotection at a later stage in the preparation of the desired product can be applied. A general reference source for methods of protection and deprotection is T. W. Greene, "Protective Groups in Organic Synthesis", Wiley-Interscience, New York, 1981.

Control of the stereochemistry of the group $R^1$— (where X is absent) or $R^1$—X— relative to the group —$R^2$ (when Y is absent) or —$YR^2$ is achieved by the choice of starting olefinic compound employed in producing the cyclopropyl ring in compounds of this invention. If the two groups in question are attached to the carbon-carbon double bond in the starting material in a trans-configuration, the groups will be trans in the resulting cyclopropyl product compound. Similarly, employing a starting olefin in which the groups $R^1$— (or $R^1$—X—) and —$R^2$ or (—$YR^2$) are in a cis-configuration about the carbon-carbon double bond will result in a cyclopropyl product compound in which the groups are in a cis-configuration with regard to the ring. While compounds of the present invention in which the groups $R^1$— (or $R^1$—X—) and —$R^2$ (or —$YR^2$) are trans to one another on the cyclopropyl ring are preferred, the present invention contemplates both the cis- and trans-isomeric forms.

Moreover, when the substituent groups $R^6$ and $R^7$ are different, there are three chiral centers in the molecules of the compounds of this invention, one at each carbon atom of the cyclopropyl ring, leading to the possible existence of eight stereoisomeric forms of the compounds. In addition, chiral centers present in the alkylene groups —X— and —Y— or in the various substituent groups present the possibility of additional stereoisomeric forms of the compounds of this invention. The present invention contemplates all stereoisomeric forms of the compounds encompassed within the generic structural formula given above.

Particular enantiomeric forms of the compounds of this invention can be separated from mixtures of the enantiomers by first reacting the compounds with a cleavable resolving group which is itself a pure enantiomer to form diastereomers which are then separated by techniques well known in the art such as chromatography. The cleavable resolving group is then removed by known chemical techniques to yield the desired enantiomer in pure form. Compounds of the present invention which are in admixture with diastereomers are isolated in pure form by physical separation techniques such as chromatography.

In some particular instances, the chemical processes for preparing the present compounds may, when a new chiral center is created as a result of the reation, lead to the predominance of one enantiomeric form over the other.

The synthetic processess useful for the syntheses of the compounds of this invention are generally outlined by the sequence of reactions illustrated in Reaction Scheme 1. In Alternative Method A an aldehyde I is converted to the a,b-unsaturated acid II (R=OH). This intermediate is then converted into an N-methoxy-N-methylamide intermediate III (R=N(OCH$_3$)CH$_3$) which is subsequently cyclopropanated to provide intermediate V. Alternatively the amide III can be converted into a ketone IV (R=alkyl) which can be cyclopropanated to provide intermediate VI(R=alkyl). Both V and VI can then be converted by a sequence of known procedures to provide the novel compounds VII of this invention with inhibitory activity as lipoxygenase inhibitors.

Method B outlines the conversion of the N-methoxy-N-methylamide intermediate V (R=N(OCH$_3$)CH$_3$) into the corresponding carboxylic acid VIII which is then converted to the novel compounds IX of this invention with inhibitory activity as lipoxygenase inhibitors.

Reaction Scheme 1
(Alternative Method A)

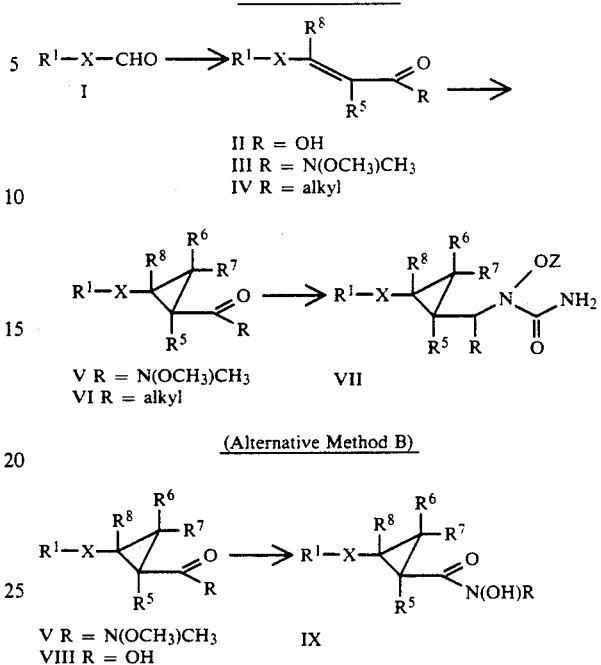

One example of this process is described in Reaction Scheme 2 and involves conversion of the aldehyde I into the corresponding a,b-unsaturated carboxylic acid II by condensation with malonic acid followed by in situ decarboxylation. The carboxylic acid II is then transformed into an a,b-unsaturated ketone using methodology described by Weinreb et. al. *Tetrahedron Letters*, 1981, 22(39), 3815. The carboxylic acid II is converted to its N-methoxy-N-methylamide III, via its acid chloride, then reacted with an organometallic to provide the desired a,b-unsaturated ketone IV. The cyclopropyl moiety is then formed using chemistry developed by Corey et. al, *J. Amer. Chem. Soc.*, 1965, 87(6), 1353 and *Angew. Chem.*, 1973, 85, 867 or Johnson et al. *J. Amer. Chem. Soc.*, 1973, 4287. The unsaturated ketone IV is treated either with the sodium salt of a sulfoxonium salt of the lithiate of a sulfoximine to afford the a,b-cyclopropyl ketone V. The ketone V can be readily converted to the desired compounds of Formula 1 by known methods. For example, reaction of the ketone V with hydroxylamine followed by reduction with BH$_3$.pyridine affords the hydroxylamine VI which can be treated with an isocyanate to provide the desire N-hydroxyurea compounds of Formula 2.

Reaction Scheme 2

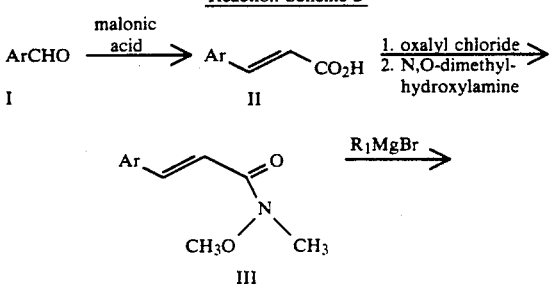

-continued
Reaction Scheme 2

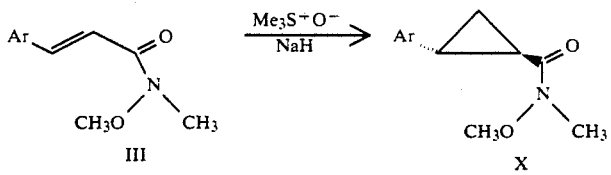

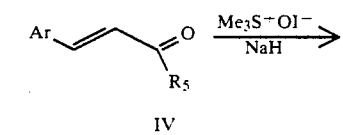

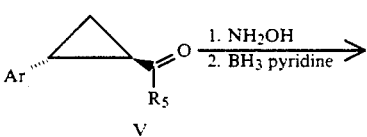

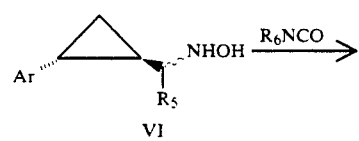

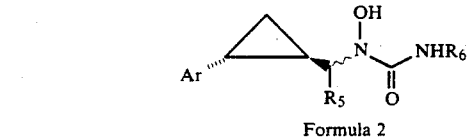

A more preferred and novel approach to these systems involves subjecting the N-methoxy-N-methylamide III, directly to the cyclopropanation conditions to afford the cyclopropyl amide X as outlined in Reaction Scheme 3. This N-methoxy-N-methylamide intermediate can then be diverted into two different pathways to compounds of Formula 2 where $R_5$ = H. or a substituent R. For the case where $R_5$ is a substituent, the amide X is treated with a Grignard reagent, RMgBr, to afford the ketone V, which is then carried on to the N-hydroxy urea as described in Reaction Scheme 2. For cases where R=H, the amide X is treated with diisobutylaluminum hydride to afford the aldehyde XI, which is then carried on to the N-hydroxy urea in the usual manner.

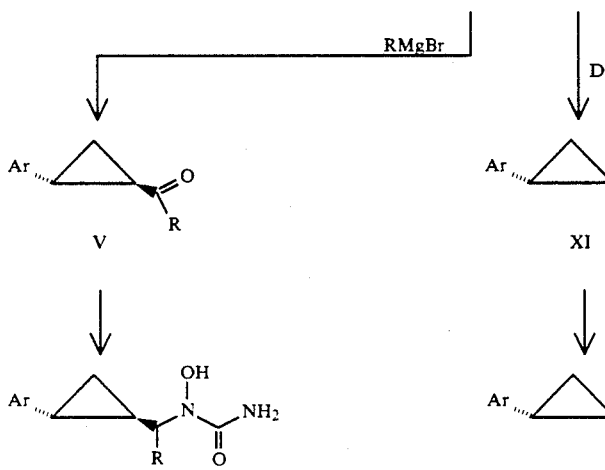

The N-hydroxylamine VI can also be readily converted to compounds of Formula 3 by known methods as outlined in Reaction Scheme 4. The hydroxylamine is bis-acylated by treatment with an acid chloride and base or by treatment with a suitably activated acyl equivalent. This intermediate XII is then selectively hydrolyzed to provide the N-hydroxy amides of Formula 3.

Reaction Scheme 4

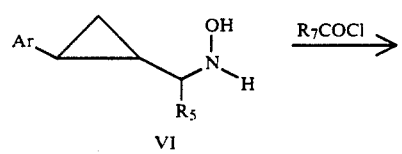

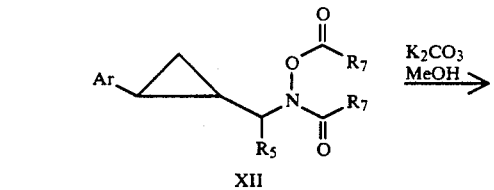

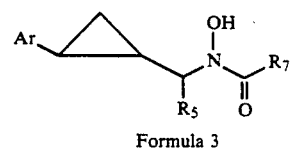

Hydroxamic acids of Formula 4 are prepared as outlined in Reaction Scheme 5, from the cyclopropyl carboxyaldehyde XI by oxidation with silver oxide to the corresponding acid XIII. The acid is converted to the corresponding acyl chloride and treated with a hydroxylamine to provide hydroxamic acids of Formula 4.

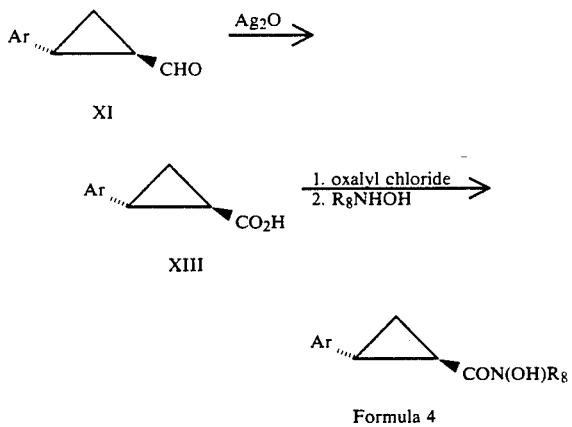

Reaction Scheme 5

All of the chemistry taught above may be performed on compounds possessing an alkyl link between the aryl carrier and the cyclopropyl moiety. To obtain the a,b-unsaturated acid II which is the common starting point for these compounds, the aldehyde I is elaborated by the Wittig reaction with a stabilized ylide, followed by hydrolysis of the resulting ester to afford the prerequisite acid II. (Reaction Scheme 6) which can be further converted to compounds of Formula I as described previously.

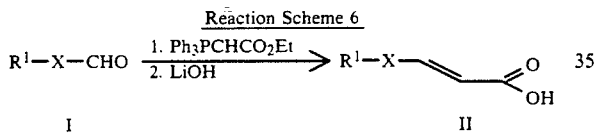

Reaction Scheme 6

To obtain compounds where there is an alkyl link between the N-hydroxyurea functionality and the cyclopropyl moiety, homologation is performed on the aldehyde of type XIV (Reaction Scheme 7). For example, the aldehyde XIV is treated under Wittig reaction conditions with the ylide, methoxymethylenetriphenylphosphorane to afford the intermediate enol ether which is hydrolyzed under acidic conditions to afford the one carbon homologated aldehyde XV. This aldehyde can be further converted to compound of Formula I as described previously.

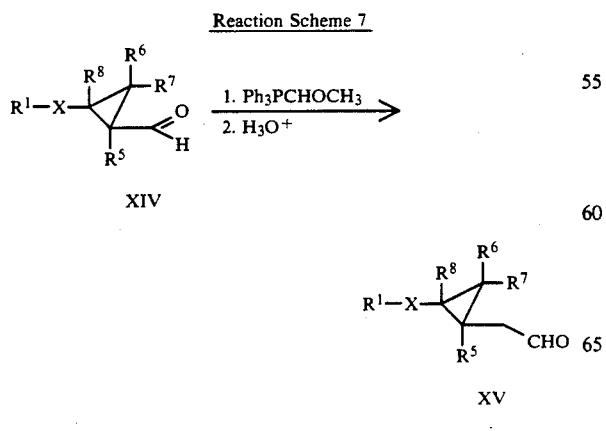

Reaction Scheme 7

LIPOXYGENASE INHIBITORY ACTIVITY OF THE COMPOUNDS OF THIS INVENTION

Compounds of the present invention are active inhibitors of 5-lipoxygenase and/or 12-lipoxygenase as demonstrated by the following data for representative compounds.

Assays to determine 5-lipoxygenase inhibitory activity were performed in 200 mL incubations containing the 20,000×g supernatant from 1.5 million homogenized RBL-1 cells and various concentrations of the test compound. Reactions were initiated by addition of radiolabeled arachidonic acid and terminated by acidification and ether extraction. Reaction products were separated from nonconverted substrate by thin layer chromatography and measured by liquid scintillation spectroscopy. All incubations were performed in triplicate. Inhibition of 5-lipoxygenase activity was calculated as the ratio of the amount of product formed in the presence and absence of inhibitor. IC50 values (concentration of compound producing 50% enzyme inhibition) were calculated by linear regression analysis of percentage inhibition versus log inhibitor concentration plots. (Dyer, R .D.; Haviv, F.; Hanel, A. M.; Bornemier, D. A.; Carter, G. W. Fed. Proc., Fed. Am. Soc. Exp. Biol. 1984, 43, 1462A). Results for compounds of the foregoing examples are indicated in Table 1.

TABLE 1

In Vitro Inhibitory Potencies of Compounds of this Invention Against 5-Lipoxygenase

| Example | IC50 ($10^{-6}$M) |
| --- | --- |
| 1a | 0.3 |
| 1b | 0.2 |
| 2 | 0.1 |
| 3 | 1.6 |
| 4 | 1.8 |
| 7 | 0.4 |
| 8 | 0.2 |
| 9 | 1.8 |
| 10 | 0.1 |
| 11 | 0.1 |
| 14 | 0.13 |
| 16 | 2.8 |
| 17 | 0.07 |
| 18 | 0.2 |
| 20 | 0.08 |
| 21 | 0.05 |
| 22 | 0.9 |
| 23 | 0.1 |
| 24 | 0.1 |
| 25 | 0.1 |
| 26 | 1.1 |
| 27 | 1.7 |
| 28 | 0.1 |
| 29 | 0.9 |
| 30 | 0.1 |
| 31 | 1.4 |
| 32 | 0.1 |
| 34 | 0.3 |
| 36 | 0.06 |
| 37 | 0.1 |
| 38 | 0.03 |
| 40 | 0.2 |
| 42 | 1.6 |
| 43 | 5.7 |
| 44 | 0.1 |
| 45 | 0.3 |
| 46 | 0.3 |
| 47 | 0.3 |
| 48 | 0.4 |
| 49 | 0.4 |
| 50 | 0.1 |
| 51 | 0.06 |
| 53 | 0.1 |
| 54 | 0.3 |
| 56 | 0.2 |

TABLE 1-continued

In Vitro Inhibitory Potencies of Compounds of this Invention Against 5-Lipoxygenase

| Example | IC50 ($10^{-6}$M) |
|---|---|
| 57 | 0.3 |
| 59 | 0.7 |
| 60 | 1.5 |
| 61 | 0.2 |
| 62 | 7.6 |
| 63 | 0.3 |
| 64 | 1.0 |
| 65 | 3.6 |
| 66 | 0.44 |
| 67 | 0.4 |

INHIBITION OF LEUKOTRIENE BIOSYNTHESIS

Inhibition of the biosynthesis of leukotrienes in vivo after oral administration of representative test compounds of this invention was determined using a rat peritoneal anaphylaxis model in a similar manner as that described by Young and coworkers (Young, P. R.; Dyer, R. D.; Carter, G. W. Fed. Proc., Fed. Am. Soc. Exp. Biol. 1985, 44, 1185). In this model rats were injected intraperitoneally (ip) with rabbit antibody to bovine serum albumin (BSA) and three hours later injected ip with BSA to induce an antgen-antibody response. Rats were sacrificed 15 minutes after this challenge and the peritoneal fluids were collected and analyzed for leukotriene levels. Test compounds were administered by gavage one hour prior to the antigen challenge. Percent inhibition values were determined by comparing the treatment group to the mean of the control group. The results of this assay, for representative compounds of the present invention, at an oral dose level of 200 mmol/kg are presented in Table 2, and at an oral dose of 100 mmol/kg in Table 3. Examination of these data demonstrate that compounds of this invention are orally effective in preventing the in vivo biosynthesis of leukotrienes.

TABLE 2

In vivo Leukotriene Inhibitory Activity of Compounds of this Invention

| Example | % Inhibition of Leukotrienes at 200 μmol/kg oral dose |
|---|---|
| 1 | 62 |
| 3 | 100 |
| 4 | 97 |
| 5 | 90 |
| 9 | 61 |
| 10 | 97 |
| 11 | 65 |
| 12 | 68 |
| 13 | 76 |
| 16 | 61 |
| 17 | 81 |
| 19 | 64 |
| 22 | 96 |
| 23 | 93 |
| 25 | 52 |
| 26 | 92 |
| 27 | 99 |
| 28 | 73 |
| 29 | 96 |
| 33 | 84 |
| 34 | 100 |
| 35 | 99 |
| 37 | 93 |
| 39 | 82 |
| 40 | 97 |

TABLE 2-continued

In vivo Leukotriene Inhibitory Activity of Compounds of this Invention

| Example | % Inhibition of Leukotrienes at 200 μmol/kg oral dose |
|---|---|
| 47 | 100 |

TABLE 3

In vivo Leukotriene Inhibitory Activity of Compounds of this Invention

| Example | % Inhibition of Leukotrienes at 100 μmol/kg oral dose |
|---|---|
| 166 | 91 |
| 167 | 94 |
| 168 | 99 |
| 169 | 98 |
| 170 | 94 |
| 174 | 96 |
| 176 | 87 |
| 178 | 60 |
| 179 | 61 |
| 180 | 85 |
| 188 | 97 |
| 189 | 73 |
| 192 | 71 |
| 193 | 93 |
| 194 | 97 |
| 198 | 90 |

INHIBITION OF LEUKOTRIENE BIOSYNTHESIS IN VITRO IN HUMAN WHOLE BLOOD

Inhibition of leukotriene biosynthesis was evaluated in an assay, involving calcium ionophore-induced $LTB_4$ biosynthesis expressed by human whole blood. Heparinized (20 U/mL) human blood (0.3 mL) was preincubated with test compound or vehicle for 15 min. at 37° C. Eicosanoid biosynthesis was initiated by adding calcium ionophore (A23187) in DMSO to a final concentration of 50 μM and terminated after 30 min. by rapid cooling of the blood in an ice bath and centrifuging at 3° C. for 10 min at 2500×g. The plasma was mixed with 4 volumes of methanol and allowed to stand for at least 30 min. at 3° C. prior to centrifuging at 1800×g for 10 min. The level of $LTB_4$ in aliquots of the methanol-plasma extract was analyzed by radio-immunoassay or enyme-immunoassay techniques. The compounds of this invention inhibit $LTB_4$ biosynthesis in human whole blood as illustrated in Table 4.

TABLE 4

Inhibition of $LTB_4$ Biosynthesis in Human Whole Blood.

| Example | Inhibition of Leukotriene Biosynthesis IC$_{50}$ (μM) |
|---|---|
| 160 | 0.47 |
| 161 | 0.17 |
| 162 | 0.25 |
| 163 | 0.25 |
| 164 | 0.61 |
| 165 | 0.74 |
| 166 | 0.11 |
| 167 | 0.04 |
| 168 | 0.05 |
| 169 | 0.17 |
| 170 | 89% at 0.1 μM |
| 171 | 40% at 0.39 μM |

TABLE 4-continued

Inhibition of LTB$_4$ Biosynthesis in Human Whole Blood.

| Example | Inhibition of Leukotriene Biosynthesis IC$_{50}$ (μM) |
|---|---|
| 172a | 0.96 |
| 173 | 0.23 |
| 174 | 0.14 |
| 175 | 0.2 |
| 176 | 0.17 |
| 177 | 69% at 0.2 μM |
| 178 | 64% at 0.2 μM |
| 179 | 61% at 0.2 μM |
| 180 | 0.69 |
| 181 | 0.6 |
| 182 | 0.69 |
| 183 | 0.62 |
| 184 | 0.85 |
| 185 | 0.24 |
| 186 | 0.47 |
| 187 | 0.21 |
| 188 | 0.32 |
| 189 | 0.68 |
| 190 | 0.2 |
| 191 | 0.83 |
| 192 | 1.2 |
| 193 | 0.23 |
| 194 | 0.37 |
| 195 | 0.19 |
| 196 | 0.98 |
| 197 | 1.6 |
| 198 | 0.97 |
| 199 | 0.06 |

The present invention also provides pharmaceutical compositions which comprise one or more of the compounds of formula I above formulated together with one or more non-toxic pharmaceutically acceptable carriers. The pharmaceutical compositions may be specially formulated for oral administration in solid or liquid form, for parenteral injection, for rectal or vaginal administration, or for topical, buccal, or nasal administration.

The pharmaceutical compositions of this invention can be administered to humans and other animals orally, rectally, parenterally (i.e. intravenously, intramuscularly, or subcutaneously), intracisternally, intravaginally, intraperitoneally, topically (as by powders, ointments, or drops), bucally, or as an oral or nasal spray.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous cariers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like, Prolonged absorption of the injectable pharmaceutical form may be brought about by the inclusion of agents which delay abdorption such as aluminum monostearate and gelatin.

If desired, and for more effective distribution, the compounds can be incorporated into slow release or targeted delivery systems such as polymer matrices, liposomes, and microspheres.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alignates, gelatin, polyvinylpyrrolidone, surcrose, and acacia, c) humectants such as glycerol, d) disintegrating agents such as agar-agar, calcium carbonate, potato ortapioca starch, alginic acid, certain silicates, and sodium carbonate, e) solution retarding agents such as paraffin, f) absorption accelerators such as quaternaryammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentione excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuranyl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 0.001 mg to about 100 mg, more preferably of about 0.01 mg to about 50 mg of active compound per kilogram of body weight per day are administered orally to a mammalian patient. If desired, the effective daily dose may be divided into multiple doses for purposes of administration, e.g. two to four separate doses per day.

The following preferred embodiments are for the purpose of illustrating the use of the processes to prepare representative compounds of this invention and do not limit the specification and claims in any way whatsoever.

EXAMPLE 1

N-(1-trans-(2-(benzo[b]thien-2-yl)cyclopropyl)ethyl)-N-hydroxyurea

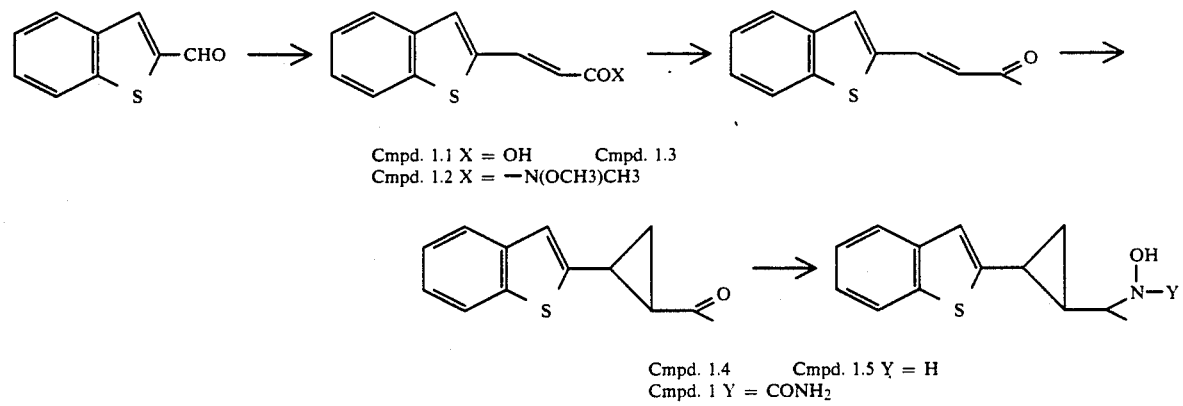

Cmpd. 1.1 X = OH      Cmpd. 1.3
Cmpd. 1.2 X = —N(OCH3)CH3

Cmpd. 1.4      Cmpd. 1.5 Y = H
Cmpd. 1 Y = CONH$_2$

To a solution of benzo[b]thiophene (11.49 g, 85.6 mmol) in 300 mls THF at $-78°$ C., was added n-butyllithium (36.0 mls of a 2.5M solution in hexanes, 89.9 mmol) dropwise and the mixture was stirred for 30 mins at $-78°$ C. N,N,-Dimethyl-formamide (6.57 g, 89.9 mmol) was added and the reaction was allowed to stir for 30 min. The cooling bath was then withdrawn and the reaction was allowed to warm to room temperature It was then diluted with saturated aqueous NH$_4$Cl (250 mL) and extracted with ethylacetate (3×250 mL). The organics were combined, dried with MgSO$_4$ and concentrated. The resulting residue was taken up in 20 mL ethanol and saturated aqueous NaHSO$_3$ (200 mL) was added. The resulting precipitate was collected and washed with ether. It was then dissolved in saturated aqueous Na$_2$CO$_3$ (200 mL) and the resulting aqueous solution was extracted with ethylacetate (3×200 mL). The organics were combined, dried with MgSO$_4$ and concentrated to afford 13.63 g (98%) of benzo[b]thien-2-ylcarboxaldehyde.

To a solution of benzo[b]thien-2-ylcarboxaldehyde (9.63 g, 59.4 mmol) and malonic acid (8.04 g, 77.3 mmol) in pyridine (45 mL) was added piperidine (1.01 g, 11.88 mmol). and the mixture was heated at reflux for 3.5 h, cooled to room temperature and poured into 100 mL 1:1 ice/conc. HCl. The precipitate was collected, dissolved in ethyl acetate, dried with MgSO$_4$ and then concentrated to afford intermediate, compound 1.1 (13.38 g).

To a suspension of compound 1.1 in CH$_2$Cl$_2$ (250 mL), was added oxalyl chloride (8.29 g, 65.34 mmol) followed by 2 drops of N,N-dimethylformamide. The reaction was stirred for 5 hours and then concentrated in vacuo. The resulting solid was taken up in fresh CH$_2$Cl$_2$ (250 mL) and cooled to 0∞C. N,O-dimethylhydroxylamine hydrochloride (6.37 g, 65.34 mmol) was added followed by the dropwise addition of pyridine (10.34 g, 130.7 mmol). The cooling bath was withdrawn and the reaction was allowed to warm to room temperature and then quenched with saturated aqueous NaHCO$_3$ (250 mL). The layers were separated and the aqueous was extracted with CH$_2$Cl$_2$ (2×250 mL). The organics were combined, dried with MgSO$_4$, and concentrated. The resulting residue was chromatographed (silica gel, ether:hexanes 1:1 to 7:3) to provide intermediate 1.2 (12.40 g, 85% over the three steps) as an off-white solid.

To a solution of intermediate 1.2 (6.00 g, 24.3 mmol) in THF (125 mL) at 0° C., was added methylmagnesium bromide (8.9 mL of a 3.0M solution in ether, 26.7 mmol) dropwise. Upon completion of addition, the cooling bath was removed and the reaction was allowed to warm to room temperature. It was then quenched with saturated aqueous NH4Cl (125 mL) and extracted with ethylacetate (3×125 mL). The organics were combined, dried with MgSO4 and concentrated to afford the intermediate ketone 1.3.

To a solution of trimethylsulfoxonium iodide (5.62 g, 25.52 mmol) in DMSO (50 mL), was added NaH (612 mg, 25.52 mmol) and the mixture was stirred for 15 min. A solution of compound 1.3 in DMSO (20 mL) was added dropwise. The reaction was stirred at room temperature for 2 h, then heated at 50° C. for 1 hr. The reaction was cooled to room temperature, diluted with brine (100 mL) and extracted with ethyl acetate (3×100 mL). The organics were combined, dried with MgSO4 and concentrated. The resulting residue was chromatographed (silica gel, ether:hexanes, 15:85) to afford intermediate 1.4 (2.15 g, 41% over the two steps).

A solution of intermediate 1.4 (2.14 g, 9.9 mmol) and hydroxylamine hydrochloride (757 mg, 10.9 mmol) in 1:1 ethanol:pyridine (50 mL) was stirred for 3 hours. It was then concentrated in vacuo. The resulting residue was taken up in brine (50 mL) and extracted with ethyl acetate (3×50 mL). The organics were combined, dried with MgSO4 and concentrated.

The resulting residue was taken up in ethanol (50 mL) and BH3.pyridine (2.02 g, 21.78 mmol) was added and the mixture was stirred for 30 min. Aqueous 6N HCl (3.96 mL, 23.76 mmol) was then added dropwise and the reaction was stirred until all evolution of gas ceased (1 hour). The reaction was neutralized with 2N NaOH and the precipitate was collected to afford 1.83 g (79%) of hydroxylamine 1.5a as a single diastereomer (higher $R_f$ by TLC, 1:1 ethylacetate:hexanes).

The filtrate was concentrated and the residue was taken up in brine (50 mL) and extracted with ethylacetate (3×50 mL). The organics were combined, dried with MgSO4 and concentrated. The resulting residue was chromatographed (silica gel, ether:hexanes, 1:1) to afford the other single diastereomer of structure 1.5b (lower $R_f$ by TLC, 1:1 ethylacetate:hexanes)

To a solution of compound 1.5a (1.83 g, 7.9 mmol) in THF (40 mL) was added trimethylsilylisocyanate (1.09 g, 9.48 mmol) and the reaction was stirred for 10 min. It was then diluted with aqu. sat'd NH4Cl (40 mL) and extracted with ethylacetate (3×40 mL). The organics were combined, dried with MgSO4 and concentrated. The resulting residue was crystallized in ethylacetate/hexanes to afford one diastereomer 1a of the desired product. m.p.=145°–147° C.; 1H NMR (300 MHz, DMSO-d6): 0.95–1.08 (m, 2H), 1.16 (d, 3H, J=6.5 Hz), 1.44–1.55 (m, 1H), 2.22 (m, 1H), 3.67 (m, 1H), 6.34 (bs, 2H), 7.06 (s, 1H), 7.21–7.33 (m, 2H), 7.66 (dd, 1H, J=1 Hz, J=8 Hz), 7.81 (dd, 1H, J=1 Hz, J=8 Hz), 9.04 (s, 1H); MS (M+H)+=277; Analysis calc'd for $C_{14}H_{16}N_2O_2S$: C, 60.84, H, 5.83, N, 10.14; Found: C, 60.66, H, 5.94, N, 9.84.

The other diastereomer 1 b of the desired product was prepare according to the previous procedure. m.p.=168.5°–169.5° C.; 1H NMR (300 MHz, DMSO-d6) 0.95 (m, 1H), 1.12 (m, 1H), 1.18 (d, 3H, J=7 Hz), 1.39 (m, 1H), 2.19 (m, 1H), 3.66 (m, 1H), 6.33 (bs, 2H), 7.00 (s, 1H), 7.28 (m, 2H), 7.68 (m, 1H), 7.83 (m, 1H), 9.06 (s, 1H); MS (M+H)+=277; Analysis calc'd for $C_{14}H_{16}N_2O_2S$: C, 60.84, H, 5.83, N 10.14; Found: C, 60.71; H, 5.85, N, 10.08.

EXAMPLE 2

N-(1-trans-(2-(4-phenoxyphenyl)cyclopropyl)ethyl)-N-hydroxyurea.

The title compound was prepared according to the procedure of Example 1, substituting 4-phenoxybenzaldehyde for benzo[b]thien-2-ylcarboxaldehyde. 1H NMR (300 MHz, DMSO-d6): 0.85 (t, 2H), 1.28–1.38 (m, 1H), 1.90–1.98 (m, 1H), 1.15 (d, 3H), 3.58–3.68 (m, 1H), 6.30 (s, 2H), 6.85–7.40 (m, 9H), 9.00 (s, 1H); MS (M+H)+=313; Analysis calc'd for $C_{18}H_{20}N_2O_3$: C, 69.21, H, 6.45, N, 8.97; Found: C, 69.16, H, 6.54, N, 8.55.

EXAMPLE 3

N-(1-trans-(2-phenylcyclopropyl)ethyl)-N-hydroxyurea

The title compound was prepared according to the procedure of Example 1, substituting trans-4-phenyl-3-buten-2-one for intermediate 1.3. m.p.=145°–147° C.; 1H NMR (DMSO-d6): 0.80–0.90 (m, 2H), 1.15 (d, 3H), 1.28–1.38 (m, 1H), 1.90–1.97 (m, 1H), 3.58–3.68 (m, 1H), 6.27 (s, 2H), 7.00–7.25 (m, 5H); Analysis calc'd for $C_{12}H_{15}N_2O_2$: C, 65.43, H, 7.32, N, 12.72; Found: C, 65.27, H, 7.33, N, 12.72.

EXAMPLE 4

N-1-(trans-(2-phenylcyclopropyl)methyl)-N-hydroxyurea.

The title compound was prepared according to the procedure of Example 1 substituting trans-2-phenylcyclopropylcarboxaldehyde for intermediate 1.4. m.p.=147°–148° C.; 1H NMR (300 MHz, DMSO-d6): 0.88 (m, 2H), 1.33 (m, 1H), 1.84 (m, 1H), 3.37 (dd, 2H, J=2 Hz, J=6.5 Hz), 6.27 (bs, 2H), 7.05 (m, 2H), 7.11 (m, 1H), 7.23 (m, 2H), 9.30 (s, 1H); MS: M+=206; Analysis calc'd for $C_{11}H_{14}N_2O_2$: C, 64.06, H, 6.84, N, 13.59; Found: C, 63.85, H, 6.84, N, 13.59.

EXAMPLE 5

N-(1-trans-(1-methyl-2-phenylcyclopropyl)ethyl)-N-hydroxyurea.

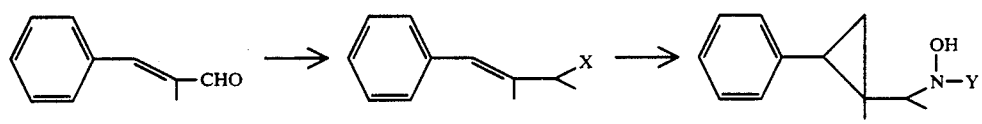

Cmpd. 5.1 X = OH     Cmpd. 5 Y = CONH2
Cmpd. 5.2 X = =O

To a solution of a-methylcinnamaldehyde (10.0 g, 68.4 mmol) in ether (250 mL) at 0∝C., was added methylmagnesium bromide (25.1 mL of a 3.0M solution in ether, 75.2 mmol) dropwise. Upon completion of addition, the reaction was stirred for 10 min at 0° C. and then quenched with saturated aqueous NH4Cl (250 mL) and extracted with ethylacetate (3×250 mL). The organics were combined, dried with MgSO4 and concentrated to provide the intermediate 5.1.

To a solution of oxalyl chloride (9.98 g, 78.7 mmol) in 200 mL CH2Cl2 at −78° C., was added dimethylsulfoxide (12.83 g, 164.2 mmol) dropwise and the mixture was stirred for 5 mins at −78∝C. A solution of the crude residue from above dissolved in 25 mL CH2Cl2 was added dropwise. Upon completion of addition, the reaction was stirred for 20 mins at −78° C. Triethylamine (34.5 g, 342 mmol) was added, the cooling bath was withdrawn and the reaction was allowed to warm to room temperature It was then diluted with brine (250 mL) and extracted with CH2Cl2 (3×250 mL). The organics were combined, dried with MgSO4 and concentrated. The resulting residue was chromatographed (silica gel, ether:hexanes, 3:97) to afford 9.64 g (88% over the 2 steps) of intermediate ketone 5.2.

The desired product 5 was prepared according to the procedure of Example 1 substituting intermediate 5.2 for intermediate 1.4. m.p.=67°-96° C., 1H NMR (300 MHz, DMSO-d6, mixture of diastereomers) 0.73 (d, 3H, J=3.5 Hz), 0.76 (m, 1H), 0.86 and 1.01 (dd, 1H, J=5 Hz, J=9 Hz), 1.14 (t, 3H, J=6.5 Hz), 2.01 and 2.26 (dd, 1H, J=6.5 Hz, J=9 Hz), 3.85 and 3.91 (q, 1H, J=7 Hz), 6.20 and 6.28 (bs, 2H), 7.11-7.20 (m, 3H), 7.22-7.30 (m, 2H), 8.90 and 8.94 (s, 1H); MS (M+H)+ =235; Analysis calc'd for C13H18N2O2: C, 66.64, H, 7.74, N, 11.96; Found: C, 66.11, H, 7.72, N, 11.83.

EXAMPLE 6

N-(1-trans-(2-(3-phenoxyphenyl)cyclopropyl)ethyl)-N-hydroxyurea.

The intermediate 6.1 was prepared according to the procedure of Example 1 substituting 3-phenoxybenzaldehyde for benzo[b]thein-2-ylcarboxaldehyde.

To a solution of trimethylsulfoxonium iodide (17.65 g, 80.2 mmol) in dimethylsulfoxide (250 mL) was added sodium hydride (1.92 g, 80.2 mmol) and the resulting mixture was stirred for 20 mins. The intermediate 6.1 (20.63 g, 72.9 mmol) was added and the reaction was stirred for 2 h at room temperature, then heated at 50° C. for 1 h. The reaction was cooled to room temperature, diluted with brine (250 mL) and extracted with ethyl acetate (3×250 mL). The organics were combined, dried with MgSO4 and concentrated. The resulting residue was purified by column chromatography (silica gel, ether:hexanes, 30:70) to provide 18.85 g (87%) of intermediate 6.2 as a colorless oil.

To a solution of 6.2 (3.22 g, 10.8 mmol) in THF (50 mL) at 0° C., was added methylmagnesium bromide (4.0 mL of a 3.0M solution in ether, 11.9 mmol). The cooling bath was withdrawn and the reaction was allowed to warm to room temperature It was then diluted with saturated aqueous NH4Cl (50 mL) and extracted with ethyl acetate (3×50 mL). The organics were combined, dried with MgSO4 and concentrated to afford intermediate ketone 6.3.

The desired product was prepared according to the procedure of Example 1 substituting intermediate 6.3 for 1.4. m.p.=132°-134° C.; 1H NMR (300 MHz, DMSO-d6, 85:15 mixture of diastereomers): 0.86 (t, 2H, J=7 Hz), 1.13 (d, 3H, J=7 Hz), 1.33 (m, 1H), 1.92 (m, 1H), 3.62 (m, 1H), 6.27 (bs, 2H), 6.71 (m, 2H), 6.82 (d, 1H, J=8 Hz), 6.99 (m, 2H), 7.09-7.25 (m, 2H), 7.39 (m, 2H), 8.98 and 9.00 (s, 1H); MS (M+H)+ =313; Analysis calc'd for C18H20N2O3: C, 69.21, H, 6.45, N, 8.97; Found: C, 68.91, H, 6.48, N, 8.98.

EXAMPLE 7

N-(1-trans-(2-(4-(1-phenylethoxy)phenyl)cyclopropyl)ethyl)-N-hydroxyurea.

To a solution of 4-hydroxybenzaldehyde (528 mg, 4.32 mmol) in dimethylsulfoxide (8 mL) was added potassium t-butoxide (558 mg, 4.97 mmol) and the mixture was stirred for 20 mins. 1-Bromoethylbenzene was added dropwise and the reaction was stirred for 1 hour at room temperature It was then poured into brine (8 mL) and extracted with ethyl acetate (3×10 mL). The organics were combined; dried with MgSO4 and concentrated. The resulting residue was chromatographed (silica gel, ether:hexanes, 15:85) to afford 930 mg (95%) of 4-(1-phenylethoxy)benzaldehyde as an oil.

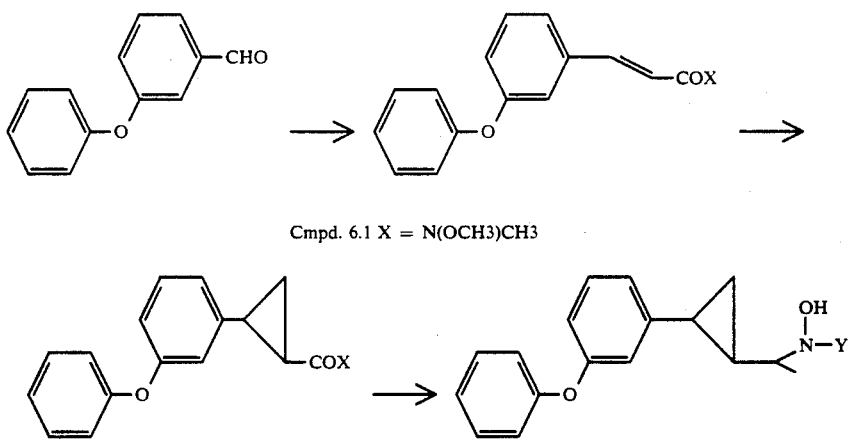

Cmpd. 6.1 X = N(OCH3)CH3

Cmpd. 6.2 X = N(OCH3)CH3
Cmpd. 6.3 X = CH3

Cmpd. 6.4 Y = H
Cmpd. 6 Y = CONH2

The desired product was prepared, as an oil according to the procedure of Example 1 substituting 4-(1-phenylethoxy)benzaldehyde for benzo[b]thien-2-ylcarboxaldehyde. 1H NMR (300 MHz, DMSO-d$_6$): 0.73 (m, 2H), 1.01 (d, 3H, J=6.5 Hz), 1.20 (m, 1H), 1.51 (d, 3H, J=6.5 Hz), 1.81 (1H, m), 3.56 (m, 1H), 5.41 (q, 1H, J=6.5 Hz), 6.25 and 6.55 (bs, 2H), 6.71-6.79 (m, 2H), 6.84-6.95 (m, 2H), 7.20-7.41 (m, 5H), 8.93 and 8.95 and 8.96 (s, 1H); MS (M+H)+ =341.

EXAMPLE 8

N-(1-trans-(2-(benzo[b]thien-2-yl)cyclopropyl)ethyl)-N-hydroxy-N'-methylurea

The title compound was prepared according to the procedure of Example 1 substituting methyl isocyanate for trimethylsilylisocyanate. m.p.=123.5°-126° C.; 1H NMR (300 MHz, DMSO-d$_6$, 1:1 ratio of diastereomers): 0.90-1.14 (m, 2H), 1.15 and 1.17 (d, 3H, J=4 Hz), 1.33-1.51 (m, 1H), 2.20 (m, 1H), 2.61 and 2.64 (d, 3H, J=5.5 Hz), 3.63 (m, 1H), 6.91 (m, 1H), 7.02 and 7.10 (s, 1H), 7.20-7.34 (m, 2H), 7.66 (m, 1H), 7.81 and 7.83 (d, 1H, J=3.5 Hz), 8.94 and 8.99 (s, 1H); MS (M+H)+ =291; Analysis calc'd for C$_{15}$H$_{18}$N$_2$O$_2$S: C, 62.04, H, 6.25, N, 9.65; Found: C, 62.25, H, 6.32, N, 9.62.

EXAMPLE 9

N-(1-cis-(2-phenylcyclopropyl)ethyl)-N-hydroxyurea

The title compound was prepared according to the procedure of Example 1 substituting cis-2-phenyl-1-cyclopropanecarboxylic acid (C. H. DePuy, G. M. Dappen, K. L. Eilers, R. A. Klein, JOC, 29, 2813, 1964) for intermediate 1.1. m.p.=120°-123° C.; 1H NMR (300 MHz, DMSO-d$_6$, 3:1 mixture of diastereomers): 0.72 and 0.86 (m, 1H), 0.77 and 0.99 (d, 3H, J=6.5 Hz), 1.02 (m, 1H), 1.29-1.48 (m, 1H), 2.07-2.24 (m, 1H), 3.35 (m, 1H), 6.04 and 6.25 (bs, 2H), 7.07-7.32 (m, 5H), 8.97 (s, 1H); MS (M+H)+ =221; Analysis calc'd for C$_{12}$H$_{16}$N$_2$O$_2$: C, 65.43, H, 7.32, N, 12.72; Found: C, 65.63, H, 7.38, N, 12.70.

EXAMPLE 10

N-(1-trans-(2-(3-phenoxyphenyl)cyclopropyl)methyl)-N-hydroxyurea

To a solution of intermediate 6.2 (8.09 g, 27.2 mmol) in THF (100 mL) at 0° C., was added diisobutylaluminum hydride (54.5 mL of a 1.0M solution in THF, 54.5 mmol) dropwise. Upon completion of addition, the reaction was stirred for 30 min at 0° C., then quenched with aqueous 10% HCl (100 mL). The cooling bath was withdrawn and the reaction was allowed to warm to room temperature It was then extracted with ethyl acetate (3×125 mL). The organics were combined, dried with MgSO$_4$ and concentrated. The resulting residue was chromatographed (silica gel, ether:hexanes, 1:9) to provide 4.78 g (74%) of the corresponding aldehyde intermediate 10.1 (structure 6.2 with X=H).

The title compound was prepared according to the procedure of Example 1 substituting the above aldehyde for intermediate 1.4. m.p.=81.5°-83.0° C.; 1H NMR (300 MHz, DMSO-d$_6$): 0.82-0.95 (m, 2H), 1.32 (m, 1H), 1.85 (m, 1H), under DMSO (2H), 6.27 (bs, 2H), 6.73 (m, 2H), 6.83 (d, 1H<J=8 Hz), 6.99 (m, 2H), 7.13 (t, 1H, J=7.5 Hz), 7.24 (t, 1H, J=7.5 Hz), 7.48 (m, 2H), 9.30 (s, 1H); MS (M+H)+ =299; Analysis calc'd for C$_{17}$H$_{18}$N$_2$O$_3$:C, 68.44, H, 6.08, N, 9.39; Found: C, 68.41, H, 6.11, N, 9.36.

EXAMPLE 11

N-(1-trans-(2-(3-phenoxyphenyl)cyclopropyl)methyl)-N-hydroxy-N'-methylurea

The title compound was prepared according to the procedure of Example 10 substituting methyl isocyanate for trimethylsilylisocyanate. m.p.=93°-95° C.; 1H NMR (300 MHz, DMSO-d$_6$): 0.88 (m, 2H), 1.30 (m, 1H),1.84 (m, 1H), 2.57 (d, 3H, J=5 Hz), 3.33 (2H, under DMSO), 6.72 (m, 2H), 6.83 (m, 2H), 6.99 (m, 2H), 7.13 (m, 1H), 7.23 (t, 1H, J=8 Hz), 7.38 (m, 2H), 9.21 (s, 1H); MS (M+H)+ =313; Analysis calc'd for C$_{18}$H$_{20}$N$_2$O$_3$: C, 69.21, H, 6.45, N, 8.97; Found: C, 68.88, H, 6.41, N, 8.95.

EXAMPLE 12

N-(1-trans-(2-benzo[b]thien-2-yl)cyclopropyl)methyl)-N-hydroxyurea

The title compound was prepared according to the procedure of Example 10 substituting intermediate 1.2 for 6.1. m.p.=163°-164° C. (with decomposition); 1H NMR (300 MHz, DMSO-d$_6$, 97:3 trans:cis): 0.96-1.11 (m, 2H), 1.47 (m, 1H), 2.18 (m, 1H), 3.40 and 4.18 (d, 2H, J=6.5 Hz), 6.32 and 6.41 (bs, 2H), 7.10 (s, 1H), 7.21-7.33 (m, 2H), 7.67 (m, 1H), 7.83 (d, 1H, J=8.5 Hz), 9.35 and 9.45 (s, 1H); MS (M+H)+ =263; Analysis calc'd for C$_{13}$H$_{14}$N$_2$O$_2$S: C, 59.52, H, 5.38, N, 10.68; Found: C, 59.84, H, 5.43, N, 10.61.

EXAMPLE 13

N-(1-trans-(2-benzo[b]thien-2-yl)cyclopropyl)methyl)-N-hydroxy-N-methylurea

The title compound was prepared according to the procedure of Example 12 substituting methylisocyanate for trimethylsilylisocyanate. m.p.=146.5°-150.0° C.; 1H NMR (300 MHz, DMSO-d$_6$, 99:1 trans:cis): 0.96-1.10 (m, 2H), 1.46 (m, 1H), 2.18 (m, 1H), 2.61 (d, 3H, J=5.5 Hz), 3.39 and 4.18 (d, 2H, J=6.5 Hz), 6.89 (q, 1H, J=5.5 Hz), 7.09 (s, 1H), 7.21-7.33 (m, 2H), 7.67 (m, 1H), 7.83 (d, 1H, J=7.5 Hz), 9.27 and 9.38 (s, 1H); MS (M+H)+ =277; Analysis calc'd for C$_{14}$H$_{16}$N$_2$O$_2$S: C, 60.84, H, 5.84, N, 10.14; Found: C, 60.63, H, 5.81, N, 10.10.

EXAMPLE 14

N-(1-trans-(2-(4-(phenylmethoxy)phenyl)cyclopropyl)ethyl)-N-hydroxyurea

The title compound was prepared according to the procedure of Example 7 substituting benzyl bromide for 1-bromoethylbenzene. m.p.=157°-162° C.; 1H NMR (300 MHZ, DMSO-d$_6$, 85:15 mixture of diastereomers): 0.75 (m, 1H), 0.90 (m, 1H), 1.13 (d, 3H, J=7 Hz), 1.16 (m, 1H), 1.76 and 1.87 (m, 1H), 3.58 (m, 1H), 5.06 (s, 2H), 6.27 (bs, 2H), 6.84-7.00 (m, 4H), 7.28-7.45 (m, 5H), 8.96 and 9.00 (s, 1H); MS (M+H)+ =327; Analysis calc'd for C$_{19}$H$_{22}$N$_2$O$_3$: C, 69.91, H, 6.80, N, 8.58; Found: C, 69.53, H, 6.79, N, 8.50.

EXAMPLE 15

N-(1-trans-(2-(6-methoxy-2-naphthyl)cyclopropyl)ethyl)-N-hydroxyurea

To a solution of 2-bromo-6-methoxynaphthalene (0.5 g, 2.11 mmol) in THF (10 mL) at −78° C., was added n-butyllithium (1.69 mL of a 2.5M in hexanes, 4.22 mmol) dropwise and the solution was stirred for 45 min at −78° C. N,N-dimethylformamide (0.31 g, 4.22 mmol)

was then added and the reaction was allowed to stir for 15 min at −78° C. The reaction was quenched with saturated aqueous NH4Cl(10 mL). This solution was extracted with ethyl acetate (3×10 mL). The organics were combined, dried with MgSO4 and concentrated. The resulting residue was chromatographed (silica gel, ether:hexanes, 15:85) afforded 345 mg (88%) of 6-methoxy-2-napthaldehyde as an off-white solid.

The title compound was prepared according to the procedure of Example 6 substituting 6-methoxy-2-napthaldehyde for 3-phenoxybenzaldehyde. m.p.=161°-165° C.; 1H NMR (300 MHz, DMSO-$d_6$, 85:15 mixture of diastereomers) 0.85-1.01 (m, 2H), 1.17 (d, 3H, J=6.5 Hz), 1.36-1.47 (m, 1H), 1.92 and 2.06 (m, 1H), 3.67 (m, 1H), 3.84 (s, 3H), 6.30 (bs, 2H), 7.10 (dd, 1H, J=2.5 Hz, J=9.0 Hz), 7.18 (dd, 1H, J=2 Hz, J=9 Hz), 7.23 (d, 1H, J=2.5 Hz), 7.47 and 7.50 (m, 1H), 7.69 (m, 2H), 8.98 and 9.03 (s, 1H); MS (M+H)+ =301; Analysis calc'd for $C_{17}H_{20}N_2O_4$: C, 67.98, H, 67.71, N, 9.33; Found: C, 67.65, H, 6.78, N, 9.21.

EXAMPLE 16

N-(1-cis-(2-phenylcyclopropyl)methyl)-N-hydroxyurea

The title compound was prepared according to the procedure of Example 10 substituting cis-1-N-methoxy-N-methylcarboxyamide-2-phenylcyclopropane for intermediate 6.2. m.p.=103.5°-105.0° C., 1H NMR (300 MHz, DMSO-$d_6$): 0.88-1.02 (m, 2H), 1.33-1.47 (m, 1H), 2.18 (m, 1H), 2.79 (dd, 1H, J=9.5 Hz, J=15 Hz), 3.15 (dd, 1H, J=5 Hz, J=14.5 Hz), 6.22 (bs, 2H), 7.14-7.31 (m, 5H), 9.21 (s, 1H); MS (M+H)+ =207; Analysis calc'd for $C_{11}H_{14}N_2O_2$: C, 64.06, H, 6.84, N, 13.59; Found: C, 64.16, H, 6.88, N, 13.59.

EXAMPLE 17

N-(1-trans-(2-(3-phenoxyphenyl)cyclopropyl)ethyl)-N-hydroxy-N'-methylurea

The title compound was prepared according to Example 6 substituting methyl isocyanate for trimethylsilylisoyanate. m.p.=97°-100° C.; 1H NMR (300 MHz, DMSO-$d_6$, 1:1 ratio of diastereomers) 0.77-1.00 (m, 2H), 1.12 (t, 3H, J=6 Hz), 1.19-1.35 (m, 1H), 1.81-1.94 (m, 1H), 2.55 and 2.60 (d, 3H, J=5 Hz), 3.57 (m, 1H), 6.64-6.88 (m, 4H), 6.99 (m, 2H), 7.13 (t, 1H, J=7.5 Hz), 7.23 (q, 1H, J=8.5 Hz), 7.39 (m, 2H), 8.89 and 8.92 (s, 1H); MS (M+H)+ =327; Analysis calc'd for $C_{19}H_{22}N_2O_3$: C, 69.91, H, 6.80, N, 8.58; Found: C, 69.67, H, 6.85, N, 8.54.

EXAMPLE 18

N-(1-trans-(2-(6-methoxy-2-naphthyl)cyclopropyl)methyl)-N-hydroxyurea

The title compound was prepared according to the procedure of Example 10 substituting trans-1-(6-methoxy-2-naphthyl)-N-methoxy-N-methylpropenamide for intermediate 6.1. m.p.=182.5°-183.5° C.; 1H NMR (300 MHz, DMSO-$d_6$): 0.96 (m, 2H), 1.42 (m, 1H), 1.97 (m, 1H), 3.41 (m, 2H), 3.85 (s, 3H), 6.29 (bs, 2H), 7.11 (dd, 1H, J=2.5 Hz, J=9.5 Hz), 7.18 (dd, 1H, J=1.5 Hz, J=9.5 Hz), 7.24 (d, 1H, J=2.5 Hz), 7.50 (bs, 1H), 7.71 (dd, 2H, J=7 Hz, J=9.5 Hz), 9.32 (s, 1H); MS (M+H)+ =287; Analysis calc'd for $C_{16}H_{18}N_2O_3$: C, 67.11, H, 6.34, N, 9.79; Found: C, 67.10, H, 6.35, N, 9.75.

EXAMPLE 19

N-(1-trans-(2-(4-(2-methyl-1-propyl)phenyl)cyclopropyl)-ethyl)-N-hydroxyurea

The title compound was prepared according to the procedure of Example 6 substituting 4-(2-methyl-1-propyl)benzaldehyde (P. F. Juby, W. R. Goodwin, T. W. Hudyms, R. A. Partyka, *J. Med. Chem.*, 1972, 15 (12), 1297) for 3-phenoxybenzaldehyde. m.p.=142.0°-146.5° C.; 1H NMR (300 MHz, DMSO-$d_6$, 48:52 ratio of diastereomers) 0.74-0.98 (m, 2H), 0.84 (d, 6H, J=6.5 Hz), 1.13 and 1.15 (d, 3H, J=6.5 Hz), 1.18-1.36 (m, 1H), 1.70-1.93 (m, 2H), 2.36 and 2.38 (d, 2H, J=7 Hz), 3.61 (m, 1H), 6.26 and 6.28 (bs, 2H), 6.91-7.03 (m, 4H), 8.97 and 9.00 (s, 1H); MS (M+H)+ =277; Analysis calc'd for $C_{16}H_{24}N_2O_2$: C, 69.53, H, 8.75, N, 10.14; Found: C, 69.40, H, 8.71, N, 10.09.

EXAMPLE 20

N-(1-trans-(2-(4-(2-methyl-1-propyl)phenyl)cyclopropyl)-methyl)-N-hydroxyurea

The title compound was prepared according to the procedure of Example 10 substituting trans-1-N-methoxy-N-methylcarboxyamide-2-{4-(2-methyl-1-propyl)phenyl}-cyclopropane for intermediate 6.2. m.p.=161.5°-164.0° C.; 1H NMR (300 MHz, DMSO-$d_6$) 0.78-0.91 (m, 2H), 0.84 (d, 6H, J=6.5 Hz), 1.30 (m, 1H), 1.70-1.84 (m, 2H), 2.38 (d, 2H, J=6.5 Hz), 3.35 (d, 2H, J=6.5 Hz), 6.26 (bs, 2H), 6.98 (dd, 4H, J=8 Hz, J=9.5 Hz), 9.29 (s, 1H); MS (M+H)+ =263; Analysis calc'd for $C_{15}H_{22}N_2O_2$: C, 68.67, H, 8.45, N, 10.68; Found: C, 68.56, H, 8.47, N, 10.63.

EXAMPLE 21

N-(1-trans-(2-(4-(phenylmethoxy)phenyl)cyclopropyl)-methyl)-N-hydroxyurea

The title compound was prepared according to the procedure of Example 10 substituting trans-2-(4-benzyloxyphenyl)-1-(N-methoxy-N-methylcarboxyamide)-cyclopropane for intermediate 6.2. m.p.=172.5°-173.5° C.; 1H NMR (300 MHz, DMSO-$d_6$): 0.80 (m, 2H), 1.24 (m, 1H), 1.79 (m, 1H), 3.33 (2H, under DMSO/H2O), 5.05 (s, 2H), 6.27 (s, 2H), 6.87 (m, 2H), 6.98 (m, 2H), 7.28-7.45 (m, 5H), 9.28 (s, 1H); MS (M+H)+ =313; Analysis calc'd for $C_{18}H_{20}N_2O_3$: C, 69.21, H, 6.45, N, 8.97; Found: C, 68.65, N, 6.43, N, 8.98.

EXAMPLE 22

N-(1-trans-(2-(4-methoxyphenyl)cyclopropyl)ethyl)-N-hydroxyurea

The title compound was prepared according to the procedure of Example 1 substituting 4-methoxybenzaldehyde for benzo[b][thien-2-ylcarboxaldehyde. m.p.=129°-133° C.; 1H NMR (500 MHz, DMSO-$d_6$, 40:60 mixture of diastereomers): 0.77 and 0.91 (m, 2H), 1.14 (d, 3H, J=7.5 Hz), 1.17 and 1.25 (m, 1H), 1.76 and 1.87 (m, 1H), 3.60 (m, 1H), 3.69 and 3.71 (s, 3H), 6.25 (m, 2H), 6.79 (m, 2H), 6.98 (m, 2H), 8.95 and 8.98 (s, 1H); MS (M+H)+ =251; Analysis calc'd for $C_{13}H_{18}N_2O_3$: C, 62.38, H, 7.25, N, 11.20; Found: C, 62.44, H, 7.29, N, 11.03.

EXAMPLE 23

N-(1-trans-(2-(4-(1-phenylethoxy)phenyl)cyclopropyl)-methyl)-N-hydroxyurea

The title compound was prepared according to the procedure of Example 10 substituting trans-2-(4-(1-phenylethoxy)phenyl))cyclopropyl)-1-N-methoxy-N-methylcarboxylamide for intermediate 6.2. m.p.=109°-114° C.; 1H NMR (500 MHz, DMSO-d$_6$): 0.76 (m, 2H), 1.20 (m, 1H), 1.51 (d, 3H, J=6.5 Hz), 1.72 (p, 1H), 3.25-3.38 (m, 2H), 5.41 (q, 1H, J=6 Hz), 6.21 (s, 2H), 6.76 (d, 2H, J=9 Hz), 6.88 (m, 2H), 7.23 (m, 1H), 7.32 (t, 2H, J=8 Hz), 7.38 (d, 2H, J=8 Hz), 9.24 (s, 1H); MS (M+H)+ =327; Analysis calc'd for C$_{19}$H$_{22}$N$_2$O$_3$: C, 69.91, H, 6.80, N, 8.58; Found: C, 70.33, H, 6.89, N, 8.66.

EXAMPLE 24

N-(1-trans-((3,3-dimethyl-2-phenylcyclopropyl)ethyl)-N-hydroxyurea

Compound 24.1       Compound 24
Y = CONH$_2$

To a solution of S,S-diisopropyl-N-(p-tolylsulfonyl)-sulfoximine (911 mg, 3.01 mmol, Johnson et al. JACS, 1973, 95(13), 4287) in THF (15 mL) at −78∞C, was added n-butyllithium (1.20 mL of a 2.5M solution in hexanes, 3.01 mmol). Upon completion of addition, the reaction was stirred for 5 min at −78∞C, then brought to room temperature Trans-4-phenyl-3-butene-2-one (419 mg, 2.86 mmol) as a solution in THF (0.5 mL) was added and the reaction was stirred for 4 h. It was then diluted with aqu. sat'd NH4Cl (20 mL) and extracted with ethylacetate (3×20 mL). The organics were combined, dried with MgSO$_4$ and concentrated. The resulting residue was chromatographed (silica gel, hexane:ether, 97:3) to afford 175 mg (33%) of intermediate 24.1 as an oil.

The desired product was prepared according to the procedure of Example 1 substituting intermediate Compound 24.1 for Compound 1.4. m.p.=152°-155° C.; 1H NMR (300 MHz, DMSO-d$_6$): 0.73 (s, 3H), 1.16 (d, 3H, J=7 Hz), 1.21 (s, 3H), 1.34 (dd, 1H, J=6 Hz, J=10.5 Hz), 1.69 (d, 1H, J=6 Hz), 3.90 (m, 1H), 6.23 (bs, 2H), 7.11-7.30 (m, 5H), 9.01 (s, 1H); MS (M+H)+ =249; Analysis calc'd for C$_{14}$H$_{20}$N$_2$O$_2$: C, 67.71, H, 8.12, N, 11.28; Found: C, 67.24, H, 8.08, N, 11.18.

EXAMPLE 25

N-(1-trans-((3,3-dimethyl)-2-(4-(1-phenylethoxy)-phenyl)-cyclopropyl)ethyl)-N-hydroxyurea According to the procedure of Example 24 substituting trans-N-methyl-N-methoxy-3-(4-(1-phenylethoxy)-phenyl)-2-propenamide for trans-4-phenyl-3-butene-2-one the corresponding dimethylcyclopropyl intermediate 25.1 was prepared.

According to the procedure of Example 10 substituting trans-1-(N-methyl-N-methoxyacetamide)-3,3'-dimethyl-2-(4-(1-ethoxyphenyl)phenyl)cyclopropane (25.1) for intermediate 6.2. 1H NMR (300 MHz, DMSO-d$_6$, mixture of diastereomers): 0.70 (s, 3H), 1.15 (s, 3H), 1.16-1.24 (m, 1H), 1.52 (d, 3H, J=6.5 Hz), 1.58 (d, 1H, J=5.5 Hz), 3.37-3.56 (m, 2H). 5.42 (q, 1H, J=6.5 Hz), 6.26 (bs, 2H), 6.77 (m, 2H), 6.98 (m, 2H), 7.21-7.41 (m, 5H), 9.22 and 9.23 (s, 1H); MS (M+H)+ =355.

EXAMPLE 26

N-(1-trans-((5-methylfuran-2-yl)cyclopropyl)ethyl)-N-hydroxyurea

The title compound was prepared, as an oil, according to the procedure of Example 1 substituting 5-methyl-2-furfural for benzo[b]thien-2ylcarboxaldehyde. 1H NMR (300 MHz, DMSO-d$_6$, mixture of diastereomers): 0.72-0.93 (m, 2H), 1.11 and 1.13 (d, 3H, J=6.5 Hz), 1.24-1.42 (m, 1H), 1.74-1.89 (m, 1H), 2.17 and 2.18 (s, 3H), 3.57 (m, 1H), 5.86 (m, 2H), 6.28 (bs, 2H), 9.00 and 9.01 (s, 1H); MS (M+H)+ =22.

EXAMPLE 27

N-(1-trans-(2-phenylcyclopropyl)methyl)-N-hydroxyacetamide

To a solution of N-(1-trans-(2-phenylcyclopropyl)-methyl)-N-hydroxylamine (14.7 mmol) in CH$_2$Cl$_2$ (70 mL) was added acetic anhydride (3.29 g, 32.2 mmol) and triethylamine (3.56 g, 35.28 mmol) followed by a crystal of 4-N,N-dimethylaminopyridine and the reaction was stirred for 18 h. It was then diluted with brine (70 mL) and the layers were separated and the aqueous extracted with CH$_2$Cl$_2$ (2×70 mL). The organics were combined, dried with MgSO$_4$ and concentrated. The resulting residue was taken up in methanol (70 mL) and to this was added potassium carbonate (2.03 g, 14.7 mmol) and the suspension was stirred for 15 min, then decanted and the filtrate concentrated. The resulting residue was chromatographed (silica gel, ether:hexanes, 8:2, followed by ether:methanol, 8:2 ) to afford the desired product as an oil. 1H NMR (500 MHz, DMSO-d$_6$): 0.91 (m, 2H), 1.35 (m, 1H), 1.86 (m, 1H), 1.98 (s, 3H), 3.53 (d, 2H, J=6.5 Hz), 7.04 (m, 2H), 7.12 (m, 1H), 7.24 (m, 2H), 9.77 (bs, 1H); MS (M+H)+ =206;

EXAMPLE 28

N-(1-trans-(2-(benzo[b]thien-2-yl)cyclopropyl)ethyl)-N-hydroxyacetamide

The title compound was prepared according to the procedure of Example 27 substituting intermediate 1.5 for N-(1-trans-(2-phenylcyclopropyl)methyl)-N-hydroxylamine. m.p.=111-119∞C; 1H NMR (500 MHz, DMSO-d$_6$, 70:30 ratio of diastereomers): 0.95-1.13 (m, 2H), 1.20 and 1.24 (d, 3H, J=6.5 Hz), 1.43 and 1.49 (m, 1H), 2.01 (s, 3H), 2.15 and 2.27 (m, 1H), 4.00 (m, 1H), 7.05 and 7.11 (s, 1H), 7.22-7.33 (m, 2H), 7.67 (t, 1H, J=9 Hz), 9.52 and 9.55 (bs, 1H); MS (M+H)+ =276; Analysis calc'd for C$_{15}$H$_{17}$NO$_2$S:

C,65.42, H, 6.22, N, 5.09; Found: C, 65.45, H, 6.30, N, 5.08.

EXAMPLE 29

N-(1-trans-(2-(4-methoxyphenyl)cyclopropyl)ethyl)-N-hydroxyacetamide

The title compound was prepared, as a wax, according to the procedure of Example 27 substituting N-(1-trans-(2-(4-methoxphenyl)cyclopropyl)ethyl)-N-hydroxylamine for N-(1-trans-(2-phenylcyclopropyl)-methyl)-N-hydroxylamine. 1H NMR (300 MHz, DMSO-d$_6$, a mixture of diastereomers containing 17% of the cis isomer): 0.84 (m, 2H), 1.18 (bd, 3H, J=7 Hz), 1.26 (m, 1H), 1.81 (m, 1H), 1.91 and 1.98 and 2.00 (s, 3H), 3.70 and 3.71 (s, 3H), 3.93 (m, 1H), 6.76–6.83 (m, 2H), 6.92–7.01 (m, 2H), 9.48 and 9.52 and 9.60 and 9.63 (s, 1H); MS (M+H)+ =250; Calc'd for $C_{14}H_{19}NO_3$: C, 67.45, H, 7.68, N, 5.62; Found: C, 67.77, H, 7.79, N, 5.39.

EXAMPLE 30

N-methyl-N-hydroxy-trans-2-(3-phenoxyphenyl)cyclopropyl)carboxamide

To a solution of trans-2-(3-phenoxyphenyl)cyclopropanal (1.78 g, 7.47 mmol) in ethanol (30 mL) was added AgNO3 (2.95 g, 17.42 mmol) as a solution in water (3 mL). To this was added KOH (5.23 g, 93.3 mmol) as a solution in water (30 mL), and the resulting heterogeneous mixture was stirred for 2 h. The solution was then decanted and the silver salts washed with water (3×10 mL). The aqueous solutions were combined and washed with ether (2×30 mL). They were then acidified to pH2 by the addition of conc. HCl. The resulting acidic solution was extracted with ethylacetate (3×40 mL). The organics were combined, dried with MgSO4 and concentrated to afford trans-2-(4-phenoxyphenyl)cyclopropyl carboxylic acid as a crude oil which was used directly as follows.

The crude product from above was taken up in CH$_2$Cl$_2$ (35 mL) and oxalyl chloride was added followed by one drop of N,N-dimethylformamide. The reaction was stirred until all evolution of gas ceased (1 hour). It was then concentrated and the residue was taken up in 15 mL CH$_2$Cl$_2$ and added dropwise to a solution of N-methylhydroxylamine hydrochloride (1.87 g, 22.4 mmol) and triethylamine (6.04 g, 59.8 mmol) in 8 mL 1:1 THF:H20 at 0∞C. The reaction was stirred for 2 h at 0∞C, then brought to room temperature and concentrated. The resulting residue was purified by column chromatography (silica gel, ether:hexane, 90:10) to afford the desired product as an oil. 1H NMR (300 MHz, DMSO-d$_6$): 1.28 (m, 1H), 1.37 (m, 1H), 2.28 (m, 1H), 3.12 (bs, 3H), 6.77 (m, 1H), 6.85 (m, 1H), 6.92–7.01 (m, 3H), 7.13 (m, 1H), 7.27 (t, 1H, J=8 Hz), 7.39 (m, 2H), 10.02 (bs, 1H); MS (M+H)+ =284.

EXAMPLE 31

N-methyl-N-hydroxy-trans-2-phenylcyclopropyl carboxamide

The title compound was prepared according to the procedure of example 30 substituting 2-phenylcyclopropyl carboxylic acid for trans-2-(3-phenoxyphenyl)cyclopropyl carboxylic acid. m.p.=101.0°–102.5° C.; 1H NMR (500 MHz, DMSO-d$_6$): 1.27 (m, 1H), 1.38 (m, 1H), 2.27 (m, 1H), 2.50 (m, 1H), 3.13 (s, 3H), 7.16 (m, 3H), 7.27 (m, 2H), 9.97 (bs, 2H); MS (M+H)+ =192;

Analysis calc'd for $C_{11}H_{13}NO_2$: C, 69.09, H, 6.85, N, 7.33; Found: C, 69.27, H, 6.94, N, 7.30.

EXAMPLE 32

N-(1-trans-(2(2-phenylethyl)cyclopropyl)ethyl)-N-hydroxyurea

A solution of dihydrocinnamaldehyde (6.73 g, 50.2 mmol) and (carboethoxymethylene)triphenylphosphorane (17.84 g, 50.2 mmol) in toluene (250 mL) was refluxed for 18 h. It was then cooled to r.t. and concentrated in vacuo. The residue was taken up in ether (250 mL) and the triphenylphosphine oxide was filtered off. The filtrate was concentrated to afford the intermediate trans-ethyl-(5-phenyl)-2-pentenoate (32.1).

A solution of the intermediate 32.1 from above in 1:1 aqueous 1N LiOH:THF (250 mL) was refluxed for 18 h. It was then cooled to room temperature and washed with ethylacetate (2×200 mL). The aqueous was acidified to pH2 by the addition of conc. HCl, and extracted with ethylacetate (3×200 mL). These last organic extracts were combined, dried with MgSO4 and concentrated to afford the intermediate trans-5-phenyl-2-pentenoic acid (32.2).

The intermediate 32.2 was converted to trans-N-methoxy-N-methyl--5-phenyl-2-propenamide (32.3) and this intermediate was converted to the desired product according to the procedure of Example 6 substituting intermediate 32.2 for intermediate 6.1. m.p.=97°–106° C.; 1H NMR (300 MHz, DMSO-d$_6$, 2:1 ratio of diastereomers): 0.18 and 0.27 and 0.45 (m, 2H), 0.58 and 0.79 (m, 2H), 1.08 (d, 3H, J=7 Hz), 1.39 and 1.57 (m, 2H), 2.64 (m, 2H), 3.28–3.45 (m, 1H), 6.22 and 6.27 (bs, 2H), 7.11–7.30 (m, 5H), 8.91 and 8.92 (s, 1H); MS (M+H)+ =249; Analysis calc'd for $C_{14}H_{20}N_2O_2$: C, 67.71, H, 8.12, N, 11.28; Found: C, 67.81, H, 8.06, N, 11.34.

EXAMPLE 33

N-(1-trans-(2-(2-phenylethyl)cyclopropyl)methyl)-N-hydroxyurea

The title compound was prepared according to the procedure of Example 10 substituting trans-1-N-methoxy-N-methylcarboxyamide-2-(phenethyl)cyclopropane (32.3) for intermediate 6.2. 1H NMR (300 MHz, DMSO-d$_6$): 0.24 (m, 1H), 0.34 (m, 1H), 0.63 (m, 1H), 0.82 (m, 1H), 1.47 (q, 2H, J=6.5 Hz), 2.64 (m, 2H), 3.18 (d, 2H, J=7 Hz), 6.25 (bs, 2H), 7.12–7.30 (m, 5H), 9.19 (s, 1H); MS (M+H)+ =235; Analysis calc'd for $C_{13}H_{18}N_2O_2$: C, 66.64, H, 7.74, N, 11.96; Found: C, 66.33, H, 7.69, N, 11.95.

EXAMPLE 34

N-(2-trans-(2-phenylcyclopropyl)ethyl)-N-hydroxyurea

To a solution of (methoxymethyl)triphenylphosphonium chloride (9.25 g, 27 mmol) in THF (125 mL) at 0∞C, was added n-butyllithium (10.8 mL of a 2.5M solution in hexanes, 27 mmol) and the resulting red solution was stirred for 15 min at 0° C. Trans2-phenylcyclopropylcarboxaldehyde (3.58 g, 24.5 mmol), as a solution in 10 mL THF, was added dropwise and the reaction was stirred for 15 min. The mixture was quenched with aqueous sat'd NH4Cl (120 mL) and extracted with ethylacetate (3×120 mL). The organics were combined, dried with MgSO4 and concentrated. The resulting residue was taken up in 1:1 aqueous 10%

HCl:THF (120 mL) and stirred for 18 h at room temperature It was then diluted with brine (40 mL) and extracted with ethylacetate (3×100 mL). The organics were combined, dried with MgSO4 and concentrated. The resulting residue was chromatographed (silica gel, ether:hexanes, 5:95) to afford trans-(2-(2-phenylcyclopropyl)ethyl)acetaldehyde (34.1) (1.62 g, 46%).

The title compound was prepared according to the procedure of Example 1 substituting intermediate 34.1 for intermediate 1.4. m.p.=114°–117° C.; 1H NMR (300 MHz, DMSO-d6); 0.73–0.87 (m, 2H), 1.02 (m, 1H), 1.47–1.71 (m, 3H), 3.41 (m, 2H), 6.24 (bs, 2H), 7.02–7.14 (m, 3H), 7.22 (m, 2H), 9.20 (s, 1H); MS (M+H)+=221; Analysis calc'd for $C_{12}H_{16}N_2O_2$: C, 65.43, H, 7.32, N, 12.72; Found: C, 65.11, H, 7.27, N, 12.69.

EXAMPLE 35

N-(1-trans-(2-(4-bromophenyl)cyclopropyl)methyl)-N-hydroxyurea

The title compound was prepared according to the procedure of Example 10 substituting trans-(2-(4-bromophenyl)cyclopropyl)-1-N-methoxy-N-methylcarboxyamide for intermediate 6.2. m.p.=130°–131° C.; 1H NMR (300 MHz, DMSO-d6): 0.90 (m, 2H), 1.32 (m, 1H), 1.85 (m, 1H), 3.36 (m, 2H), 6.28 (bs, 2H), 7.02 (m, 2H), 7.41 (m, 2H), 9.30 (s, 1H); MS (M+H)+=285; Analysis calc'd for $C_{11}H_{13}BrN_2O_2$: C, 46.33, H, 4.59, N, 9.83; Found: C, 46.19, H, 4.63, N, 9.73.

EXAMPLE 36

N-(1-trans-(2-(4-phenoxyphenyl)cyclopropyl)methyl)-N-hydroxyurea

The title compound was prepared according to the procedure of Example 10 substituting trans-2-(4-phenoxyphenyl)cyclopropyl-1-N-methoxy-N-methylcarboxyamide for intermediate 6.2. m.p.=160.0°–161.5° C.; 1H NMR (300 MHz, DMSO-d6): 0.87 (m, 2H), 1.31 (m, 1H), 1.85 (m, 1H), 3.37 (m, 1H), 6.28 (bs, 2H), 6.87–6.98 (m, 4H), 7.09 (m, 3H), 7.36 (m, 2H), 9.30 (s, 1H); MS (M+H)+=299; Analysis calc'd for $C_{17}H_{18}N_2O_3$; C, 68.44, H, 6.08, N, 9.39; Found: C, 68.52, H, 6.04, N, 9.35.

EXAMPLE 37

N-(1-trans-(2-(4-bromophenyl)cyclopropyl)ethyl)-N-hydroxyurea

The title compound was prepared according to the procedure of Example 6 substituting 4-bromobenzaldehyde for 3-phenoxybenzaldehyde. m.p.=128°–130° C.; 1H NMR (300 MHz, DMSO-d6, 1:1 ratio of diastereomers): 0.87 and 0.99 (m, 2H), 1.13 (dd, 3H, J=6 Hz, J=7.5 Hz). 1/18–1.38 (m, 1H), 1.85 and 1.92 (m, 1H), 3.62 (m, 1H), 6.29 (bs, 2H), 7.01 (m, 2H), 7.40 (m, 2H), 8.98 and 9.02 (s, 1H); MS (M+H)+=299; Analysis calc'd for $C_{12}H_{15}BrN_2O_2$: C, 48.17, H, 5.05, N, 9.37; Found: C, 49.09, H, 5.37, N, 9.01.

EXAMPLE 38

N-(1-trans-(2-(4-bromophenyl)cyclopropyl)methyl)-N-hydroxyacetamide

The title compound was prepared according to the procedure of Example 27 substituting N-(1-trans-(2-(4-bromophenyl)cyclopropyl)methyl)-N-hydroxylamine for N-(1-trans-(2-phenylcyclopropyl)methyl)-N-hydroxylamine. m.p.=100°–102° C.; 1H NMR (300 MHz, DMSO-d6): 0.93 (m, 2H), 1.34 (m, 1H), 1.87 (m, 1H), 1.99 (s, 3H), 3.52 (m, 2H), 7.02 (m, 2H), 7.41 (m, 2H), 9.81 (bs, 1H); MS (M+H)+=284; Analysis calc'd for $C_{12}H_{14}BrNO_2$: C, 50.72, H, 4.97, N, 4.93; Found: C, 51.00, H, 5.00, N, 4.92.

EXAMPLE 39

N-(1-trans-(2-(4-methylphenyl)cyclopropyl)ethyl)-N-hydroxyurea

The title compound was prepared according to the procedure of Example 6 substituting 4-methylbenzaldehyde for 3-phenoxybenzaldehyde. m.p.=128°–130° C.; 1H NMR (300 MHz, DMSO-d6, 86:14 mixture of diastereomers): 0.81 and 0.93 (m, 2H), 1.12 and 1.14 (d, 3H, J=7 Hz), 1.28 (m, 1H), 1.88 (m, 1H), 2.23 (s, 3H), 3.61 (m, 1H), 6.27 (bs, 2H), 6.92 (m, 2H), 7.02 (m, 2H), 8.95 and 9.00 (s, 1H); MS (M+H)+=235; Analysis calc'd for $C_{13}H_{18}N_2O_2$: C, 66.64, H, 7.74, N, 11.96; Found: C, 66.57, H, 7.86, N, 11.78.

EXAMPLE 40

N-(1-trans-(2-(2-phenoxyphenyl)cyclopropyl)methyl)-N-hydroxyurea

To a solution of 2-phenoxybenzoic acid (10.00 g, 46.7 mmol) in THF (250 mL) was added dropwise borane.-dimethylsulfide (9.8 mL of a 10.0M solution, 98 mmol). Upon completion of addition, the reaction was stirred for 15 hrs. It was then quenched with aqueous 10% HCl (250 mL) and extracted with ethylacetate (3×250 mL). The organics were combined, dried with MgSO4 and concentrated to afford crude 2-phenoxybenzyl alcohol.

To a solution of oxalyl chloride (6.82 g, 53.71 mmol) in CH2Cl2 (250 mL) at −78° C., was added dimethylsulfoxide (8.76 g, 112.1 mmol) dropwise. The mixture was stirred for 5 mins. A solution of crude 2-phenoxybenzyl alcohol from above in CH2Cl2 (20 mL) was added dropwise. Upon completion of addition, the reaction was stirred for 20 mins at −78∞C. Triethylamine (23.58 g, 233.5 mmol) was then added dropwise. The cooling bath was removed and the reaction allowed to warm to room temperature It was then diluted with brine (250 mL). The layers were separated and the aqueous was extracted with CH2Cl2 (2×250 mL). The organics were combined, dried with MgSO4 and concentrated. The resulting residue was chromatographed (silica gel, ether:hexanes, 20:80) to afford 7.65 g (83% over the two steps) of 2-phenoxybenzaldehyde as a pale yellow oil.

The title compound was prepared, as an oil, according to the procedure of Example 10 substituting 2-phenoxy-benzaldehyde for 3-phenoxybenzaldehyde. 1H NMR (300 MHz, DMSO-d6):0.85 (m, 2H), 1.36 (m, 1H), 1.90 (m, 1H), 3.20 (m,2H), 6.24 (bs, 2H), 6.90 (m, 3H), 6.98-7.21 (m, 4H), 7.35 (m, 2H), 9.24 (s, 1H); MS (M+H)+=299; Analysis calc'd for $C_{17}H_{18}N_2O_3$: C, 68.44, H, 6.08, N, 9.32; Found: C, 67.79, H, 6.09, N, 9.32.

EXAMPLE 41

N-(1-trans-((3,3-dimethyl)-2-(3-phenoxyphenyl)cyclopropyl)-methyl)-N-hydroxyurea According to the procedure of Example 24 substituting trans-N-methyl-N-methoxy-3-(3-phenoxyphenyl)-2-propenamide for trans-4-phenyl-3-butene-2-one the corresponding dimethylcyclopropyl intermediate 41.1 was prepared.

According to the procedure of Example 10 substituting trans-1-(N-methyl-N-methoxyacetamide)-3,3'-dimethyl-2-(3-phenoxyphenyl)cyclopropane (41.1) for intermediate 6.2. 1H NMR (300 MHz, DMSO-d$_6$): 0.77 (s, 3H), 1.18 (s, 3H), 1.32 (q, 1H, J=6.5 Hz), 1.73 (d, 1H, J=6.5 Hz), 3.49 (m, 2H), 6.27 (bs, 2H), 6.79 (m, 2H), 6.94–7.00 (m, 3H), 7.12 (m, 1H), 7.27 (t, 1H, J=8.5 Hz), 7.38 (m, 2H), 9.27 (s, 1H); MS (M+H)+327; Analysis calc'd for C$_{19}$H$_{22}$N$_2$O$_3$: C, 69.91, H, 6.80, N, 8.58; Found: C, 69.78, H, 6.79, N, 8.82.

EXAMPLE 42

N-(1-trans-(2-(3-pyridyl)cyclopropyl)methyl-N-hydroxyurea

The title compound was prepared according to the procedure of Example 10 substituting trans-2-(3-pyridyl)cyclopropyl-1-N-methoxy-N-methylcarboxyamide for intermediate 6.2. m.p.=157°–159° C.; 1H NMR (300 MHz, DMSO-d$_6$, 99:1 trans:cis): 0.96 (t, 2H, J=7 Hz), 1.38 (m, 1H), 1.88 (m, 1H), 3.39 (m, 2H), 6.19 and 6.31 (bs, 2H), 7.25 m (dd, 1H, J=5 Hz, J=8.5 Hz), 7.39 (m, 1H), 8.33 (dd, 1H, J=1.5 Hz, J=5 Hz), 8.38 (d, 1H, J=2.5 Hz), 9.21 and 9.33 (s, 1H); MS (M+H)+=208; Analysis calc'd for C$_{10}$H$_{13}$N$_3$O$_2$: C, 57.96, H, 6.32, N, 20.28; Found: C, 57.50, H, 6.37, N, 19.98.

EXAMPLE 43

N-(1-trans-(2-(4-pyridyl)cyclopropyl)methyl)-N-hydroxyurea

The title compound was prepared according to the procedure of Example 10 substituting trans-2-(4-pyridyl)cyclopropyl-1-N-methoxy-N-methylcarboxyamide for intermediate 6.2. m.p.=175°–177° C.; 1H NMR (300 MHz, DMSO-d$_6$, 99:1 trans:cis): 1.02 (m, 2H), 1.45 (m, 1H), 1.87 (m, 1H), 3.38 (m, 2H), 6.30 (bs, 2H), 7.05 (m,2H), 8.36 (m, 2H), 9.34 (s, 1H); MS (M+H)+=208; Analysis calc'd for C$_{10}$H$_{13}$N$_3$O$_2$: C, 57.96, H, 6.32, N, 20.28; Found: C, 57.95, H, 6.38, N, 20.32.

EXAMPLE 44

N-(1-trans-(2-(4-bromophenyl)cyclopropyl)ethyl)-N-hydroxyacetamide

The title compound was prepared according to the procedure of Example 27 substituting N-(1-trans-(2-(4-bromophenyl)cyclopropyl)ethyl)N-hydroxylamine for N-(1-trans-(2-phenylcyclopropyl)methyl-N-hydroxylamine m.p.=137°–139° C.; 1H NMR (300 MHz, DMSO-d$_6$, a single diastereomer): 0.81–0.96 (m, 2H), 1.17 (d, 3H, J=6.5 Hz), 1.27 (m, 1H), 1.92 (m, 1H), 2.00 (s, 3H), 3.95 (m, 1H), 7.03 (m, 2H), 7.42 (m, 2H), 9.54 (s, 1H); MS (M+H)+=299; Analysis calc'd for C$_{13}$H$_{16}$BrNO$_2$: C, 52.36, H, 5.41, N, 4.70; Found: C, 52.51, H, 5.50, N, 4.69.

EXAMPLE 45

N-(1-trans-((2-napthyl)cyclopropyl)ethyl)-N-hydroxyurea

The title compound was prepared according to the procedure of Example 6 substituting 2-naphthaldehyde for 3-phenoxybenzaldehyde. m.p.=137°–139° C.; 1H NMR (300 MHz, DMSO-d$_6$, 45:55 ratio of diastereomers): 0.91–1.10 (m, 2H), 1.16 and 1.19 (d, 3H, J=6.5 Hz), 1.33–1.51 (m, 1H), 2.01 and 2.11 (m, 1H), 3.68 (m, 1H), 6.31 and 6.32 (bs, 2H), 7.22 (dd, 1H, J=2 Hz, J=8.5 Hz), 7.42 (m, 2H), 7.56 (m, 1H), 7.75–7.86 (m, 3H), 8.99 and 9.05 (s, 1H); MS (M+H)+=271; Analysis calc'd for C$_{16}$H$_{18}$N$_2$O$_2$: C, 71.09, H, 6.71, N, 10.37; Found: C, 70.81, H, 6.77, N, 10.20.

EXAMPLE 46

N-(1-trans-(2-(4-methylphenyl)cyclopropyl)methyl)-N-hydroxyacetamide

The title compound was prepared according to the procedure of Example 27 substituting N-(1-trans-(2-(4-methylphenyl)cylopropyl)methyl)-N-hydroxylamine for N-(1-trans-(2-phenylcyclopropyl)methyl)-N-hydroxylamine. m.p.=62°–64° C.; 1H NMR (300 MHz, DMSO-d$_6$): 0.87 (m, 2H), 1.30 (m, 1H), 1.81 (m, 1H), 1.98 (s, 3H), 2.23 (s, 3H), 3.51 (d, 2H, J=7 Hz), 6.93 (d, 2H, J=8.5 Hz), 7.04 (d, 2H, J=8.5 Hz), 9.80 (bs, 1H); MS (M+H)+=220; Analysis calc'd for C$_{13}$H$_{17}$NO$_2$: C, 71.20, H, 7.82, N, 6.39; Found: C, 71.14, H, 7.88, N, 6.21.

EXAMPLE 47

N-(1-trans-(2-(4-methylphenyl)cyclopropyl)methyl)-N-hydroxyurea

The title compound was prepared according to the procedure of Example 10 substituting trans-2-(4-methylphenyl)cyclopropyl)-1-N-methoxy-N-methylcarboxyamide for intermediate 6.2. m.p.=144°–145° C.; 1H NMR (300 MHz, DMSO-d$_6$): 0.83 (m, 2H), 1.27 (m, 1H), 1.79 (m, 1H), 2.24 (s, 3H), 3.35 (2H, under DMSO/H2O), 6.27 (bs, 2H), 6.93 (d, 2H, J=8.5 Hz), 7.03 (d, 2H, J=8.5 Hz), 9.38 (s, 1H); MS (M+H)+=221; Analysis calc'd for C$_{13}$H$_{16}$N$_2$O$_2$: C, 65.43, H, 7.32, N, 12.72; Found: C, 65.40, H, 7.32, N, 12.65.

EXAMPLE 48

N-(1-trans-(2-(3-(2-pyridyloxy)phenyl)cyclopropyl)methyl)-N-hydroxyurea

A solution of 3-hydroxybenzaldehyde (5.00 g, 40.9 mmol) and N,N-dimethylhydrazine (9.83 g, 163.6 mmol) in ethanol (20 mL) was refluxed for 15 hrs. It was then concentrated. The resulting residue was chromatographed (silica gel, hexane:ether, 1:1) to afford 6.24 g (93%) of intermediate 48.1 as a pale yellow solid.

To a solution of intermediate 48.1 (6.23 g, 38 mmol) in DMSO (150 mL) was added sodium hydride (958 mg, 39.9 mmol) and the mixture was allowed to stir for 20 mins. 2-Bromopyridine (6.00 g, 38 mmol) was then added and the reaction was heated to 150° C. for 15 hrs. It was then cooled to room temperature and diluted with brine (150 mL). This aqueous mixture was extracted with ethylacetate (3×200 mL). The organics were combined, dried with MgSO$_4$ and concentrated. The resulting residue was chromatographed (silica gel, ether:hexanes, 25:75) to afford 8.21 g (90%) of intermediate 48.2.

To a solution of Cu(OAc)$_2$.H2O (27.20 g, 136.3 mmol) in H2O (140 mL) was added intermediate 48.2 (8.21 g, 34.1 mmol) as a solution in THF (140 mL). This mixture was brought to reflux for 4 days. The reaction was then diluted with aqueous 10% NH$_4$OH (250 mL) and extracted with ethylacetate (3×250 mL). The organics were combined, dried with MgSO$_4$ and concentrated. The resulting residue was chromatographed (silica gel, CH$_2$Cl$_2$:hexanes, 95:5) to afford 6.00 g of 3-(2-pyridyloxy)benzaldehyde as a white solid.

The title compound was prepared, as an oil, according to the procedure of Example 10 substituting 3-(2- pyridyloxy)benzaldehyde for 3-phenoxybenzaldehyde. 1H NMR (300 MHz, DMSO-d$_6$): 0.90 (m, 2H), 1.34 (m, 1H), 1.87 (m, 1H), 3.36 (2H, under DMSO/H2O), 6.29 (bs, 2H), 6.79-6.92 (m, 3H), 6.99 (m, 1H), 7.11 (m, 1H), 7.26 (m, 1H), 7.84 (m, 1H), 8.15 (m, 1H), 9.32 (s, 1H); MS (M+H)+ =300.

EXAMPLE 49

N-(trans-(2-(3-(4-pyridyloxy)phenyl)cyclopropyl)methyl)-N-hydroxyurea

The title compound was prepared according to the procedure of Example 48 substituting 4-bromopyridine for 2-bromopyridine. m.p.=130.5°-131.5° C.; 1H NMR (300 MHz, DMSO-d$_6$): 0.93 (t, 2H, J=7.5 Hz), 1.35 (m, 1H), 1.90 (m, 1H), 3.37 (d, 2H, J=1.5 Hz), 6.30 (bs, 2H), 6.85-6.94 (m, 4H), 6.99 (d, 1H, J=8.5 Hz), 7.34 (t, 1H, J=8.5 Hz), 8.45 (dd, 2H, J=1.5 Hz, J=4 Hz), 9.31 (s, 1H); MS (M+H)+ =300; Analysis calc'd for C$_{16}$H$_{17}$N$_3$O$_3$.1/2CH$_3$OH: C, 62.84, H, 6.07, N, 13.33; Found: C, 63.05, H, 6.06, N, 13.13.

EXAMPLE 50

N-(1-trans-(2-(3-(4-fluorophenoxy)phenyl)cyclopropyl)methyl)-N-hydroxyurea

A heterogeneous mixture of 3-hydroxybenzaldehyde (9.16 g, 75 mmol), 4-bromofluorobenzene (27.30 g, 156 mmol), K$_2$CO$_3$ (16.07 g, 116.3 mmol) and copper powder (2.38 g, 37.5 mmol) in pyridine (75 mL) was refluxed for 40 hrs. It was then cooled to room temperature and filtered through Celite. The filtrate was diluted with ethylacetate (500 mL) and washed with water (3×300 mL). The organic was then dried with MgSO$_4$ and concentrated. The resulting residue was chromatographed (silica gel, hexane:ether, 85:15) to afford 11.83 g (73%) of 3-(4-fluorophenoxy)benzaldehyde as a yellow oil.

The title compound was prepared according to the procedure of Example 10 substituting 3-(4-fluorophenoxy)benzaldehyde for 3-phenoxybenzaldehyde. m.p.=93°-95° C.; 1H NMR (300 MHz, DMSO-d$_6$): 0.89 (m, 2H), 1.32 (m, 1H), 1.84 (m, 1H), 3.35 (d, 2H, J=7 Hz), 6.29 (bs, 2H), 6.70 (m, 2H), 6.81 (d, 1H, J=8.5 Hz), 7.04 (m, 2H), 7.22 (m, 3H), 9.30 (s, 1H); MS (M+H)+ =317; Analysis calc'd for C$_{17}$H$_{17}$FN$_2$O$_3$: C, 64.54, H, 5.42, N, 8.86; Found: C, 64.24, H, 5.46, N, 8.84.

EXAMPLE 51

N-(1-trans-(2-(3-(4-methylphenoxy)phenyl)cyclopropyl)methyl)-N-hydroxyurea

The title compound was prepared according to the procedure of Example 50 substituting 4-bromotoluene for 4-bromofluorobenzene. m.p.=107°-110° C.; 1H NMR (300 MHz, DMSO-d$_6$): 0.87 (m, 2H), 1.31 (m, 1H), 1.82 (m, 1H), 2.28 (s, 3H), 3.34 (2H, under DMSO/H2O), 6.28 (bs, 2H), 6.67 (m, 2H), 6.79 (m, 1H), 6.90 (m, 2H), 7.20 (m, 3H), 9.30 (s, 1H); MS (M+H)+ =313; Analysis calc'd for C$_{18}$H$_{20}$N$_2$O$_3$: C, 69.21, H, 6.45, N, 8.97; Found: C, 69.25, H, 6.53, N, 8.93.

EXAMPLE 52

N-(1-trans-(2-(3-(4-chlorophenoxy)phenyl)cyclopropyl)methyl)-N-hydroxyurea

The title compound was prepared according to the procedure of Example 50 subsituting 4-chloroiodobenzene for 4-bromofluorobenzene. m.p.=101°-104° C.; 1H NMR (300 MHz, DMSO-d$_6$): 0.90 (m, 2H), 1.33 (m, 1H), 1.86 (m, 1H), 3.35 (2H, under DMSO/H2o), 6.29 (bs, 2H), 6.76 (m, 2H), 6.86 (m, 1H), 7.01 (m, 2H), 7.26 (t, 1H, J=8.5 Hz), 7.42 (m, 2H), 9.30 (s, 1H); MS (M+H)+ =333; Analysis calc'd for C$_{17}$H$_{17}$ClN$_2$O$_3$: C, 61.35, H, 5.15, N, 8.42; Found: C, 61.09, H, 5.14, N, 8.34.

EXAMPLE 53

N-(1-trans-(2-(3-(4-methoxyphenoxy)phenyl)cyclopropyl)-methyl)-N-hydroxyurea

The title compound was prepared according to the procedure of Example 50 subsituting 4-bromoanisole for 4-bromofluorobenzene. m.p.=91°-94° C.; 1H NMR (300 MHz, DMSO-d$_6$): 0.80-0.93 (m, 2H), 1.30 (m, 1H), 1.82 (m, 1H), 3.34 (d, 2H, J=7 Hz), 3.75 (s, 3H), 6.27 (bs, 2H), 6.63 (m, 2H), 6.75 (m, 1H), 6.97 (m, 4H), 7.18 (m, 1H), 9.30 (s, 1H); MS (M+H)+ =329.

EXAMPLE 54

N-(1-trans-(2-(3-(4-benzyloxyphenoxy)phenyl)cyclopropyl)-methyl)-N-hydroxyurea

To a solution of 4-bromophenol (8.65 g, 50 mmol) in dimethylsulfoxide (100 mL) was added potassium t-butoxide (6.45 g, 57.5 mmol) and the mixture was stirred for 20 mins. Benzyl bromide (10.26 g, 60 mmol) was then added and the reaction was stirred for 1 hr. It was then diluted with brine (150 mL) and extracted with ethylacetate (3×200 mL). The organics were combined, dried with MgSO$_4$ and concentrated. The resulting residue was distilled under vacuum (0.8 mm Hg) to afford 13.17 g of 4-benzyloxybromobenzene as a white solid (b.p. 150-155∞C).

The title compound was prepared according to the procedure of Example 50 substituting 4-benzyloxybromobenzene for 4-bromofluorobenzene. m.p.=116.5°-117.5° C.; 1H NMR (300 MHz, DMSO-d$_6$): 0.81-0.93 (m, 2H), 1.31 (m, 1H), 1.82 (m, 1H), 3.35 (2H, under DMSO/H2O), 5.08 (s, 2H), 6.28 (s, 2H), 6.55-6.66 (m, 2H), 6.76 (d, 1H, J=8.5 Hz), 7.01 (m, 4H), 7.18 (m, 1H), 7.30-7.49 (m, 5H), 9.30 (s, 1H); MS (M+H)+ =405; Analysis calc'd for C$_{24}$H$_{24}$N$_2$O$_4$: C, 71.27, H, 5.98, N, 6.93; Found: C, 70.51, H, 6.03, N, 6.77.

EXAMPLE 55

N-(1-trans-(2-(4-methoxy-3-phenoxyphenyl)cyclopropyl)methyl)-N-hydroxyurea

The title compound was prepared according to the procedure of Example 50 substituting bromobenzene for 4-bromofluorobenzene and 3-hydroxy-p-anisaldehyde for 3-hydroxybenzaldehyde. m.p.=93.5-96.5∞C; 1H NMR (300 MHz, DMSO-d$_6$): 0.81 (m, 2H), 1.24 (m, 1H), 1.79 (m, 1H), 3.33 (2H, under DMSO/H2O), 3.68 (s, 3H), 6.27 (bs, 2H), 6.74 (d, 1H, J=2.5 Hz), 6.80 (m, 2H), 6.91 (dd, 1H, J=2.5 Hz, J=8.5 Hz), 7.02 (m, 2H), 7.30 (m, 2H), 9.28 (s, 1H); MS (M+H)+ =329; Analysis calc'd for C$_{18}$H$_{20}$N$_2$O$_4$: C, 65.84, H, 6.14, N, 8.53; Found: C, 65.75, H, 6.32, N, 8.27.

EXAMPLE 56

N-(1-trans-(2-(3-methyl-4-phenoxy)phenylcylcopropyl)methyl)-N-hydroxyurea.

The title compound was prepared according to the procedure of Example 50 substituting bromobenzene for 4-bromofluorobenzene and 4-hydroxy-3-methylbenzaldehyde for 3-hydroxy-p-anisaldehyde. m.p.=121.5°-122.5° C.; 1H NMR (300 MHz, DMSO-d$_6$): 0.87 (m, 2H ), 1.32 (m, 1H), 1.83 (m, 1H), 2.10 (s, 3H), 3.37 (dd, 2H, J=3 Hz, J=7 Hz), 6.30 (bs, 2H), 6.81 (m, 3H), 6.91 (m, 1H), 7.03 (m, 2H), 7.32 (m, 2H), 9.31 (s, 1H); MS (M+H)+ =313; Analysis calc'd for C18H20N2O3: C, 69.21, H, 6.45, N, 8.97; Found: C, 69.20, H, 6.50, N, 8.99.

EXAMPLE 57

N-(1-trans-(2-napthyl)cyclopropyl)ethyl)-N-hydroxyacetamide

The title compound was prepared according to the procedure of Example 27 substituting N-(1-trans-(2-napthyl)cyclopropyl)ethyl)-N-hydroxylamine for N-(1-trans-(2-phenylcyclopropyl)methyl)-N-hydroxylamine. 1H NMR (300 MHz, DMSO-$d_6$, 1:1 ratio of diastereomers): 0.96–1.10 (m, 2H), 1.22 (d, 3H, J 7 Hz), 1.37–1.56 (m, 1H), 1.99 and 2.02 (s, 3H), 2.08 (m, 1H), 4.02 (m, 1H), 7.21 (m, 1H), 7.37–7.49 (m, 2H), 7.58 (m, 1H), 7.77–7.86 (m, 3H), 9.50 and 9.57 (bs, 1H); MS (M+H)+ =270; Analysis calc'd for $C_{17}H_{19}NO_2$: C, 75.81, 7.11, N, 5.20; Found: C, 75.60, H, 7.26, N, 5.07.

EXAMPLE 58

N-(1-trans-(2-(2-pyridyl)cyclopropyl)methyl)-N-hydroxyurea

The title compound was prepared accoridng to the the procedure of Example 10 substituting trans-2-(2-pyridyl)cyclopropyl-1-N-methoxy-N-methylcarboxyamide for intermediate 6.2. m.p.=142.5°–144.0° C.; 1H NMR (300 MHz, DMSO-$d_6$): 0.91 (m, 1H), 1.08 (m, 1H), 1.62 (m, 1H), 2.00 (m, 1H), 3.38 (d, 2H, J=6.5 Hz), 6.27 (bs, 2H), 7.10 (m, 1H), 7.24 (m, 1H), 7.61 (m, 1H), 8.38 (m, 1H), 9.30 (s, 1H); MS (M+H)+ =208; Analysis calc'd for $C_{10}H_{13}N_3O_2$: C, 57.96, H, 6.32, N, 20.28; Found: C, 58.00, H, 6.33, N, 19.88.

EXAMPLE 59

N-(1-trans-(2-(4-methylphenyl)cyclopropyl)ethyl)-N-hydroxyacetamide

The title compound was prepared, as a wax, according to the procedure of Example 27 substituting N-(1-trans-(2-(4-methylphenyl)cyclopropyl)ethyl)-N-hydroxylamine for N-(1-trans-(2-phenylcyclopropyl)-methyl)-N-hydroxylamine. 1H NMR (300 MHz, DMSO-$d_6$, 45:55 ratio of diastereomers): 0.76–0.92 (m, 2H), 1.18 (d, 3H, J=7 Hz), 1.20–1.37 (m, 1H), 1.83 (m, 1H), 1.97 and 2.00 (s, 3H), 2.22 and 2.24 (s, 3H), 3.94 (m, 1H), 6.87–6.97 (m, 2H), 7.04 (m, 2H), 9.47 and 9.52 (bs, 1H); MS (M+H)+ =234; Analysis calc'd for $C_{14}H_{19}NO_2$: C, 72.07, H, 8.21, N, 6.00; Found: C, 72.39, H, 8.24, N, 5.81.

EXAMPLE 60

N-(1-trans-(2-(4-methoxyphenyl)cyclopropyl)methyl)-N-hydroxyurea

The title compound was prepared according to the procedure of Example 10 substituting trans-2-(4-methoxyphenyl)cyclopropyl-1-N-methoxy-N-methylcarboxyamide for intermediate 6.2. m.p.=148°–150° C.; 1H NMR (300 MHz, DMSO-$d_6$): 0.80 (m, 2H), 1.24 (m, 1H), 1.79 (m, 1H), 3.35 (m, 2H), 3.70 (s, 3H), 6.27 (bs, 2H), 6.80 (m, 2H), 6.99 (m, 2H), 9.28 (s, 1H); MS (M+H)+ =237; Analysis calc'd for $C_{12}H_{16}N_2O_3$: C, 61.00, H, 6.83, N, 11.86; Found: C, 61.16, H, 6.95, N, 11.78.

EXAMPLE 61

N-(1-trans-(2-(4-methyl-3-phenoxyphenyl)cyclopropyl)methyl)-N-hydroxyurea

To a solution of 3-hydroxy-4-methylbenzoic acid (15.22 g, 0.1 mole) in THF (250 mL) was added borane.-dimethylsulfide (32.0 mL of a 10.0M solution, 0.32 mole) dropwise. Upon completion of addition, the reaction was stirred for 18 hrs. It was then quenched dropwise by the slow addition of aqueous 10% HCl (250 mL) and extracted with ethylacetate (3×250 mL). The organics were combined, dried with MgSO4 and concentrated. The resulting residue was taken up in CH2Cl2 (500 mL) and pyridinium dichromate (45.15 g, 0.12 mole) was added. The resulting mixture was stirred for 48 hrs. It was then filtered through Celite and concentrated. The resulting residue was chromatographed (silica gel, ether:hexanes, 30:70) to afford 4.55 g of 3-hydroxy-4-methylbenzaldehyde as a yellow solid.

The title compound was prepared according to the procedure of Example 50 subsituing 3-hydroxy-4-methylbenzaldehyde for 3-hydroxybenzaldehyde and bromobenzene for 4-bromofluorobenzene. m.p.=122°–124° C.; 1H NMR (300 MHz, DMSO-$d_6$): 0.76–0.89 (m, 2H), 1.25 (m, 1H), 1.79 (m, 1H), 2.08 (s, 3H), 3.32 (2H, under DMSO/H2O), 6.26 (bs, 2H), 6.61 (m, 1H), 6.79–6.88 (m, 3H), 7.05 (m, 1H), 7.18 (d, 1H, J=8.5 Hz), 7.34 (m, 2H), 9.27 (s, 1H); MS (M+H)+ =313. Analysis calc'd for $C_{18}H_{20}N_2O_3$: C, 69.21, H, 6.45, N, 8.97; Found: C, 69.70, H, 6.48, N, 9.01.

EXAMPLE 62

N-(1-trans-(2-(6-methyl-2-pyridyl)cyclopropyl)methyl)-N-hydroxyurea

The title compound was prepared according to the procedure of Example 10 substituting trans-(2-(5-methyl-2-pyridyl)cyclopropyl)-1-N-methoxy-N-methylcarboxyamide for intermediate 6.2. m.p.=141.0°–141.5° C.; 1H NMR (300 MHz, DMSO-$d_6$): 0.89 (m, 1H), 1.05 (m, 1H), 1.61 (m, 1H), 1.95 (m, 1H), 2.36 (s, 3H), 3.37 (m, 2H), 6.27 (bs, 2H), 6.95 (d, 1H, J=8 Hz), 7.01 (d, 1H, J=8 Hz), 7.49 (t, 1H, J=8 Hz), 9.29 (s, 1H); MS (M+H)+ =222; Analysis calc'd for $C_{11}H_{15}N_3O_2$: C, 59.71, H, 6.83, N, 18.99; Found: C, 59.64, H, 6.88, N, 18.97.

EXAMPLE 63

N-(1-trans-(4-ispopropylphenyl)cyclopropyl)methyl)-N-hydroxyurea

The title compound was prepared according to the procedure of Example 10 substituting trans-(2-(4-isopropylphenyl)cyclopropyl)-1-N-methoxy-N-methyl-carboxyamide for intermediate 6.2. m.p.=131.5°–132.5° C.; 1H NMR (300 MHZ, DMSO-$d_6$): 0.85 (m, 2H), 1.16 (d, 6H, J=7 Hz), 1.29 (m, 1H), 1.80 (m, 1H), 2.81 (septet, 1H), 3.35 (m, 2H), 6.28 (bs, 2H), 6.96 (d, 2H, J=8.5 Hz), 7.09 (d, 2H, J=8.5 Hz), 9.29 (s, 1H); Analysis calc'd for $C_{14}H_{20}N_2O_2$: C, 67.71, H, 8.12, N, 11.28; Found: C, 67.61, H, 8.18, N, 11.26.

EXAMPLE 64

N-(1-trans-(3-isopropoxyphenyl)cyclopropyl)methyl)-N-hydroxyurea

To a solution of 3-hydroxybenzaldehyde (6.00 g, 49.1 mmol) in DMSO (100 mL) was added potassium t-butoxide (6.34 g, 56.5 mmol) and the resulting mixture was stirred for 20 mins. A sample of 2-bromopropane (7.25 g, 59 mmol) was added and the reaction was stirred for 18 hrs. It was then diluted with brine (100 mL) and extracted with ethylacetate (3×125 mL). The organics were combined, dried with MgSO4 and concentrated. The resulting residue was chromatographed (silica gel, ether:hexanes, 10:90) to afford 4.61 g (57%) of 3-isopropoxybenzaldehyde as a colorless oil.

The title compound was prepared according to the procedure of Example 10 substituting trans-(2-(3-isopropoxyphenyl)cyclopropyl)-1-N-methoxy-N-methylcarboxyamide for intermediate 6.2. m.p.=146.5°–149.0° C.; 1H NMR (300 MHz, DMSO-$d_6$): 0.86 (t, 2H, J=6.5 Hz), 1.24 (d, 6H, J=6 Hz), 1.31 (m, 1H), 1.80 (m, 1H), 3.35 (m, 2H), 4.57 (septet, 1H), 6.28 (bs, 2H), 6.54–6.68 (m, 3H), 7.11 (t, 1H, J=8 Hz), 9.29 (s, 1H); MS (M+H)+ =265; Analysis calc'd for $C_{14}H_{20}N_2O_3$: C, 63.61, H, 7.61, N, 10.60; Found: C, 63.54, H, 7.64, N, 10.57.

EXAMPLE 65

N-(1-trans-(2-(2-furfuranyl)cyclopropyl)ethyl-N-hydroxyurea

The title compound was prepared, as an oil, according to the procedure of Example 6 substituting 2-furaldehyde for 3-phenoxybenzaldehyde. 1H NMR (300 MHz, DMSO-$d_6$, mixture including all 4 possible diastereomers): 0.83 (m, 2H), 1.12 (m, 3H), 1.21–1.47 (m, 1H), 1.83–1.96 (m, 1H), 3.61 (m, 1H), 5.94–6.07 (m, 1H), 6.23–6.36 (m, 3H), 7.37–7.49 (m, 1H), 9.01 and 9.03 and 9.04 and 9.06 (s, 1H); MS (M+H)+ =211.

EXAMPLE 66

N-(1-trans-(2-(3-bromo-4-isopropoxyphenyl)cyclopropyl)-methyl)-N-hydroxyurea

To a solution of 4-hydroxybenzaldehyde (10.00 g, 82 mmol) in chloroform (170 mL) was addedbromine (13.76 g, 86.1 mmol) dropwise as a solution in chloroform (80 mL). Upon completion of addition, the reaction was stirred for 30 mins. at room temperature then warmed to 40° C. for 1 hr. The reaction was diluted with aqu. sat'd NaHCO3 (250 mL) and the layers were separated. The aqueous was extracted with CH2Cl2 (2×250 mL). The organics were combined, dried with MgSO4 and concentrated to afford 7.49 g of 3-bromo-4-hydroxybenzaldehyde which contains 10% of 3,5-dibromo-4-hydroxybenzaldehyde.

The title compound was prepared, as a glass, according to the procedure of Example 65 substituting 3-bromo-4-hydroxybenzaldehyde for 3-hydroxybenzaldehyde. 1H NMR (300 MHz, DMSO-$d_6$): 0.84 (t, 2H, J=7 Hz), 1.26 (m, 1H), 1.26 (d, 6H, J=6 Hz), 1.81 (m, 1H), 3.36 (m, 2H), 4.56 (septet, 1H), 6.29 (bs, 2H), 7.00 (d, 2H, J=1 Hz), 7.26 (s, 1H), 9.30 (s, 1H); MS (M+H)+ =343.

EXAMPLE 67

N-(1-trans-(2-(4-isopropoxyphenyl)cyclopropyl)methyl)-N-hydroxyurea

The title compound was prepared according to the procedure of Example 65 substituting 4-hydroxybenzaldehyde for 3-hydroxybenzaldehyde. m.p.=159°–160° C.; 1H NMR (300 MHz, DMSO-$d_6$): 0.80 (m, 2H), 1.23 (d, 6H, J=6.5 Hz), 1.23 (m, 1H), 1.77 (m, 1H), 3.34 (m, 2H), 4.52 (septet, 1H), 6.27 (bs, 2H), 6.78 (m, 2H), 6.95 (m, 2H), 9.28 (s, 1H); MS (M+H)+ =265; Analysis calc'd for $C_{14}H_{20}N_2O_3$: C, 63.61, H, 7.63, N, 10.60; Found: C, 63.45, H, 7.60, N, 10.58.

EXAMPLE 68

N-(1-trans-(2-(2-furfuryl)cyclopropyl)ethyl)-N-hydroxyacetamide

The title compound was prepared, as an oil, according to the procedure of Example 27 substituting N-(1-trans-(2-(2-furfuryl)cyclopropyl)ethyl)-N-hydroxylamine for N-(1-trans-(2-phenylcyclopropyl)methyl)-N-hydroxylamine. 1H NMR (300 MHz, DMSO-$d_6$, 1:1 ratio of diastereomers): 0.79–0.93 (m, 2H), 1.16–1.19 (d, 3H, J=6 Hz), 1.30–1.47 (m, 1H), 1.87 (m, 1H), 1.98 and 1.99 (s, 3H), 3.94 (m, 1H), 6.01 and 6.05 (d, 1H, J=3 Hz), 6.31 (m, 1H), 7.41 and 7.45 (m, 1H), 9.52 and 9.55 (bs, 1H); MS (M+H)+ =210; Analysis calc'd for $C_{11}H_{15}NO_3$: C, 63.14, H, 7.23, N, 6.69; Found: C, 62.97, H, 7.14, N, 6.47.

EXAMPLE 69

N-(1-trans-(2-(4-quinolyl)cyclopropyl)methyl)-N-hdyroxyurea

The title compound was prepared according to the procedure of Example 10 substituting trans-(2-(4-quinonyl)cyclopropyl)-1-N-methoxy-N-methylcarboxyamide for intermediate 6.2. m.p.=174°–176° C.; 1H NMR (300 MHz, DMSO-$d_6$): 1.11–1.23 (m, 2H), 1.50 (m, 1H), 2.55 (m, 1H), 3.57 (d, 2H, J=6.5 Hz), 6.35 (bs, 2H), 7.12 (d, 1H, J=4 Hz), 7.65 (m, 1H), 7.76 (m, 1H), 8.01 (dd, 1H, J=8.5 Hz, J=1 Hz), 8.43 (dd, 1H, J=8.5 Hz, J=1 Hz), 8.75 (d, 1H, J=8 Hz), 9.41 (s, 1H); MS (M+H)+ =258; Analysis calc'd for $C_{14}H_{15}N_3O_2$: C, 65.35, H, 5.88, N, 16.33; Found: C, 65.28, H, 5.99, N, 16.30.

EXAMPLE 70

N-(1-trans-(2-(2-benzofuranyl)cyclopropyl)methyl)-N-hydroxyurea

To a mixture of 2,3-benzofuran (23.63 g, 0.2 mol) and N,N-dimethylformamide (22 g, 0.3 mol) was added phosphorous oxychloride (46 g, 0.3 mol) dropwise. Upon completion of addition, the mixture was stirred for 1 hr, then warmed to 50° C. and kept at that temperature for 60 hrs. It was then poured into ice (250 mL). The resulting aqueous mixture was neutralized to pH6 by the addition of aqu. 2N NaOH and extracted with ether (3×300 mL). The organics were combined, dried with MgSO4 and concentrated. The residue was distilled to afford 9.21 g of 2-benzofurancarboxaldehyde as a pale yellow oil (b.p.=98°–100° C. at 0.6 mm Hg).

The title compound was prepared according to the procedure of Example 10 subsituting trans-(2-(2-benzofuranyl)cyclopropyl)-1-N-methoxy-N-methylcarboxyamide for intermediate 6.2. m.p.=153.5–155.0∞C; 1H NMR (300 MHz, DMSO-$d_6$): 1.01 (m, 1H), 1.10 (m, 1H), 1.61 (m, 1H), 2.07 (m, 1H), 3.41 (d, 2H, J=6.5 Hz), 6.33 (bs, 2H), 6.55 (s, 1H), 7.18 (m, 2H), 7.41–7.52 (m, 2H), 9.37 (s, 1H); MS (M+H)+ =247.

EXAMPLE 71

N-(1-trans-(3,3-difluoro-2-phenylcyclopropyl)methyl)-N-hydroxyurea

To a solution of trans-1-acetoxymethyl-2,2-difluoro-3-phenylcyclopropane (9.7 mmol, prepare according to Kobayashi et al. J. Org. Chem, 1982, 47, 3232) in methanol (50 mL) was added K2CO3 (1.34 g, 9.7 mmol) and the reaction was stirred for 20 mins. The solution was then decanted from the solids and concentrated. The residue was purified by column chromatography (silica gel, ether:hexanes, 35:65) to afford 1.72 g (96%) of trans-2,2-difluoro-1-hydroxymethyl-3-phenylcyclopropane.

To a solution of oxalyl chloride (1.36 g, 10.7 mmol) in $CH_2Cl_2$ (40 mL) at −78° C., was added dimethylsulfoxide (1.74 g, 22.32 mmol) dropwise and the mixture was stirred for 5 mins. A solution of trans-2,2-difluoro-1-hydroxymethyl-3-phenylcyclopropane (1.71 g, 9.3 mmol) in $CH_2Cl_2$ (5 mL) was added dropwise. Upon completion of addition, the reaction was stirred for 20 mins at −78° C. Triethylamine (4.70 g, 46.5 mmol) was added, the cooling bath was withdrawn and the reaction was allowed to warm to room temperature It was then diluted with brine (50 mL) and the layers were separated. The aqueous was extracted with $CH_2Cl_2$ (2×50 mL). The organics were combined, dried with $MgSO_4$ and concentrated to afford trans-3,3-difluoro-2-phenyl-1-cyclopropylcarboxaldehyde.

The title compound was prepared according to the procedure of Example 1 substituting trans-3,3-difluoro-2-phenyl-1-cyclopropylcarboxaldehyde for intermediate 1.4. m.p.=139.5°-140.5° C.; 1H NMR (300 MHz, DMSO-$d_6$): 2.28 (sextet, 1H), 2.85 (dd, 1H, J=8 Hz, J=14.5 Hz), 3.53 (dd, 1H, J=7 Hz, J=14.5 Hz), 3.75 (m, 1H), 6.46 (bs, 2H), 7.23–7.38 (m, 5H), 9.51 (s, 1H): MS $(M+NH_4)^+=260$.

EXAMPLE 72

N-(1-trans-(2-(3-phenoxyphenyl)cyclopropyl)methyl)-N-hydroxyurea potassium salt

The potassium salt of the product of Example 10 is prepared by treatment with potassium bis-trimethylsilyl amide in tetrahydrofuran followed by precipitation of the salt by added hexane and collection by filtration.

EXAMPLE 73

N-(1-trans-(2-(3-phenoxyphenyl)cyclopropyl)methyl)-N-hydroxyurea sodium salt

The sodium salt of the product of Example 10 is prepared by treatment with sodium bis-trimethylsilyl amide in tetrahydrofuran followed by precipitation of the salt by added hexane and collection by filtration.

EXAMPLE 74

N-(1-trans-(2-(4-bromophenyl)cyclopropyl)methyl)-N-hydroxyurea potassium salt

The potassium salt of the product of Example 35 is prepared by treatment with potassium bis-trimethylsilyl amide in tetrahydrofuran followed by precipitation of the salt by added hexane and collection by filtration.

EXAMPLE 75

N-(1-trans-(2-(4-bromophenyl)cyclopropyl)methyl)-N-hydroxyacetamide potassium salt The potassium salt of the product of Example 38 is prepared by treatment with potassium bis-trimethylsilyl amide in tetrahydrofuran followed by precipitation of the salt by added hexane and collection by filtration.

EXAMPLE 76

N-(1-trans-(2(3-(4-fluorophenoxy)phenyl)cyclopropyl)-methyl)-N-hydroxyurea potassium salt The potassium salt of the product of Example 50 is prepared by treatment with potassium bis-trimethylsilyl amide in tetrahydrofuran followed by precipitation of the salt by added hexane and collection by filtration.

EXAMPLE 77

N-(1-trans-(2-(3-(4-chlorophenoxy)phenyl)cyclopropyl)methyl)-N-hydroxyurea potassium salt The potassium salt of the product of Example 52 is prepared by treatment with potassium bis-trimethylsilyl amide in tetrahydrofuran followed by precipitation of the salt by added hexane and collection by filtration.

EXAMPLE 78

N-acetoxy-N-(1-trans-(2-(3-phenoxyphenyl)cyclopropyl)-methyl)urea

The desired product is prepared from the product of Example 10 by treatment with triethylamine and acetyl chloride.

EXAMPLE 79

N-acetoxy-N-(1-trans-(2-(3-(4-chlorophenoxy)phenyl)-cyclopropyl)methyl)urea

The desired product is prepared from the product of Example 52 by treatment with triethylamine and acetyl chloride.

EXAMPLE 80

N-succinyloxy-N-(1-trans-(2-(3-(4-chlorophenoxy)-phenyl)-cyclopropyl)methyl)urea The desired product is prepared from the product of Example 52 by treatment with triethylamine and succinic anhydride.

EXAMPLE 81

N-trimethylsiloxy-N-(1-trans-(2-(3-phenoxyphenyl)-cyclopropyl)methyl) urea

The desired product is prepared from the product of Example 10 by treatment with trimethylsilylimidazole.

EXAMPLE 82

N-ethoxycarbonyloxy-N-(1-trans-(2-(3-phenoxyphenyl)cyclopropyl) methyl) urea

The desired product is prepared from the product of Example 10 by treatment with triethylamine and ethylchloroformate.

The compounds presented below in Table 3 are prepared by the method of Reaction Scheme 3 as described in Example 6 for the preparation of intermediate compound 6.2, by using the appropriate aldehyde precursor indicated in place of 3-phenoxybenzaldehyde, and continuing with the method of Example 10 to produce the desired product.

TABLE 5

| Starting Aldehyde | Product |
|---|---|
| (CH₃)₂N(CH₂)₂O—[phenyl with CHO and OCH₃] | Example 83<br>N-(1-trans-(2-(4-(2-dimethylaminoethoxy)-3-methoxyphenyl)cyclopropyl)methyl)-N-hydroxyurea |
| [2-thienyl]-CHO | Example 84<br>N-(1-trans-(2-(2-thienyl)cyclopropyl)methyl)-N-hydroxyurea |
| [5-methyl-2-thienyl]-CHO | Example 85<br>N-(1-trans-(2-(5-methyl-2-thienyl)cyclopropyl)methyl-N-hydroxyurea |
| [3-thienyl]-CHO | Example 86<br>N-(1-trans-(2-(3-thienyl)cyclopropyl)methyl)-N-hydroxyurea |
| [3-furyl]-CHO | Example 87<br>N-(1-trans-(2-(3-furyl)cyclopropyl)methyl)-N-hydroxyurea |
| 4-F-C₆H₄-CHO | Example 88<br>N-(1-trans-(2-(4-fluorophenyl)cyclopropyl)methyl)-N-hydroxyurea |
| CH₃CH₂O-C₆H₄-CHO | Example 89<br>N-(1-trans-(2-(4-ethoxyphenyl)cyclopropyl)methyl)-N-hydroxyurea |
| (CH₃)₂CHCH₂O-C₆H₄-CHO | Example 90<br>N-(1-trans-(2-(4-(2-methylpropoxy)phenyl)cyclopropyl)methyl)-N-hydroxyurea |
| 3-(3,4-dichlorophenoxy)benzaldehyde | Example 91<br>N-(1-trans-(2-(3-(3,4-dichlorophenoxy)phenyl)cyclopropyl)methyl)-N-hydroxyurea |
| 3-(3,5-dichlorophenoxy)benzaldehyde | Example 92<br>N-(1-trans-(2-(3-(3,5-dichlorophenoxy)phenyl)cyclopropyl)methyl)-N-hydroxyurea |

TABLE 5-continued

| Starting Aldehyde | Product |
|---|---|
| 3-(3-trifluoromethylphenoxy)benzaldehyde | Example 93<br>N-(1-trans-(2-(3-(3-trifluoromethylphenoxy)phenyl)cyclopropyl-methyl)-N-hydroxyurea |
| 3-(4-t-butylphenoxy)benzaldehyde | Example 94<br>N-(1-trans-(2-(3-(4-t-butylphenoxy)phenyl)cyclopropyl)methyl)-N-hydroxyurea |
| 4-methoxy-3-methylbenzaldehyde | Example 95<br>N-(1-trans-(2-(4-methoxy-3-methylphenyl)cyclopropyl)methyl)-N-hydroxyurea |
| 4-butoxybenzaldehyde | Example 96<br>N-(1-trans-(2-(4-butoxyphenyl)cyclopropyl)methyl)-N-hydroxyurea |
| 3-fluoro-4-methoxybenzaldehyde | Example 97<br>N-(1-trans-(2-(3-fluoro-4-methoxyphenyl)cyclopropyl)methyl)-N-hydroxyurea |
| 4-(methylthio)benzaldehyde | Example 98<br>N-(1-trans-(2-(4-(methylthio)phenyl)cyclopropyl)methyl)-N-hydroxyurea |
| 4-dimethylaminobenzaldehyde | Example 99<br>N-(1-trans-(2-(4-dimethylaminophenyl)cyclopropyl)methyl)-N-hydroxyurea |
| 4-benzyloxy-3-methoxybenzaldehyde | Example 100<br>N-(1-trans-(2-(4-benzyloxy-3-methoxyphenyl)cyclopropyl)methyl)-N-hydroxyurea |
| 3-bromo-4-methoxybenzaldehyde | Example 101<br>N-(1-trans-(2-(3-bromo-4-methoxyphenyl)cyclopropyl)methyl)-N-hydroxyurea |
| 3-benzyloxy-4-methoxybenzaldehyde | Example 102<br>N-(1-trans-(2-(3-benzyloxy-4-methoxyphenyl)cyclopropyl)methyl)-N-hydroxyurea |

TABLE 5-continued

| Starting Aldehyde | Product |
|---|---|
| 4-CHO, 3-OCH₃, 2-CH₃ benzaldehyde | Example 103<br>N-(1-trans-(2-(3-methoxy-4-methylphenyl)cyclopropyl)methyl)-N-hydroxyurea |
| 3-CHO, 4-F, 5-Cl benzaldehyde (3-chloro-4-fluorobenzaldehyde) | Example 104<br>N-(1-trans-(2-(3-chloro-4-fluorophenyl)cyclopropyl)methyl)-N-hydroxyurea |
| 3,5-bis(CF₃) benzaldehyde | Example 105<br>N-(1-trans-(2-(3,5-bis(trifluoromethyl)phenyl)cyclopropyl)methyl)-N-hydroxyurea |
| 3,4-difluorobenzaldehyde | Example 106<br>N-(1-trans-(2-(3,4-difluorophenyl)cyclopropyl)methyl)-N-hydroxyurea |
| 2,4-difluorobenzaldehyde | Example 107<br>N-(1-trans-(2-(2,4-difluorophenyl)cyclopropyl)methyl)-N-hydroxyurea |
| 4-allyloxybenzaldehyde | Example 108<br>N-(1-trans-(2-(4-allyloxyphenyl)cyclopropyl)methyl)-N-hydroxyurea |
| 3-(trifluoromethyl)benzaldehyde | Example 109<br>N-(1-trans-(2-(3-trifluoromethylphenyl)cyclopropyl)methyl)-N-hydroxyurea |
| 2-(trifluoromethyl)benzaldehyde | Example 110<br>N-(1-trans-(2-(2-trifluoromethylphenyl)cyclopropyl)methyl)-N-hydroxyurea |
| 4-(trifluoromethyl)benzaldehyde | Example 111<br>N-(1-trans-(2-(4-trifluoromethylphenyl)cyclopropyl)methyl)-N-hydroxyurea |
| 4-CHO, 3-CH₃, 2-CH₃, 5-OCH₃ benzaldehyde (2,3-dimethyl-4-methoxybenzaldehyde) | Example 112<br>N-(1-trans-(2-(2,3-dimethyl-4-methoxyphenyl)cyclopropyl)methyl)-N-hydroxyurea |
| 3-OCH₃, 4-OCH₃, 5-Br benzaldehyde | Example 113<br>N-(1-trans-(2-(3-bromo-4,5-dimethoxyphenyl)cylcopropyl)methyl)-N-hydroxyurea |

TABLE 5-continued

| Starting Aldehyde | Product |
|---|---|
| 2-bromo-4,5-dimethoxybenzaldehyde (CH₃O, CH₃O, Br, CHO) | Example 114<br>N-(1-trans-(2-(2-bromo-4,5-dimethoxyphenyl)cyclopropyl)methyl)-N-hydroxyurea |
| 3-bromobenzaldehyde | Example 115<br>N-(1-trans-(2-(3-bromophenyl)cyclopropyl)methyl)-N-hydroxyurea |
| 2-bromobenzaldehyde | Example 116<br>N-(1-trans-(2-(2-bromophenyl)cyclopropyl)methyl)-N-hydroxyurea |
| 3,4-dichlorobenzaldehyde | Example 117<br>N-(1-trans-(2-(3,4-dichlorophenyl)cyclopropyl)methyl)-N-hydroxyurea |
| 3,5-dichlorobenzaldehyde | Example 118<br>N-(1-trans-(2-(3,5-dichlorophenyl)cyclopropyl)methyl)-N-hydroxyurea |
| 5-butyl-2-pyridinecarboxaldehyde (CH₃(CH₂)₃) | Example 119<br>N-(1-trans-(2-(5-butyl-2-pyridyl)cyclopropyl)methyl)-N-hydroxyurea |
| 2,6-dichloro-4-pyridinecarboxaldehyde | Example 120<br>N-(1-trans-(2-(2,6-dichloro-4-pyridyl)cyclopropyl)methyl)-N-hydroxyurea |
| 5-bromo-3-pyridinecarboxaldehyde | Example 121<br>N-(1-trans-(2-(5-bromo-3-pyridyl)cyclopropyl)methyl)-N-hydroxyurea |
| 4-chlorobenzaldehyde | Example 122<br>N-(1-trans-(2-(4-chlorophenyl)cyclopropyl)methyl)-N-hydroxyurea |
| 3,5-dimethoxybenzaldehyde | Example 123<br>N-(1-trans-(2-(3,5-dimethoxyphenyl)cyclopropyl)methyl)-N-hydroxyurea |
| 3,4-diethoxybenzaldehyde | Example 124<br>N-(1-trans-(2-(3,4-diethoxyphenyl)cyclopropyl)methyl)-N-hydroxyurea |

TABLE 5-continued

| Starting Aldehyde | Product |
|---|---|
| 3,4,5-trimethoxybenzaldehyde (CH3O, CH3O, OCH3 substituents with CHO) | Example 125<br>N-(1-trans-(2-(3,4,5-trimethoxyphenyl)cyclopropyl)methyl)-N-hydroxyurea |
| 3,4-dimethoxybenzaldehyde (CH3O, OCH3 with CHO) | Example 126<br>N-(1-trans-(2-(3,4-dimethoxyphenyl)cyclopropyl)methyl)-N-hydroxyurea |
| 3,4-dibenzyloxybenzaldehyde (PhCH2O, OCH2Ph with CHO) | Example 127<br>N-(1-trans-(2-(3,4-dibenzyloxyphenyl)cyclopropyl)methyl)-N-hydroxyurea |
| 3,4-methylenedioxybenzaldehyde | Example 128<br>N-(1-trans-(2-(3,4-methylenedioxyphenyl)cyclopropyl)methyl)-N-hydroxyurea |
| 3,4-(1,4-benzodioxan)carbaldehyde | Example 129<br>N-(1-trans-(2-(3,4-(1,4-benzodioxan)phenyl)cyclopropyl)methyl)-N-hydroxyurea |
| 3-ethoxy-4-methoxybenzaldehyde (CH3O, OCH2CH3 with CHO) | Example 130<br>N-(1-trans-(2-(3-ethoxy-4-methoxyphenyl)cyclopropyl)methyl)-N-hydroxyurea |
| 3-(2-thienoxy)benzaldehyde | Example 131<br>N-(1-trans-(2-(3-(2-thienoxy)phenyl)cyclopropyl)methyl)-N-hydroxyurea |
| N-methyl-2-indolecarboxaldehyde | Example 132<br>N-(1-trans-(2-(N'-methyl-2-indolyl)cyclopropyl)methyl)-N-hydroxyurea |
| 4-phenylbenzaldehyde (Ph with CHO) | Example 133<br>N-(1-trans-(2-(4-phenylphenyl)cyclopropyl)methyl)-N-hydroxyurea |
| 2-thiazolecarboxaldehyde | Example 134<br>N-(1-trans-(2-(2-thiazolyl)cyclopropyl)methyl)-N-hydroxyurea |

TABLE 5-continued

| Starting Aldehyde | Product |
|---|---|
| benzothiazole-2-carboxaldehyde | Example 135<br>N-(1-trans-(2-(2-benzothiazolyl)cyclopropyl)methyl)-N-hydroxyurea |
| N-methyl-pyrrole-2-carboxaldehyde | Example 136<br>N-(1-trans-(2-(N'-methyl-2-pyrrolyl)cyclopropyl)methyl)-N-hydroxyurea |
| benzo[b]thiophene-3-carboxaldehyde | Example 137<br>N-(1-trans-(2-(benzo[b]-3-thienyl)cyclopropyl)methyl)-N-hydroxyurea |
| 3-methyl-thiophene-2-carboxaldehyde | Example 138<br>N-(1-trans-(2-(3-methyl-2-thienyl)cyclopropyl)methyl)-N-hydroxyurea |
| 4-bromo-thiophene-2-carboxaldehyde | Example 139<br>N-(1-trans-(2-(4-bromo-2-thienyl)cyclopropyl)methyl)-N-hydroxyurea |
| 5-bromo-thiophene-2-carboxaldehyde | Example 140<br>N-(1-trans-(2-(5-bromo-2-thienyl)cyclopropyl)methyl)-N-hydroxyurea |
| 5-chloro-thiophene-2-carboxaldehyde | Example 141<br>N-(1-trans-(2-(5-chloro-2-thienyl)cyclopropyl)methyl)-N-hydroxyurea |
| 5-phenyl-furan-2-carboxaldehyde | Example 142<br>N-(1-trans-(2-(5-phenyl-2-furyl)cyclopropyl)methyl)-N-hydroxyurea |
| 5-(2,4-difluorophenyl)-furan-2-carboxaldehyde | Example 143<br>N-(1-trans-(2-(5-(2,4-difluorophenyl)-2-furyl)cyclopropyl)methyl)-N-hydroxyurea |
| 5-bromo-furan-2-carboxaldehyde | Example 144<br>N-(1-trans-(2-(5-bromo-2-furyl)cyclopropyl)methyl)-N-hydroxyurea |
| 5-(3-pyridyl)-furan-2-carboxaldehyde | Example 145<br>N-(1-trans-(2-(5-(3-pyridyl)-2-furyl)cyclopropyl)methyl)-N-hydroxyurea |
| 5-ethyl-furan-2-carboxaldehyde | Example 146<br>N-(1-trans-(2-(5-ethyl-2-furyl)cyclopropyl)methyl-N-hydroxyurea |
| 5-ethoxymethyl-furan-2-carboxaldehyde | Example 147<br>N-(1-trans-(2-(5-ethoxymethyl-2-furyl)cyclopropyl)methyl)-N-hydroxyurea |

TABLE 5-continued

| Starting Aldehyde | Product |
|---|---|
| PhCH₂OCH₂—furan—CHO | Example 148<br>N-(1-trans-(2-(5-benzyloxymethyl-2-furyl)cyclopropyl)methyl)-N-hydroxyurea |
| Ph—CH=CH—furan—CHO | Example 149<br>N-(1-trans-(2-(5-(2-phenylethenyl)-2-furyl)cyclopropyl)methyl)-N-hydroxyurea |
| Ph—thiophene—CHO | Example 150<br>N-(1-trans-(2-(5-phenyl-2-thienyl)cyclopropyl)methyl)-N-hydroxyurea |
| (3-pyridyl)—thiophene—CHO | Example 151<br>N-(1-trans-(2-(5-(3-pyridyl)-2-thienyl)cyclopropyl)methyl)-N-hydroxyurea |
| CH₃CH₂OCH₂—thiophene—CHO | Example 152<br>N-(1-trans-(2-(5-ethoxymethyl-2-thienyl)cyclopropyl)methyl)-N-hydroxyurea |
| 4-CH₃O-C₆H₄-CH(CH₃)-O-C₆H₄-CHO | Example 153<br>N-(1-trans-(2-(4-(1-(4-methoxyphenyl)ethoxy)phenyl)cyclopropyl)methyl)-N-hydroxyurea |
| (4-pyridyl)-CH(CH₃)-O-C₆H₄-CHO | Example 154<br>N-(1-trans-(2-(4-(1-(4-pyridyl)ethoxy)phenyl)cyclopropyl)methyl)-N-hydroxyurea |
| (2-thienyl)-CH(CH₃)-O-C₆H₄-CHO | Example 155<br>N-(1-trans-(2-(4-(1-(2-thienyl)ethoxy)phenyl)cyclopropyl)methyl)-N-hydroxyurea |
| benzo[b]thien-3-yl-O-C₆H₄-CHO | Example 156<br>N-(1-trans-(2-(4-(benzo[b]thien-3-yl)oxy)phenyl)cyclopropyl)methyl)-N-hydroxyurea |
| Ph—(N-methylpyrrole)—CHO | Example 157<br>N-(1-trans-(2-(N'-methyl-5-phenyl-2-pyrrolyl)cyclopropyl)methyl)-N-hydroxyurea |
| 5-methyl-2-thienyl—2-thienyl—CHO | Example 158<br>N-(1-trans-(2-(5-(5-methyl-2-thienyl)-2-thienyl)cyclopropyl)methyl)-N-hydroxyurea |

TABLE 5-continued

| Starting Aldehyde | Product |
| --- | --- |
| (benzofuran-3-yl CHO) | Example 159<br>N-(1-trans-(2-(3-benzofuryl)cyclopropyl)methyl)-N-hydroxyurea |

EXAMPLE 160

N-(1-trans-(2-(3(4-hydroxyphenoxy)phenyl)cyclopropyl) methyl)-N-hydroxyurea

To a solution of trans-3-(3-(4-methoxyphenoxy)-phenyl)propenoic acid (32.87 g, 121.7 mmol) in $CH_2Cl_2$ (500 mL) at 0° C., was added boron tribromide (91.50 g, 365.2 mmol) dropwise over a period of 1 hr. Upon completion of addition, the reaction was stirred at 0° C. for 3 hrs. It was then quenched dropwise with methanol, warmed to r.t. and concentrated in vacuo. The residue was taken up in ethylacetate (500 mL) and washed once with $H_2O$ (500 mL). The organic was dried with $MgSO_4$ and concentrated. The resulting residue was chromatographed (silica gel, ether:hexanes, 2:3) to afford a mixture of trans-3-(3-(4-hydroxyphenoxy)phenyl)propenoic acid and methyl trans-3-(3-(4-hydroxyphenoxy)phenyl)propenoate which was used as is.

A solution of the acid and methyl ester from above in 1:1 1N LiOH:THF (400 mL) was stirred at r.t. for 72 hrs. It was then heated at reflux for an additional 24 hrs. It was cooled to r.t. and the THF stripped off in vacuo. The resulting aqueous residue was washed with ether (2×200 mL), then acidified to pH2 by the addition of conc. HCl. It was then extracted with ethylacetate (3×250 mL). These last organics were combined, dried with $MgSO_4$ and concentrated to afford solely trans-3-(3-(4-hydroxyphenoxy)phenyl)propenoic acid (27.09 g, 87%).

To a solution of trans-3-(3-(4-hydroxyphenoxy)-phenyl)propenoic acid (26.22 g, 102.4 mmol) in $CH_2Cl_2$ (500 mL) at 0° C., was added iso-butylchloroformate (29.38 g, 215.1 mmol) followed by the dropwise addition of triethylamine (21.73 g, 215.1 mmol). Upon completion of addition, the cooling bath was removed and the reaction allowed to warm to r.t. and stirred for 1 hr. N,O-dimethylhydroxylamine hydrochloride (11.99 g, 122.9 mmol) was then added followed by the dropwise addition of pyridine (19.44 g, 245.8 mmol) and the reaction was stirred for 30 mins. It was then diluted with brine (500 mL) and the layers were separated. The aqueous was extracted with $CH_2Cl_2$ (2×500 mL). The organics were combined, dried with $MgSO_4$ and concentrated. The resulting residue was chromatographed (silica gel, ether:hexanes, 1:1) to afford trans-N-methoxy-N-methyl-3-(3-(4-iso-butyloxycarboxyphenoxy)phenyl)propenamide (27.13 g, 66%).

A solution of trans-N-methoxy-N-methyl-3-(3-(4-iso-butylcarbonatephenoxy)phenyl) propenamide (27.13 g, 68.0 mmol) in 1:1 1N LiOH:THF (300 mL) was heated at 50° C. for 6 hrs. It was then cooled to r.t. and stirred for an additional 72 hrs. It was then heated to 50° C. for 24 hrs. then at reflux for an additional 24 hrs. The reaction was cooled to r.t. and the THF was stripped off. The resulting residue was acidified to pH2 by the addition of conc. HCl, and extracted with ethylacetate (3×150 mL). The organics were combined, dried with $MgSO_4$ and concentrated. The resulting residue was chromatographed (silica gel, $CH_2Cl_2$: ether, 4:1) to afford trans-N-methoxy-N-methyl-3-(3-(4-hydroxyphenoxy)phenyl)propenamide (18.32 g, 60%) as a white solid.

The title compound was prepared according to the procedure of Example 10 substituting trans-(2-(3-(4-hydroxyphenoxy)phenyl)cyclopropyl)-1-N-methoxy-N-methyl carboxyamide for intermediate 6.2. 1H NMR (300 MHz, DMSO-$d_6$):0.86 (m,2H), 1.30 (m, 1H), 1.81 (m,1H), 3.60 (m, 2H), 6.28 (bs, 2H), 6.59 (m, 2H), 6.70–6.80 (m, 3H), 6.87 (m, 2H), 7.16 (m, 1H), 9.30 (s, 1H), 9.34 (bs, 1H); MS (M+$NH_4$)+ = 332.

EXAMPLE 161

N-(1-trans-(2-(3-(4-(2-hydroxyethoxy)phenoxy)phenyl) cyclopropyl)methyl)-N-hydroxyurea To a solution of 2-bromoethanol (10.00 g, 80 mmol) and 3,4-dihydro-2H-pyran (10.1 g, 120 mmol) in $CH_2Cl_2$ (400 mL) was added a spatula of Amberlyst-15 ion exchange resin and the reaction was stirred for 18 hrs. It was then filtered through Celite and concentrated. Distillation (40 mm Hg, b.p.=102° C.) afforded tetrahydro-2-(2-bromoethoxy)-2H-pyran (8.49 g).

To a solution of 4-bromophenol (1.71 g, 9.91 mmol) in DMSO (40 mL) was added potassium t-butoxide (1.17 g, 10.4 mmol) and the mixture was stirred for 20 mins. Tetrahydro-2-(2-bromoethoxy)-2H-pyran (2.18 g, 10.4 mmol) in DMSO (10 mL) was added dropwise and the reaction was stirred for 1 hr. It was then diluted with brine (100 mL) and extracted with ethylacetate (3×100 mL). The organics were combined, dried with $MgSO_4$ and concentrated. The resulting residue was chromatographed (silica gel, hexanes:ether, 85:15) to afford tetrahydro-2-(2-(4-bromophenoxy)ethoxy)-2H-pyran (2.52 g, 85%) as a colorless oil.

A solution of 3-hydroxybenzaldehyde (1.27 g, 10.4 mmol), tetrahydro-2-(2-(4-bromophenoxy)ethoxy)-2H-pyran (6.26 g, 20.8 mmol), potassium carbonate (2.23 g, 16.12 mmol) and copper (330 mg, 5.2 mmol) in pyridine (10 mL) was refluxed for 5 days. It was then cooled to r.t., filtered through Celite, diluted with ethylacetate (50 mL), and washed with $H_2O$ (3×40 mL). The organic was dried with $MgSO_4$ and concentrated. The resulting residue was chromatographed (silica gel, ether:hexanes, 2:3) to afford tetrahydro-2-(2-(4-(3-formylphenoxy)phenoxy)ethoxy)-2H-pyran (3.09 g, 87%) as a pale yellow oil.

To a solution of N-methoxy-N-methyl diethylphosphoacetamide (Nuzillard et al. Tet. Letters, 30(29), 3779, 1989, 3.03 g, 12.7 mmol) in THF (40 mL) at −78° C., was added n-butyllithium (5.1 mL of a 2.5M solution in hexanes, 12.7 mmol) dropwise and the resulting mixture was stirred for 30 mins. Tetrahydro-2-(2-(4-(3-formylphenoxy)phenoxy)ethoxy)-2H-pyran (2.89 g, 8.5 mmol) in THF (5 mL) was then added dropwise. Upon completion of addition, the cooling bath was withdrawn and the reaction allowed to warm to r.t.. It was then quenched with aqu. sat'd NH₄Cl (50 mL) and extracted with ethylacetate (3×50 mL). The organics were combined, dried with MgSO₄ and concentrated. The resulting residue was chromatographed (silica gel, ether:hexanes, 3:1) to afford N-methoxy-N-methyl-trans-(3-(3-(4-(2-(2-(O-tetrahydro-2H-pyranyl)ethoxy)-phenoxy)phenyl)propenamide (3.37 g, 93%) as a pale yellow oil.

To a solution of trimethylsulfoxonium iodide (2.02 g, 9.2 mmol) in DMSO (35 mL) was added NaH (276 mg of 80% oil suspension, 9.2 mmol) and the resulting mixture was stirred for 20 mins. N-Methoxy-N-methyl-trans-(3-(3-(4-(2-(2-(O-tetrahydro-2H-pyranyl)ethoxy)-phenoxy)phenyl)propenamide (3.57 g, 8.4 mmol) was then added dropwise as a solution in DMSO (10 mL) and the reaction was stirred for 2 hrs at r.t. followed by heating at 50° C. for 1 hr. The reaction was then cooled to r.t., diluted with brine (100 mL) and extracted with ethylacetate (3×100 mL). The organics were combined, dried with MgSO₄ and concentrated. The resulting residue was chromatographed (silica gel, ether:hexanes, 7:3) to afford trans-(2-(3-(4-(2-(2-(O-tetrahydro-2H-pyranyl)ethoxy)phenoxy)phenyl)cyploroyl)-1-N-methoxy-N-methylcarboxyamide (2.79 g, 80%) as a colorless oil.

A solution of trans-(2-(3-(4-(2-(2-(O-tetrahydro-2H-pyranyl)ethoxy)phenoxy)phenyl)cyclopropyl)-1-N-methoxy-N-methylcarboxyamide (505 mg, 1.145 mmol) in 1:1 THF:1N HCl (5 mL) was stirred for 3 hrs. It was then diluted with water (10 mL) and extracted with ethylacetate (3×10 mL). The organics were combined, dried with MgSO₄ and concentrated. The resulting residue was chromatographed (silica gel, ether) to afford trans-(2-(3-(4-(2-hydroxyethoxy)phenoxy)phenyl)-cyclopropyl)-1-N-methoxy-N-methylcarboxyamide (299 mg, 73%).

The title compound was prepared according to the procedure of Example 10 substituting trans-(2-(3-(4-(2-hydroxyethoxy)phenoxy)phenyl)cyclopropyl)-1-N-methoxy-N-methylcarboxyamide for intermediate 6.2. m.p.=139°-141° C.: 1H NMR (300 MHz, DMSO-d₆): 0.87 (m, 2H), 1.30 (m, 1H), 1.82 (m, 1H), 3.36 (m, 2H), 3.71 (q, 2H, J=5.5 Hz), 3.97 (t, 2H, J=5.5 Hz), 5.37 (t, 1H, J=5.5 Hz), 6.26 (bs, 2H), 6.63 (m, 2H), 6.75 (d, 1H, J−7.5 Hz), 6.96 (s, 4H), 7.18 (m, 1H), 9.29 (s, 1H); MS (M+H)⁺=359; Analysis calc'd for $C_{19}H_{22}N_2O_5$: C, 63.67, H, 6.19, N, 7.82; Found: C, 63.60, H, 6.24, N, 7.57.

EXAMPLE 162

N-(2-trans-(2-(3-(4-methylphenoxy)phenyl)cyclopropyl)propyl)-N-hydroxyurea

To a solution of trans-(2-(3-(4-methylphenoxy)-phenyl)cyclopropyl)carboxaldehyde (3.35 g, 13.3 mmol) in THF (60 mL) at 0° C. was added methylmagnesium bromide (5.3 mL of a 3.0M solution in ether, 16.0 mmol) dropwise. Upon completion of addition, the reaction was allowed to stir for 30 mins. It was then diluted with brine (60 mL) and extracted with ethylacetate (3×60 mL) The organics were combined, dried with MgSO₄ and concentrated to afford trans-1-(2-(3-(4-methylphenoxy)phenyl)cyclopropyl)ethanol which was used as is.

To a solution of oxalyl chloride (1.94 g, 15.3 mmol) in CH₂Cl₂ (50 mL) at −78° C. was added DMSO (2.49 g, 31.92 mmol) dropwise and the resulting mixture was stirred for 5 mins. Trans-(1-(2-(3-(4-methylphenoxy)-phenyl)cyclopropyl)ethanol, from above, in CH₂Cl₂ (10 mL) was then added dropwise and the reaction was stirred for 20 mins. Triethylamine (6.72 g, 66.5 mmol) was then added dropwise, the cooling bath was withdrawn and the reaction allowed to warm to r.t. The reaction was diluted with water (60 mL) and the layers were separated. The aqueous was extracted with CH₂Cl₂ (2×60 mL). The organics were combined, dried with MgSO₄ and concentrated. The resulting residue was chromatographed (silica gel, ether:hexanes, 1:4) to afford trans-(2-(3-(4-methylphenoxy)phenyl)cyclopropyl)-1-acetaldehyde (3.20 g, 90%) as a pale yellow oil.

To a solution of (methoxymethyl)triphenylphosphonium chloride (6.19 g, 18.0 mmol) in THF (50 mL) at 0° C., was added n-butyllithium (7.2 mL of a 2.5M solution in hexanes, 18.0 mmol) dropwise, and the resulting mixture was stirred for 15 mins. Trans-(2-(3-(4-methylphenoxy)phenyl)cyclopropyl)-1-acetaldehyde (3.20 g, 12.0 mmol) was added as a solution in THF (5 mL) and the reaction was stirred for 15 mins. It was then quenched with 10% aqueous HCl (50 mL) and extracted with ethylacetate (3×50 mL). The organics were combined, dried with MgSO₄ and concentrated. The resulting residue was taken up in 1:1 1N HCl:THF (50 mL) and refluxed for 4 hrs. It was then cooled to r.t. and further diluted with water (25 mL). This solution was extracted with ethylacetate (3×50 mL). The organics were combined, dried with MgSO₄ and concentrated. The resulting residue was chromatographed (silica gel, hexanes:ether, 9:1) to afford trans-(2-((3-(4-methylphenoxy)phenyl)cyclopropyl)-1-(2-propionaldehyde) (1.74 g, 52%).

The title compound was prepared according to the procedure of Example 1 substituting trans-(2-(3-(4-methylphenoxy)phenyl)cyclopropyl)-1-(2-propionaldehyde) for intermediate 1.4. 1H NMR (300 MHz, DMSO-d₆, 2 diastereomers): 0.82 (m, 3H), 0.92 and 0.94 (d, 3H, J=6.5 Hz), 1.35 (m, 1H), 1.66 and 1.74 (m, 1H), 2.28 (s, 3H), 3.36 (m, 2H), 6.16 and 6.18 (bs, 2H), 6.56 (m, 2H), 6.79 (m, 1H), 6.89 (m, 2H), 7.18 (m, 3H), 9.14 and 9.15 (s, 1H); MS (M+H)⁺=341; Analysis calc'd for $C_{20}H_{24}N_2O_3 \cdot 3/4 H_2O$: C, 67.87, H, 7.26, N, 7.92; Found: C, 67.70, H, 6.90, N, 8.30.

EXAMPLE 163

N-(1-trans-(2-(3-(6-methyl-2-pyridyloxy)phenyl)cyclopropyl) methyl)-N-hydroxyurea.

The title compound was prepared according to the procedure of Example 10 substiuting trans-(2-(3-(6-methyl-2-pyridyloxy)phenyl)cyclopropyl)-1-N-methoxy-N-methyl carboxyamide for intermediate 6.2. 1H NMR (300 MHz, DMSO-d₆): 0.90 (m, 2H), 1.34 (m, 1H), 1.87 (m, 1H), 2.32 (s, 3H), 3.37 (m, 2H), 6.28 (bs, 2H), 6.72 (d, 1H, J=8.5 Hz), 6.77-6.91 (m, 3H), 6.98 (d, 1H, J=7.5 Hz), 7.25 (t, 1H, J=7.5 Hz), 7.71 (t, 1H, J=8.5 Hz), 9.32 (s, 1H); MS (M+H)⁺=314; Analysis calc'd for $C_{17}H_{19}N_3O_3 \cdot 3/4 H_2O$: C, 62.47, H, 6.32, N, 12.86; Found: C, 62.69, H, 6.10, N, 12.19.

EXAMPLE 164

N-(1-trans-(2-(3-(3-quinonyloxy)phenyl)cyclopropyl) methyl)-N-hydroxyurea. .

The title compound was prepared according to the procedure of Example 10 substituting trans-(2-(3-(3-quinonyloxy)phenyl)cyclopropyl)-1-N-methoxy-N-methylcarboxyamide for intermediate 6.2. 1H NMR (300 MHz, DMSO-d₆): 0.93 (t, 2H, J=7 Hz), 1.36 (m, 1H), 1.90 (m, 1H), 3.36 (2H under DMSO/H2O), 6.29 (bs, 2H), 6.91 (m, 3H), 7.31 (m, 1H), 7.59 (m, 1H), 7.69 (m, 1H), 7.78 (d, 1H, J=3 Hz), 7.93 (dd, 1H, J=1 Hz, J=8.5 Hz), 8.03 (d, 1H, J=8.5 Hz), 8.80 (d, 1H, J=3 Hz), 9.31 (s, 1H); MS (M+H)+ =350; Analysis calc'd for $C_{20}H_{19}N_3O_3 \cdot 3/4H_2O$: C, 66.19, H, 5.69, N, 11.58; Found: C, 66.47, H, 5.65, N, 11.35.

EXAMPLE 165

N-(1-trans-(2-(3-(4-ethoxyphenoxy)phenyl)cyclopropyl) methyl-N-hydroxy-N'-cyclopropylurea.

To a solution of cyclopropanecarboxylic acid (348 mg, 4.0 mmol) in benzene (18 mL) was added triethylamine (409 mg, 4.0 mmol) followed by diphenylphosphoryl azide (1.11 g, 4.0 mmol) and the mixture was heated at 90° C. for 1 hr. It was then cooled to r.t. and a solution of N-(1-trans-(2-(3-(4-ethoxyphenoxy)-phenyl)cyclopropyl)methyl)-N-hydroxylamine (1.21 g, 4.0 mmol) in benzene (2 mL) was added. The reaction was then brought back to 90° C. and stirred for 18 hrs. It was then cooled to r.t., diluted with aqu. sat'd NH4Cl (20 mL) and extracted with ethylacetate (3×20 mL). The organics were combined, dried with MgSO4 and concentrated. The resulting residue was chromatographed (silica gel, ether:hexanes, 9:1) followed by crystallization in ethylacetate/hexanes to afford the title compound. m.p.=74°-75° C.; 1H NMR (300 MHz, DMSO-d6): 0.42 (m, 2H), 0.53 (m, 2H), 0.86 (m, 2H), 1.30 (m, 1H), 1.33 (t, 3H, J=7 Hz), 1.82 (m, 1H), 3.35 (3H, under DMSO/H2O), 4.00 (q, 2H, J=7 Hz), 6.63 (m, 2H), 6.74 (bd, 1H, J=8 Hz), 6.87-6.99 (m, 5H), 7.17 (m, 1H), 9.21 (s, 1H); MS (M+H)+ =383; Analysis calc'd for $C_{22}H_{26}N_2O_4$: C, 69.09, H, 6.85, N, 7.33; Found: C, 68.92, H, 6.89, N, 7.32.

EXAMPLE 166

N-(1-trans-(2-(3-(2-thiazolyloxy)phenyl)cyclopropyl) methyl)-N-hydroxyurea

The title compound was prepared according to the procedure of Example 10 subsituting trans-(2-(3-(2-thiazolyloxy)phenyl)cyclopropyl)-1-N-methoxy-N-methylcarboxyamide for intermediate 6.2. m.p.=108°-110° C.; 1H NMR (300 MHz, DMSO-d6); 0.94 (t, 2H, J=7 Hz), 1.36 (m, 1H), 1.91 (m, 1H), 3.37 (m, 2H), 6.29 (bs, 2H), 7.01 (m, 2H), 7.08 (m, 1H), 7.22 (m, 1H), 7.28-7.36 (m, 2H), 9.32 (s, 1H); MS (M+H)+ =306; Analysis calc'd for $C_{14}H_{15}N_3O_3S$: C, 55.07, H, 4.95, N, 13.76; Found: C, 55.08, H, 4.94, N, 13.67.

EXAMPLE 167

N-(1-trans-(2-(3-(4-ethoxyphenoxy)phenyl)cyclopropyl) methyl)-N-hydroxyurea

The title compound was prepared according to the procedure of Example 10 substituting trans-(2-(3-(4-ethoxyphenoxy)phenyl)cyclopropyl-1-N-methoxy-N-methylcarboxyamide for intermediate 6.2. m.p.=118.0°-119.5° C.; 1H NMR (300 MHz, DMSO-d6): 0.87 (m, 2H), 1.28 (m, 1H), 1.32 (t, 3H, J=7 Hz), 1.82 (m, 1H), 3.35 (d, 2H, J=6.5 Hz), 4.00 (q, 2H, J=7 Hz), 6.24 (bs, 2H), 6.63 (m, 2H), 6.75 (d, 1H, J=7.5 Hz), 6.94 (m, 4H), 7.18 (m, 1H), 9.27 (s, 1H); MS (M+H)+ =343; Analysis calc'd for $C_{19}H_{22}N_2O_4 \cdot 1/4$-$H_2O$: C, 65.78, H, 6.54, N, 8.08; Found: C, 65.98, H, 6.47, N, 8.11.

EXAMPLE 168

N-(1-trans-(2-(3-(3-pyridyloxy)phenyl)cyclopropyl)methyl)-N-hydroxyurea

The title compound was prepared according to the procedure of Example 10 subsituting trans-(2-(3-(3-pyridyloxy)phenyl)cyclopropyl)-1-N-methoxy-N-methylcarboxyamide for intermediate 6.2. m.p.=102°-104° C.; 1H NMR (300 MHz, DMSO-d6): 0.91 (m, 2H), 1.34 (m, 1H), 1.87 (m, 1H), 3.37 (2H under DMSO/H2O), 6.28 (bs, 2H), 6.79 (m, 2H), 6.89 (d, 1H, J=8 Hz), 7.27 (m, 1H), 7.41 (m, 2H), 8.36 (m, 2H), 9.30 (s, 1H); MS (M+H)+ =300; Analysis calc'd for $C_{16}H_{17}N_3O_3$: C, 64.20, H, 5.73, N, 14.04; Found: C, 64.24, H, 5.83, N, 13.95.

EXAMPLE 169

N-(1-trans-(2-(3-(4-propylphenoxy)phenyl)cyclopropyl) methyl)-N-hydroxyurea

The title compound was prepared according to the procedure of Example 10 substituting trans-(2-(3-(4-propylphenoxy)phenyl)cyclopropyl)-1-N-methoxy-N-methylcarboxyamide for intermediate 6.2. m.p.=96°-98° C.; 1H NMR (300 MHz, DMSO-d6): 0.86 (m, 2H), 0.89 (t, 3H, J=7.5 Hz), 1.32 (m, 1H), 1.58 (sextet, 2H), 1.83 (m, 1H), 2.53 (t, 2H, J=7.5 Hz), 3.35 (d, 2H, J=7 Hz), 6.27 (bs, 2H), 6.69 (m, 2H), 6.79 (d, 1H, J=8.5 Hz), 6.91 (m, 2H), 7.19 (m, 3H), 9.29 (s, 1H); MS (M+H)+ =341; Analysis calc'd for $C_{20}H_{24}N_2O_3$: C, 70.56, H, 7.08, N, 8.23; Found: C, 70.86, H, 7.26, N, 8.26.

EXAMPLE 170

N-(1-trans-(2-(3-(2-methylphenoxy)phenyl)cyclopropyl) methyl)-N-hydroxyurea

The title compound was prepared according to the procedure of Example 10 substituting trans-(2-(3-(2-methylphenoxy)phenyl)cyclopropyl)-1-N-methoxy-N-methylcarboxyamide for intermediate 6.2. m.p.=82°-84° C.; 1H NMR (300 MHz, DMSO-d6): 0.88 (m, 2H), 1.31 (m, 1H), 1.82 (m, 1H), 2.17 (s, 3H), 3.35 (2H under DMSO/H2O), 6.26 (bs, 2H), 6.60 (m, 2H), 6.76 (d, 1H, J=8 Hz), 6.87 (m, 1H), 7.06-7.24 (m, 3H), 7.31 (m, 1H), 9.29 (s, 1H); MS (M+H)+ =330; Analysis calc'd for $C_{18}H_{20}N_2O_3$: C, 69.21, H, 6.45, N, 8.97; Found: C, 69.11, H, 6.48, N, 8.92.

EXAMPLE 171

N-(1-trans-(2-(3-(2-pyridyloxy)phenyl)cyclopropyl)methyl)-N-hydroxy-N'-methylurea The title compound was prepared, as an oil, according to the procedure of Example 10 substituting trans-(2-(3-(2-pyridyloxy)phenyl)cyclopropyl)-1-N-methoxy-N-methylcarboxyamide for intermediate 6.2 and methyl isocyanate for trimethylsilylisocyanate. 1H NMR (300 MHz, DMSO-d6): 0.90 (t, 2H, J=7 Hz), 1.33 (m, 1H), 1.87 (m, 1H), 2.58 (d, 3H, J=4.5 Hz), 3.36 (2H under DMSO/H2O), 6.79-6.90 (m, 4H), 6.99 (m, 1H), 7.12 (m, 1H), 7.26 (t, 1H, J=8 Hz), 7.84 (m, 1H), 8.15 (m, 1H), 9.23 (s, 1H); MS (M+H)+ =314.

EXAMPLE 172

Diastereomer A and B, N-(1-trans-(2-(3-(2-pyridyloxy)phenyl) cyclopropyl)ethyl)-N-hydroxyurea The title compound was prepared according to the procedure of Example 6 substituting 3-(2-pyridyloxy)-benzaldehyde for 3-phenoxybenzaldehyde. The diastereomers of the final product were separated chromatographically (silica gel, ether:methanol, 95:5). One diastereomer of the desired product: m.p.=98°-100° C.; 1H NMR (300 MHz, DMSO-d$_6$, a single diastereomer A): 0.84 (m, 1H), 0.98 (m, 1H), 1.14 (d, 3H, J=7 Hz), 1.26 (m, 1H), 1.86 (m, 1H), 3.61 (m, 1H), 6.29 (bs, 2H), 6.79-6.91 (m, 3H), 7.00 (d, 1H, J=8.5 Hz), 7.11 (m, 1H), 7.26 (t, 1H, J=8.5 Hz), 7.84 (m, 1H), 8.15 (m, 1H), 9.01 (s, 1H); MS (M+H)$^+$=314; Analysis calc'd for $C_{17}H_{19}N_3O_3 \cdot 1/4H_2O$: C, 64.24, H, 6.18, N, 13.22; Found: C, 63.85, H, 6.09, N, 13.15.

The other diastereomer B of the desired product: m.p.=120°-122° C.; 1H NMR (300 MHz, DMSO-d$_6$): 0.88 (m, 2H), 1.14 (d, 3H, J=7 Hz), 1.36 (m, 1H), 1.96 (m, 1H), 3.63 (m, 1H), 6.28 (bs, 2H), 6.78 (m, 1H), 6.86 (m, 2H), 6.99 (m, 1H), 7.11 (m, 1H), 7.24 (t, 1H, J=8.5 Hz), 7.84 (m, 1H), 8.15 (M, 1H), 9.01 (s, 1H); MS (M+H)$^+$=314; Analysis calc'd for $C_{17}H_{19}N_3O_3$: C, 65.16, H, 6.11, N, 13.41; Found: C, 65.18, H, 6.21, N, 13.37.

EXAMPLE 173

N-(1-trans-(2-(3-(3-methylphenoxy)phenyl)cyclopropyl) methyl)-N-hydroxy-N-methylurea The title compound was prepared as an oil according to the procedure of Example 10 substituting trans-(2-(3-(3-methylphenoxy)phenyl)cyclopropyl)-1-N-methoxy-N-methylcarboxyamide for intermediate 6.2 and methylisocyanate for trimethylsilylisocyanate. 1H NMR (300 MHz, DMSO-d$_6$): 0.89 (m, 2H), 1.30 (m, 1H), 1.84 (m, 1H), 2.29 (s, 3H), 2.57 (d, 3H, J=5 Hz), 3.33 (2H under DMSO/H$_2$O), 6.67-6.86 (m, 6H), 6.94 (d, 1H, J=8 Hz), 7.24 (q, 2H, J=8.5 Hz), 9.21 (s, 1H); MS (M+NH$_4$)$^+$=344.

EXAMPLE 174

N-(1-trans-(2-(3-(3-methylphenoxy)phenyl)cyclopropyl) methyl)-N-hydroxyurea

The title compound was prepared according to the procedure of Example 10 substituting trans-(2-(3-(3-methylphenoxy)phenyl)cyclopropyl)-1-N-methoxy-N-methylcarboxyamide for intermediate 6.2. m.p.=97.5°-99.0° C.; 1H NMR (300 MHz, DMSO-d$_6$): 0.88 (m, 2H), 1.33 (m, 1H), 1.84 (m, 1H), 2.29 (s, 3H), 3.35 (d, 2H, J=7 Hz), 6.27 (bs, 2H), 6.69-6.84 (m, 5H), 6.94 (m, 1H), 7.24 (m, 2H), 9.30 (s, 1H); MS (M+H)$^+$=313; Analysis calc'd for $C_{18}H_{20}N_2O_5$: C, 69.21, H, 6.45, N, 8.97; Found: C, 69.45, H, 6.46, N, 8.96.

EXAMPLE 175

N-(1-trans-(2-(3-(4-ethylphenoxy)phenyl)cyclopropyl) methyl)-N-hydroxy-N'-methyl-hydroxyurea The title compound was prepared according to the procedure of Example 10 substituting trans-(2-(3-(4-ethylphenoxy)phenyl)cyclopropyl-1-N-methoxy-N-methylcarboxyamide for intermediate 6.2 and methylisocyanate for trimethylsilylisocyanate. m.p.=107°-109° C.; 1H NMR (300 MHz, DMSO-d$_6$): 0.88 (m, 2H), 1.18 (t, 3H, J=8 Hz), 1.30 (m, 1H), 1.83 (m, 1H), 2.58 (d, 3H, J=5 Hz), 2.60 (q, 2H, J=8 Hz), 3.35 (d, 2H, under DMSO/H$_2$O), 6.69 (m, 2H), 6.78 (m, 1H), 6.84 (bq, 1H, J=5 Hz), 6.91 (m, 2H), 7.21 (m, 3H), 9.21 (s, 1H); MS (M+NH$_4$)$^+$=358; Analysis calc'd for $C_{20}H_{24}N_2O_3$: C, 70.56, H, 7.11, N, 8.23; Found: C, 70.55, H, 7.10, N, 8.22.

EXAMPLE 176

N-(1-trans-(2-(3-(4-ethylphenoxy)phenyl)cyclopropyl) methyl)-N-hydroxyurea

The title compound was prepared according to the procedure of Example 10 substituting trans-(2-(3-(4-ethylphenoxy)phenyl)cyclopropyl)-1-N-methoxy-N-methylcarboxyamide for intermediate 6.2. m.p.=106.5°-108.0° C.; 1H NMR (300 MHz, DMSO-d$_6$): 0.88 (m, 2H), 1.18 (t, 3H, J=7.5 Hz), 1.32 (m, 1H), 1.84 (m, 1H), 2.59 (q, 2H, J=7.5 Hz), 3.36 (d, 2H, J=7 Hz), 6.28 (bs, 2H), 6.69 (m, 2H), 6.80 (m, 1H), 6.92 (m, 2H), 7.22 (m, 3H), 9.30 (s, 1H); MS (M+H)$^+$=327; Analysis calc'd for $C_{19}H_{22}N_2O_3$: C, 69.91, H, 6.80, N, 8.58; Found: C, 69.95, H, 6.80, N, 8.56.

EXAMPLE 177

N-(1-trans-(2-(3-(4-fluorophenoxy)phenyl)cyclopropyl) methyl)-N-hydroxy-N'-methylurea The title compound was prepared according to the procedure of Example 10 substituting trans-(2-(3-(4-fluorophenoxy)phenyl)cyclopropyl)-1-N-methoxy-N-methylcarboxyamide for intermediate 6.2 and methylisocyanate for trimethylsilylisocyanate. m.p.=124°-125° C.; 1H NMR (300 MHz, DMSO-d$_6$): 0.88 (m, 2H), 1.31 (m, 1H), 1.84 (m, 1H), 2.57 (d, 3H, J=5.5 Hz), 3.35 (d, 2H, J=6.5 Hz), 6.71 (m, 2H), 6.83 (m, 2H), 7.04 (m, 2H), 7.23 (m, 3H), 9.21 (s, 1H); MS (M+H)$^+$=331; Analysis calc'd for $C_{18}H_{19}FN_2O_3$: C, 65.44, H, 5.80, N, 8.48; Found: C, 65.12, H, 5.80, N, 8.43.

EXAMPLE 178

N-(1-trans-(2-(3-(2-thienyloxy)phenyl)cyclopropyl)methyl)-N-hydroxyurea.

The title compound was prepared according to the procedure of Example 10 substituting trans-(2-(3-(2-thienyloxy)phenyl)cyclopropyl)-1-N-methoxy-N-methylcarboxyamide for intermediate 6.2. m.p.=135.0°-136.5° C.; 1H NMR (300 MHz, DMSO-d$_6$): 0.90 (m, 2H), 1.32 (m, 1H), 1.86 (m, 1H), 3.35 (m, 2H), 6.27 (bs, 2H), 6.65 (m, 1H), 6.78-6.91 (m, 4H), 7.07 (dd, 1H, J=2 Hz, J=6 Hz), 7.24 (t, 1H, J=8.5 Hz), 9.30 (s, 1H); MS (M+H)$^+$=305; Analysis calc'd for $C_{15}H_{16}N_2O_3S$: C, 59.19, H, 5.30, N, 9.21; Found: C, 59.36, H, 5.36, N, 9.20.

EXAMPLE 179

N-(1-trans-(2-(3-(4-methylphenoxy)phenyl)cyclopropyl) methyl)-N-hydroxy-N'-methylurea The title compound was prepared according to the procedure of Example 10 subsituting trans-(2-(3-(4-methylphenoxy)phenyl)cyclopropyl)-1-N-methoxy-N-methylcarboxyamide for intermediate 6.2 and methylisocyanate for trimethylsilylisocyanate. m.p.=90°-94° C.; 1H NMR (300 MHz. DMSO-d$_6$): 0.88 (m, 2H), 1.29 (m, 1H), 1.82 (m, 1H), 2.2 (s, 3H), 2.57 (d, 3H, J=4 Hz), 3.34 (d, 2H, J=7 H; 6.68 (m, 2H), 6.75-6.93 (m, 4H), 7.20 (m, 3H), 9.21 (s, 1H); MS $(M+NH_4)^+ = 344$; Analysis calc'd for $C_{19}H_{22}N_2O_3$: C, 69.91, H, 6.80, N, 8.58; Found: C, 69.59, H, 6.78, N, 8.55.

EXAMPLE 180

N-(1-trans-(2-(3-(4-methylphenoxy)phenyl)cyclopropyl) ethyl)-N-hydroxyurea

The title compound was prepared according to the procedure of Example 6 substituting 3-(4-methylphenoxy)benzaldehyde for 3-phenoxybenzaldehyde. m.p.=95°–101° C.; 1H NMR (300 MHz, DMSO-d$_6$, 75:25 ratio of diastereomers): 0.85 and 0.97 (m, 2H), 1.11 and 1.13 (d, 3H, J=7 Hz), 1.24 and 1.32 (m, 1H), 1.82 and 1.90 (m, 1H), 2.29 (s, 3H), 3.61 (m, 1H), 6.29 (bs, 2H), 6.66 (m, 2H), 6.78 (d, 1H, J=8 Hz), 6.89 (m, 2H), 7.19 (m, 3H), 8.99 and 9.01 (s, 1H); MS $(M+H)^+ = 327$; Analysis calc'd for $C_{19}H_{22}N_2O_3$: C, 69.91, H, 6.80, N, 8.58; Found: C, 69.60, H, 6.84, N, 8.40.

EXAMPLE 181

N-(1-trans-(2-(5-methyl-2-thienyl)cyclopropyl)ethyl)-N-hydroxy-N'-methylurea

The title compound was prepared according to the procedure of Example 6 substituting 5-methyl-2-thiophenecarboxaldehyde for 3-phenoxybenzaldehyde and methylisocyanate for trimethylsilylisocycante. m.p.=85°–88° C.; 1H NMR (300 MHz, DMSO-d$_6$, 30:70 ratio of diastereomers): 0.70–0.98 (m, 2H), 1.11 and 1.14 (d, 3H, J=7 Hz), 1.19 (m, 1H), 1.98 (m, 1H), 2.33 and 2.35 (bs, 1H), 2.59 and 2.62 (d, 3H, J=5 Hz), 3.54 (m, 1H), 6.48 and 6.53 (m, 2H), 6.85 and 6.90 (bq, 1H, J=5 Hz), 8.90 and 8.93 (s, 1H); MS $(M+H)^+ = 255$; Analysis calc'd for $C_{12}H_{18}N_2O_2S \cdot 1/4H_2O$: C, 55.68, H, 7.20, N, 10.82; Found: C, 55.98, H, 7.06, N, 10.92.

EXAMPLE 182

N-(1-trans-(2-(5-methyl-2-thienyl)cyclopropyl)-N-hydroxyurea

The title compound was prepared according to the procedure of Example 6 substituting 5-methyl-2-thiophenecarboxaldehyde for 3-phenoxybenzaldehyde. m.p.=123°–126° C.; 1H NMR (300 MHz, DMSO-d$_6$, 1:1 ratio of diastereomers): 0.76 (m, 1H), 0.85 and 0.96 (m, 1H), 1.13 and 1.15 (d, 3H, J=7 Hz), 1.20 and 1.30 (m, 1H), 1.95 and 2.02 (m, 1H), 2.33 and 2.34 (bs, 1H), 3.58 (m, 1H), 6.29 and 6.31 (bs, 2H), 6.53 (m, 2H), 9.00 and 9.01 (s, 1H); MS $(M+H)^+ = 241$; Analysis calc'd for $C_{11}H_{16}N_2O_2S$: C, 54.97, H, 6.71, N, 11.66; Found: C, 55.53, H, 6.88, N, 11.61.

EXAMPLE 183

N-(1-trans-(2-(2-furanyl)cyclopropyl)ethyl)-N-hydroxy-N'-methylurea

The title compound was prepared according to the procedure of Example 6 substituting 2-furaldehyde for 3-phenoxycarboxaldehyde and methylisocyanate for trimethylsilylisocyanate. m.p.=74°–77° C.; 1H NMR (300 MHz, DMSO-d$_6$, 2:1 ratio of diastereomers containing 10% of the cis isomer): 0.76–0.92 (m, 2H), 1.10 and 1.12 (d, 3H, J=6 Hz), 1.26–1.45 (m, 1H), 1.89 (m, 1H), 2.50 (d, 3H, J=5.5 Hz), 3.56 and 3.86 (m, 1H), 6.01 (m, 1H), 6.30 (m, 1H), 6.87 (m,1H), 7.41 (m, 1H), 8.89 and 8.91 and 8.94 and 8.95 (s, 1H); MS $(M+H)^+ = 225$; Analysis calc'd for $C_{11}H_{16}N_2O_2$: C, 58.91, H, 7.19, N, 12.49; Found: C, 59.28, H, 7.31, N, 12.22.

EXAMPLE 184

N-(1-trans-(2-(5-methyl-2-furanyl)cyclopropyl)ethyl)-N-hydroxy-N'-methylurea

The title compound was prepared according to the procedure of Example 6 substituting 5-methyl-2-furaldehyde for 3-phenoxybenzaldehyde and methylisocyanate for trimethylsilylisocyanate. m.p.=85°–88° C.; 1H NMR (300 MHz, DMSO-d$_6$, 60:40 ratio of diastereomers): 0.75 and 0.82 (m, 2H), 1.10 and 1.12 (d, 3H, J=6.5 Hz), 1.32 (m, 1H), 1.81 (m, 1H), 2.16 and 2.18 (s, 3H), 2.60 (d, 3H, J=5.5 Hz), 3.53 (m, 1H), 5.85 (m, 2H), 6.86 (m, 1H), 8.90 and 8.93 (s, 1H); MS $(M+H)^+ = 239$; Analysis calc'd for $C_{12}H_{18}N_2O_3$: C, 60.48, H, 7.61, N, 11.76; Found: C, 6062, H, 7.68, N, 11.71.

EXAMPLE 185

N-(1-trans-(2-(3-furanyl)cyclopropyl)methyl)-N-hydroxy-N'-methylurea

The title compound was prepared according to the procedure of Example 10 substituting trans-(2-(3-furanyl)cyclopropyl)-1N-methoxy-N-methylcarboxyamide for intermediate 6.2 and methylisocyanate for trimethylsilylisocyanate. m.p.=113°–114° C.; 1H NMR (300 MHz, DMSO-d$^6$): 0.69 (m, 1H), 0.77 (m, 1H), 1.17 (m, 1H), 1.62 (m, 1H), 2.59 (d, 3H, J=5.5 Hz), 3.31 (d, 2h, J=7 Hz), 6.24 (m, 1H), 6.85 (bq, 1H, J=5.5 Hz), 7.44 (m, 1H), 7.50 (t, 1H, J=1.5 Hz), 9.20 (s, 1H); MS $(M+H)^+ = 211$; Analysis calc'd for $C_{10}H_{14}N_2O_3$: C, 57.13, H, 6.71, N, 13.33; Found: C, 56.90, H, 6.74, N, 13.27.

EXAMPLE 186

N-(1-trans-(2-(3-thienyl)cyclopropyl)ethyl)-N-hydroxy-N'-methylurea

The title compound was prepared according to the procedure of Example 6 substituting 3-thiophenecarboxaldehyde for 3-phenoxybenzaldehyde and methylisocyanate for trimethylsilylisocyanate. m.p.=115°–117° C.; 1H NMR (300 MHz, DMSO-d$_6$, 60:40 ratio of diastereomers): 0.76 and 0.89 (m, 2H), 1.12 and 1.13 (d, 3H, J=7 Hz), 1.22 (m, 1H), 1.85 and 1.93 (m, 1H), 2.60 and 2.61 (d, 3H, J=5 Hz), 3.54 (m, 1H), 6.79–6.90 (m, 2H), 6.99 and 7.05 (m, 1H), 7.37 and 7.40 (dd, 1H, J=3 Hz, J=5.5 Hz), 8.89 and 8.93 (s, 1H); MS $(M+NH_4)^+ = 258$; Analysis calc'd for $C_{11}H_{16}N_2O_2S$: C, 54.97, H, 6.71, N, 11.66; Found: C, 54.90, H, 6.56, N, 11.66.

EXAMPLE 187

N-(1-trans-(2-(3-thienyl)cyclopropyl)methyl)-N-hydroxy-N'-methylurea

The title compound was prepared according to the procedure of Example 10 substituing trans-(2-(3-thienyl)cyclopropyl)-1-N-methoxy-N-methylcarboxyamide for intermediate 6.2 and methylisocyanate for trimethylsilylisocyanate. m.p.=129°–131° C.; 1H NMR (300 MHz, DMSO-d$_6$): 0.82 (m, 2H), 1.28 (m, 1H), 1.88 (m, 1H), 2.60 (d, 3H, J=5.5 Hz), 3.33 (d, 2H, J=7 Hz), 6.84 (m, 2H), 7.05 (dd, 1H, J=1 Hz, J=3 Hz), 7.40 (dd, 1H, J=3 Hz, J=5.5 Hz), 9.22 (s, 1H); MS $(M+NH_4)^+ = 244$; Analysis calc'd for $C_{10}H_{14}N_2O_2S$: C, 53.07, H, 6.24, N, 12.38; Found: C, 52.99, H, 6.17, N, 12.41.

EXAMPLE 188

N-(1-trans-(2-(3-thienyl)cyclopropyl)methyl)-N-hydroxyurea

The title compound was prepared according to the procedure of Example 10 substituting trans-(2-(3-thienyl)cyclopropyl)-1-N-methoxy-N-methylcarboxyamide for intermediate 6.2. m.p.=143°–145° C.; 1H NMR (300 MHz, DMSO-d$_6$): 0.83 (m, 2H), 1.30 (m, 1H), 1.88 (m, 1H), 3.33 (d, 2H, J=7 Hz), 6.28 (bs, 2H), 6.85 (dd, 1H, J=1 Hz, J=5.5 Hz), 7.06 (dd, 1H, J=3 Hz, J=3 Hz), 7.40 (dd, 1H, J=1 Hz, J=5.5 Hz), 9.30 (s, 1H); MS (M+NH$_4$)$^+$=230; Analysis calc'd for C$_9$H$_{12}$N$_2$O$_2$S: C, 50.92, H, 5.70, N, 13.20; Found: C, 50.72, H, 5.57, N, 13.19.

EXAMPLE 189

N-(1-trans-(2-(3-thienyl)cyclopropyl)ethyl)-N-hydroxyurea

The title compound was prepared acording to the procedure of Example 6 substituting 3-thiophenecarboxaldehyde for 3-phenoxybenzaldehyde. m.p.=129°–131° C.; 1H NMR (300 MHz, DMSO-d$_6$, 65:35 ratio of diastereomers): 0.80 and 0.91 (m, 2H), 1.13 and 1.14 (d, 3H, J=7 Hz), 1.16-1.35 (m, 1H), 1.85 and 1.95 (m, 1H), 3.57 (m, 1H), 6.28 and 6.30 (bs, 2H), 6.84 (m, 1H), 7.01 and 7.05 (dd, 1H, J=1.5 Hz, J=3 Hz), 7.37 and 7.40 (d, 1H, J=3 Hz, J=5 Hz), 8.98 and 9.00 (s, 1H); MS (M+H)$^+$=227; Analysis calc'd for C$_{10}$H$_{14}$N$_2$O$_2$S: C, 53.07, H, 6.24, N, 12.38; Found: C, 53.29, H, 6.34, N, 12.28.

EXAMPLE 190

N-(1-trans-(2-(2-thienyl)cyclopropyl)methyl)-N-hydroxyacetamide

The title compound was prepared according to the procedure of Example 27 substituting N-(1-trans-(2-(3-thienyl)cyclopropyl)methyl)-N-hydroxylamine for N-(1-trans-(2-phenylcyclopropyl)methyl)-N-hydroxylamine. m.p.=71°–73° C.; 1H NMR (300 MHz, DMSO-d$_6$): 0.88 (m, 1H), 0.98 (m, 1H), 1.34 (m, 1H), 2.00 (s, 3H), 2.10 (m, 1H), 3.51 (m, 2H), 6.78 (d, 1H, J=3 Hz), 6.89 (dd, 1H, J=3 Hz, J=5.5 Hz), 7.22 (dd, 1H, J=1 Hz, J=5.5 Hz), 9.82 (bs, 1H); MS (M+H)$^+$=212; Analysis calc'd for C$_{10}$H$_{13}$NO$_2$S: C, 56.85, H, 6.20, N, 6.63; Found: C, 57.13, H, 6.30, N, 6.66.

EXAMPLE 191

N-(1-trans-(2-(3-furanyl)cyclopropyl)ethyl)-N-hydroxy-N'-methylurea

The title compound was prepared according to the procedure of Example 6 substituting 3-furaldehyde for 3-phenoxycarboxaldehyde and methylisocyanate for trimethylsilylisocyanate. m.p.=133°–135° C.; 1H NMR (300 MHz, DMSO-d$_6$, 97:3 ratio of diastereomers): 0.70 (m, 2H), 1.11 (d, 3H, J=6.5 Hz), 1.17 (m, 1H), 1.68 (m, 1H), 2.60 (d, 3H, J=5 Hz), 3.51 (m, 1H), 6.20 (m, 1H), 6.89 (bq, 1H, J=5 Hz), 7.38 (m, 1H), 7.48 (t, 1H, J=2 Hz), 8.86 and 8.91 (s, 1H); MS (M+H)$^+$=225; Analysis calc'd for C$_{11}$H$_{16}$N$_2$O$_3$: C, 58.91, H, 7.19, N, 12.49; Found: C, 59.05, H, 7.29, N, 12.51.

EXAMPLE 192

N-(1-trans-(2-(3-furanyl)cyclopropyl)ethyl)-N-hydroxyurea

The title compound was prepared according to the procedure of Example 6 substituting 3-furaldehyde for 3-phenoxybenzaldehyde and methylisocyanate for trimethylsilylisocyanate. m.p.=128°–130° C.; 1H NMR (300 MHz, DMSO-d$_6$, 90:10 ratio of diastereomers): 0.70 (m, 2H), 1.11 (d, 3H, J=7 Hz), 1.18 (m, 1H), 1.70 (m, 1H), 3.56 (m, 1H), 6.24 (m, 1H), 6.30 (bs, 2H), 7.39 (m, 1H), 7.49 (t, 1H, J=2 Hz), 8.96 and 8.97 (s, 1H); MS (M+H)$^+$=211; Analysis calc'd for C$_{10}$H$_{14}$N$_2$O$_3$: C,57.13, H, 6.71, N, 13.33; Found: C, 57.06, H, 6.87, N, 12.99.

EXAMPLE 193

N-(1-trans-(2-(3-furanyl)cyclopropyl)methyl)-N-hydroxyurea

The title compound was prepared according to the procedure of Example 10 substituting trans-(2-(3-furanyl)cyclopropyl)-1-N-methoxy-N-methylcarboxyamide for intermediate 6.2. m.p.=108.5°–110.5° C.; 1H NMR (300 MHz, DMSO-d$_6$): 0.69 (m, 1H), 0.77 (m, 1H), 1.19 (m, 1H), 1.63 (m, 1H), 3.31 (d, 2H, J=7 Hz), 6.25 (m, 1H), 6.28 (bs, 2H), 7.44 (bs, 1H), 7.51 (t, 1H, J=2 Hz), 9.28 (s, 1H); MS (M+H)$^+$=197; Analysis calc'd for C$_9$H$_{12}$N$_2$O$_3$: C, 55.09, H, 6.17, N, 14.28; Found: C, 55.02, H, 6.09, N, 14.17.

EXAMPLE 194

N-(1-trans-(2-(2-thienyl)cyclopropyl)methyl)-N-hydroxyurea

The title compound was prepared according to the procedure of Example 10 substituting trans-(2-(2-thienyl)cyclopropyl)-1-N-methoxy-N-methylcarboxyamide for intermediate 6.2. m.p.=112°–114° C.; 1H NMR (300 MHz, DMSO-d$_6$): 0.85 (m, 1H), 0.96 (m, 1H), 1.34 (m, 1H), 2.07 (m, 1H), 3.36 (2H under DMSO/H$_2$O), 6.31 (bs, 2H), 6.79 (m, 1H), 6.90 (dd, 1H, J=3.5 Hz, J=5.5 Hz), 7.21 (dd, 1H, J=1 Hz, J=5.5 Hz), 9.32 (s, 1H); MS (M+NH$_4$)$^+$=230; Analysis calc'd for C$_9$H$_{12}$N$_2$O$_2$S: C, 50.92, H, 5.70, N, 13.20; Found: C, 50.60, H, 5.69, N, 13.36.

EXAMPLE 195

N-(1-trans-(2-(2-furanyl)cyclopropyl)methyl)-N-hydroxyacetamide

The title compound was prepared according to the procedure of Example 27 substituting N-(1-trans-(2-(2-furanyl)cyclopropyl)methyl)-N-hydroxylamine for N-(1-trans-(2-phenylcyclopropyl)methyl)-N-hydroxylamine. m.p.=72°–74° C.; 1H NMR (300 MHz, DMSO-d$_6$): 0.88 (m, 2H), 1.41 (m, 1H), 1.91 (m, 1H), 1.99 (s, 3H), 3.50 (m, 2H), 6.05 (d, 1H, J=3 Hz), 6.32 (dd, 1H, J=2 Hz, J=3 Hz), 7.43 (m, 1H), 9.82 (bs, 1H); MS (M+NH$_4$)$^+$=213; Analysis calc'd for C$_{10}$H$_{13}$NO$_3$: C, 61.52, H, 6.71, N, 7.18; Found: C, 61.40, H, 6.77, N, 7.08.

EXAMPLE 196

N-(1-trans-(2-(2-thienyl)cyclopropyl)ethyl)-N-hydroxyacetamide

The title compound was prepared as an oil according to the procedure of Example 27 substituting N-(1-trans-(2-(2-thienyl)cyclopropyl)ethyl)-N-hydroxylamine for N-(1-trans-(2-phenylcylopropyl)methyl)-N-hydroxylamine. 1H NMR (300 MHz, DMSO-d$_6$, 2:1 ratio of diastereomers): 0.78-1.03 (m, 2H), 1.17 and 1.21 (d, 3H, J=7 Hz), 1.24-1.42 (m, 1H), 1.99 (s, 3H), 2.06 and 2.14 (m, 1H), 3.94 (m, 1H), 6.74 and 6.79 (d, 1H, J=3.5 Hz), 6.89 (m, 1H), 7.20 and 7.23 (dd, 1H, J=1 Hz, J=5.5 Hz), 9.53 and 9.55 (s, 1H); MS (M+NH$_4$)$^+$=243; Aanalysis calc'd for C$_{11}$H$_{15}$NO$_2$S: C, 58.64, H, 6.71, N, 6.22; Found: C, 58.47, H, 6.81, N, 6.13.

EXAMPLE 197

N-(1-trans-(2-(2-thienyl)cyclopropyl)ethyl)-N-hydroxyurea

The title compound was prepared according to the procedure of Example 6 substituting 2-thiophenecarboxaldehyde for 3-phenoxybenzaldehyde. m.p.=126°-131° C.; 1H NMR (300 MHz, DMSO-d$_6$, 1:1 ratio of diasteromers): 0.81 (m, 1H), 0.92 and 1.02 (m, 1H), 1.13 and 1.16 (d, 3H, J=7 Hz), 1.26 and 1.35 (m, 1H), 2.06 and 2.12 (m, 1H), 3.60 (m, 1H), 6.30 and 6,32 (bs, 2H), 6.77 (m, 1H), 6.88 (m, 1H), 7.20 (m, 1H), 9.02 and 9.03 (s, 1H); MS (M+NH$_4$)$^+$=244; Analysis calc'd for C$_{10}$H$_{14}$N$_2$O$_2$S: C, 53.07, H. 6.24, N, 12.38; Found: C, 52.93, H, 6.30, N, 12.59.

EXAMPLE 198

N-(1-trans-(2-(2-furanyl)cyclopropyl)methyl)-N-hydroxyurea

The title compound was prepared according to the procedure of Example 10 substituting trans-(2-(2-furanyl)cyclopropyl)-N-methoxy-N-methylcarboxyamide for intermediate 6.2. m.p.=108°-110° C.; 1H NMR (300 MHz, DMSO-d$_6$): 0.86 (m, 2H), 1.40 (m, 1H), 1.87 (m, 1H), 3.35 (m, 2H), 6.03 (d, 1H, J=3.5 Hz), 6.30 (m, 3H), 7.42 (m, 1H), 9.33 (s, 1H); MS (M+H)$^+$=197; Analysis calc'd for C$_9$H$_{12}$N$_2$O$_3$: C, 55.09, H, 6.17, N, 14.28; Found: C, 54.93, H, 6.23, N, 14.31.

EXAMPLE 199

N-(1-trans-(2-(2-(4-chlorophenoxy)-5-thiazolyl)cyclopropyl)methyl)-N-hydroxyurea To a suspension of copper (II) bromide (43.96 g, 196.8 mmol) in acetonitrile (600 mL) was added t-butyl nitrite (25.37 g, 246 mmol). Upon completion of addition, the mixture was warmed to 65° C. Ethyl-2-amino-5-thiazolecarboxylate (H. Erlenmeyer, Ch. J. Morel, Helv. Chim. Acta, 25,1073, 1942, 28.21 g, 164 mmol) was added very slowly and dropwise as a solution in acetonitrile (200 mL). Upon completion of addition, the reaction was stirred for 10 mins at 65° C. It was then cooled to r.t. and quenched with 10% HCl (800 mL). This mixture was then extracted with ethylacetate (3×800 mL). The organics were combined, dried with MgSO$_4$ and concentrated. The resulting residue was chromatographed (silica gel, hexanes:ether, 9:1) to afford ethyl 2-bromo-5-thiazolecarboxylate (24.67 g, 64%) as an off white solid.

To a solution of 4-chlorophenol (4.24 g, 33 mmol) in DMSO (100 mL) was added sodium hydride (857 mg of a 97% dry sample, 34.65 mmol) and the mixture was stirred for 20 mins. Ethyl 2-bromo-5-thiazolecarboxylate (7.79 g, 33 mmol) was then added as a solution in DMSO (10 mL) and the reaction was heated at 150° C. for 18 hrs. It was then cooled to r.t., diluted with brine (150 mL) and extracted with ethylacetate (3×150 mL). The organics were combined, dried with MgSO$_4$ and concentrated to afford ethyl 2-(4-chlorophenoxy)-5-thiazolecarboxylate which was used as is.

A solution of ethyl 2-(4-chlorophenoxy)-5-thiazolecarboxylate from above in 1:1 1N LiOH:THF (150 mL) was heated at 50° C. for 1 hr. It was then cooled to r.t. and the THF was stripped off in vacuo. The resulting aqueous solution was poured into 1:1 conc. HCl:ice (200 mL), the precipitate was collected, taken up in ethylacetate (250 mL), dried with MgSO$_4$ and concentrated to afford 2-(4-chlorophenoxy)-5-thiazolecarboxylic acid (7.49 g, 89% over the two steps) as an off-white solid.

To a solution of 2-(4-chlorophenoxy)-5-thiazolecarboxylic acid (7.49 g, 29.3 mmol) in CH$_2$Cl$_2$ (150 mL) was added oxalyl chloride (4.46 g, 35.2 mmol) dropwise followed by one drop of N,N-dimethylformamide and the reaction was allowed to stir for 1 hr. It was then concentrated in vacuo.

The residue from above was taken up in CH$_2$Cl$_2$ (150 mL) and cooled to 0° C. N,O-dimethylhydroxylamine hydrochloride (3.43 g, 35.2 mmol) was added followed by the dropwise addition of pyridine (5.6 g, 70.32 mmol). The cooling bath was withdrawn and the reaction allowed to warm to r.t. It was then diluted with brine (150 mL) and the layers were separated. The aqueous was extracted with CH$_2$Cl$_2$ (2×150 mL). The organics were combined, dried with MgSO$_4$ and concentrated. The resulting residue was chromatographed (silica gel, ether:hexanes, 3:2) to afford 2-(4-chlorophenoxy)-5-N-methoxy-N-methyl-thiazolecarboxamide (7.74 g, 89%) as a pale yellow solid.

To a solution of 2-(4-chlorophenoxy)-5-N-methoxy-N-methyl-thiazolecarboxamide (7.74 g, 26.0 mmol) in THF (100 mL) at 0° C., was added diisobutylaluminum hydride (26.0 mL of a 1.0M solution in hexanes, 26.0 mmol) dropwise. Upon completion of addition, the reaction was allowed to stir for 30 mins. It was then quenched, with 10% HCl (100 mL), the cooling bath was withdrawn and the mixture allowed to warm to r.t. The mixture was then extracted with ethylacetate (3×100 mls). The organics were combined, dried with MgSO$_4$ and concentrated to afford 2-(4-chlorophenoxy)-5-thiazolecarboxaldehyde which was used as is.

A solution of 2-(4-chlorophenoxy)-5-thiazolecarboxaldehyde from above and (carboethoxymethylene)triphenylphosphorane (9.51 g, 27.3 mmol) in toluene (125 mL) was refluxed for 1 hr. It was then cooled to r.t. and concentrated in vacuo. The residue was taken up in ether and the triphenylphosphine filtered off. The filtrate was concentrated to afford ethyl trans-3-(2-(4-chlorOphenoxy)-5-thiazolyl)propenoate which was used as is.

A solution of ethyl trans-3-(2-(4-chlorophenoxy)-5-thiazolyl)propenoate from above in 1:1 1N LiOH:THF (120 mL) was heated at 50° C. for 5 hrs. It was then cooled to r.t. and the THF was stripped off. The aqueous residue was poured into 1:1 ice:conc. HCl (100 mL), the precipitate was collected, taken up in ethylacetate(150 mL), dried with MgSO$_4$ and concentrated to afford trans-3-(2-(4-chlorophenoxy)-5-thiazolyl)propenoic acid as an off-white solid.

The title compound was prepared according to the procedure of Example 10 substituting trans-(2-(2-(4-chlorophenoxy)-5-thiazolyl)cyclopropyl)-1-N-methoxy-N-methylcarboxyamide for intermediate 6.2. m.p.=90.5°-92.5° C.; 1H NMR (300 MHz, DMSO-d$_6$): 0.85 (m, 2H), 1.43 (m, 1H), 1.85 (m, 1H), 3.32 (m, 2H), 6.27 (bs, 2H), 6.78 (s, 1H), 7.38 (m, 2H), 7.53 (m, 2H), 9.29 (s, 1H); MS (M+H)+ =340; Analysis calc'd for C$_{14}$H$_{14}$ClN$_3$O$_3$S: C, 49.48, H, 4.15, N, 12.37; Found: C, 49.33, H, 4.11, N, 12.35.

EXAMPLE 200

N-(1-trans-(2-(2-(5-(4-fluorophenoxy)furanyl)cyclopropyl)methyl)-N-hydroxyurea

The title compound was prepared according to the procedure of Example 10 substituting trans-(2-(5-(4-fluorophenoxy)furanyl)cyclopropyl)-1-N-methoxy-N-methylcarboxyamide for intermediate 6.2. 1H NMR (300 MHz, DMSO-d$_6$): 0.83 (m, 2H), 1.35 (m, 1H), 1.79 (m, 1H), 3.6 (2H under DMSO/H$_2$O), 5.61 (d, 1H, J=3.5 Hz), 6.03 (m, 1H), 6.28 (bs, 2H), 7.07 (m, 2H), 7.22 (m, 2H), 9.31 (s, 1H).

We claim:

1. A compound having the structure

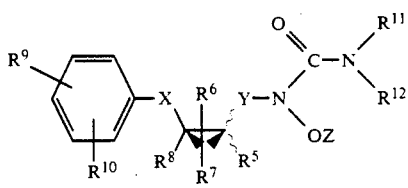

wherein

X and Y are independently selected from a valence bond or divalent alkylene of from one to four carbon atoms;

R$^5$ and R$^8$ are independently hydrogen or alkyl of from one to four carbon atoms;

R$^6$ and R$^7$ are independently selected from hydrogen, alkyl of from one to four carbon atoms, and halogen;

R$^9$ is selected from hydrogen, alkyl of from one to six carbon atoms, haloalkyl of from one to six carbon atoms, alkoxy of from one to six carbon atoms, and halogen;

R$^{10}$ is selected from 2-, 3-, or 4-pyridyloxy, optionally substituted with alkyl of from one to six carbon atoms, haloalkyl of from one to six carbon atoms, alkoxy of from one to six carbon atoms, or halogen;

R$^{11}$ and R$^{12}$ are independently hydrogen or alkyl of from one to six carbon atoms; and Z is hydrogen or a pharmaceutically acceptable cation.

2. A compound as defined by claim 1 selected from the group consisting of

N-(1-trans-(2-(3-(2-pyridyloxy)phenyl)cyclopropyl)methyl)-N-hydroxyurea;

N-(1-trans-(2-(3-(4-pyridyloxy)phenyl)cyclopropyl)methyl)-N-hydroxyurea;

N-(1-trans-(2-(3-(3-pyridyloxy)phenyl)cyclopropyl)methyl)-N-hydroxyurea.

N-(1-trans-(2-(3-(2-pyridyloxy)phenyl)cyclopropyl)methyl)-N-hydroxy-N'-methylurea; and N-(1-trans-(2-(3-(2-pyridyloxy)phenyl) cyclopropyl)ethyl)-N-hydroxyurea.

3. A pharmaceutical composition for use in inhibiting 5-lipoxygenase comprising a therapeutically effective amount of a compound as defined by claim 1 in combination with a pharmaceutically acceptable carrier.

4. A method of inhibiting 5-lipoxygenase activity in a host animal in need of such treatment comprising administering a therapeutically effective amount of a compound as defined by claim 1.

* * * * *